(12) United States Patent
Robinson et al.

(10) Patent No.: US 6,444,194 B1
(45) Date of Patent: Sep. 3, 2002

(54) INDIUM PHOTOSENSITIZERS FOR PDT

(75) Inventors: Byron C. Robinson; Avinash S. Phadke, both of Santa Barbara, CA (US)

(73) Assignee: Miravant Pharmaceuticals, Inc., Santa Barbara, CA (US)

( * ) Notice: Subject to any disclaimer, the term of this patent is extended or adjusted under 35 U.S.C. 154(b) by 0 days.

(21) Appl. No.: 09/308,884

(22) PCT Filed: Jun. 29, 1998

(86) PCT No.: PCT/US98/13601

§ 371 (c)(1),
(2), (4) Date: May 26, 1999

(87) PCT Pub. No.: WO00/00204

PCT Pub. Date: Jan. 6, 2000

Related U.S. Application Data

(63) Continuation of application No. 08/801,841, filed on Feb. 14, 1997, now abandoned.

(51) Int. Cl.[7] .................... A61K 31/409; C07D 487/22
(52) U.S. Cl. .................... 424/9.61; 424/9.6; 514/183; 514/185; 540/145; 540/472; 540/475
(58) Field of Search .................... 540/145, 472, 540/474, 475; 514/183, 185; 424/9.6, 9.61

(56) References Cited

U.S. PATENT DOCUMENTS

| | | | |
|---|---|---|---|
| 4,656,186 A | 4/1987 | Bommer et al. | 514/410 |
| 4,675,338 A | 6/1987 | Bommer et al. | 514/410 |
| 4,693,885 A | 9/1987 | Bommer et al. | 424/2 |
| 4,849,207 A | 7/1989 | Sakata et al. | 424/1.1 |
| 4,977,177 A | 12/1990 | Bommer et al. | 514/410 |
| 5,004,811 A | 4/1991 | Bommer et al. | 540/145 |
| 5,051,415 A | 9/1991 | Morgan et al. | 514/185 |
| 5,066,274 A | 11/1991 | Bommer et al. | 540/145 |
| 5,268,371 A | 12/1993 | Mauclaire et al. | 514/185 |
| 5,591,847 A | 1/1997 | Hemmi et al. | 424/9.362 |
| 5,599,928 A | 2/1997 | Hemmi et al. | 540/474 |
| 5,648,485 A | 7/1997 | Dolphin et al. | 540/145 |
| 5,674,467 A | 10/1997 | Maier et al. | 424/1.65 |
| 5,733,903 A | 3/1998 | Sessler et al. | 514/185 |
| 5,831,088 A | 11/1998 | Dolphin et al. | 540/474 |
| 5,877,165 A | 3/1999 | Miura et al. | 514/64 |

FOREIGN PATENT DOCUMENTS

| | | |
|---|---|---|
| JP | 3-261786 | 12/1991 |
| JP | 5-97857 | 4/1993 |

OTHER PUBLICATIONS

Sakata et al, 1993, vol. 119 Chemical Abstracts 203241c p. 875.

Maier et al, 1995, vol. 122 Chemical Abstracts, 160040d p. 942.

Primary Examiner—Richard L. Raymond
(74) Attorney, Agent, or Firm—John C. Purdue; David C. Purdue

(57) ABSTRACT

The invention disclosed herein involves a phototherapeutic pyrrolic core complexed with a non-radioactive Indium atom. Complexation of Indium by the pyrrolic core forms a metalopyrrolic compound which influences enables these compounds to localize at target sites a phototherapy. Such functionally aids in both detection and phototherapy of disease sites, or provides functionality that binds to site specific receptors of a target area such that the therapy is improved.

87 Claims, 4 Drawing Sheets

INDIUM PHOTOSENSITIZERS FOR PDT

REFERENCE TO RELATED APPLICATION

This is a continuation in part of application Ser. No. 08/801,841, filed Feb. 14, 1997, now abandoned, and is the U.S. designation of PCT/US98/13601, which was copending with Ser. No. 08/801,841.

BACKGROUND OF THE INVENTION

Porphyrins and related pyrrolic macrocycles, particularly tetrapyrrolic macrocycles, as well as many other light absorbing compounds are currently receiving a great deal of attention with regard to photosensitized medicine, especially in the field of Photodynamic therapy (PDT)[1]. The therapy necessarily involves the localization of a photosensitizing agent at or near a site of disease. The sensitizer, upon illumination in the presence of oxygen, produces cytotoxic species of oxygen such as singlet oxygen or oxygen radicals, which destroy the diseased cells. As the sensitizer is innocuous at the therapeutic dose, and only becomes active on illumination with light of a specific wavelength, PDT offers the possibility of a level of control or selectivity in the treatment of diseases not found with other current methods (e.g. conventional chemotherapy). Photodynamic therapy has wide application to modern medicine, targeting diseases such as cancers, cardiovascular restenosis and plaques, psoriasis, viral infections, benign prostate hyperplasia and diabetic retinopathy. In addition, photodynamic therapy may also be useful for the sterilization of blood, an area of increasing concern, especially now with the advent of AIDS and the transmission of HIV through blood transfusions.

Most research on PDT has centered on a complex mixture consisting of ill-defined porphyrin dimers, trimers and oligomers[2], which is marketed under the designation Photofrin II®. This complex mixture has recently been recommended for approval in the treatment of obstructed endobronchial tumors by the Food and Drug Administration Advisory Panel. Although the mixture has demonstrated the potential benefits of PDT, it has by virtue of its composition a number of associated disadvantages. For example, each of its components has varied subcellular localizations, depending on structure and inherent differences in photophysical properties. This makes the interpretation of pharmacokinetic data difficult. In addition, the composition of the oligomers is often difficult to reproduce and changes, depending on the conditions under which a solution[3] thereof is stored. Hence, the true "active components" may vary considerably. The mixture has a less than optimal light absorption profile (630 nm, $\epsilon \sim 3,000$ cm$^{-1}$M$^{-1}$). Numerous studies on light penetration through tissues show that longer wavelength light penetrates deeper into tissues[4]. While not all applications of PDT require deep penetration of light, many applications of PDT require the maximum depth of light penetration possible (for example the treatment of brain tumors). The mixture has a severe adverse normal skin response to light, which often lasts for up to 12 weeks[5] after therapy. During this time patients must avoid strong light, as otherwise severe burns and edema occur.

Several well characterized second Generation sensitizers (SnET2[6], ZnPc[7], BPDMA[8], THPC[9]) are currently in phase I/II clinical trials and the continued development of new sensitizers that show improved therapeutic efficacy is crucial to the future progress of the therapy. The development of new photosensitizers that possess all the basic requirements to be effective PDT drugs is not an easy task. While the optimal photophysical properties of a second generation drug are well defined, the factors which aid in the localization of photosensitizers to tissues are not. Several investigators have attempted to ascertain structure-activity relationships in ring systems that lend themselves to chemical modification without dramatically influencing the photophysical properties of the compounds. Woodburn and coworkers, working on hematoporphyrin based analogues, have proposed that anionic compounds tend to localize in lysosomes, while cationic photosensitizers tend to localize in the mitochondria. Pandey and coworkers have suggested that the lipophilicity of the compound is important, and have demonstrated in a chlorophyll derived series that PDT effects vary with the length of the ether carbon chain. Unfortunately, many of the correlation's found in one group of photosensitizing compounds do not transfer to different groups of photosensitizing compounds. Thus, while structure-activity relationships are valuable for a particular class of compound whose geometry and spatial arrangements vary only slightly, a different class of compound, that inherently has its own spatial and geometric parameters, must have its own structure-activity relationships investigated. This in itself is a large time consuming process with ultimately no guarantees of enhanced localization or improved PDT efficacy for the modified compound.

The instant invention is based upon the discovery of a single simple chemical modification of compounds having a pyrrolic core involving the coordination of a non-radioactive indium salt into the central cavity of the pyrrolic core to produce an indium pyrrolic complex, which markedly enhances the biological efficacy of compounds as photosensitizers for PDT.

Two isotopes of indium occur naturally: $In^{113}$ and $In^{115}$; the former (natural abundance 4.23%) has no radioactivity, while the latter (natural abundance 95.77%) has a half life of $6 \times 10^{14}$ years, and, as a result, is also considered to be non-radioactive. Other indium nuclides have half lives ranging from 50.0 days (for $In^{114m}$) to 0.2 second (for $In^{109m}2$).

THE PRIOR ART

Tetrapyrroles containing Indium$^{111}$ (half life 2.81 days) and other metals are known in the art, being disclosed, by way of example, in Japanese Kokai 3-261786, 1991, Mauclaire et al., U.S. Pat. No. 5,268,371 and in Maier et al., U.S. Pat. No. 5,674,467, which also disclose their use for diagnostic imaging. The metal-tetrapyrrole compounds are all water soluble, and contain functional groups capable of coupling a biologically active molecule, such as an antibody, to the tetrapyrrolic nucleus. The compounds usually are prepared by reacting a porphyrin derivative with a solution of a salt of the metal to be complexed at a temperature and for a time sufficient to obtain the metal tetrpyrrole compound. For example, when a metal salt of indium$^{111}$ is heated for three hours at 110° C. in a porphyrin solution to which a mixture of acetic acid and sodium acetate has been added, an $In^{111}$porphyrin is produced. Although the preparation of such metalloporphyrins is known and the compounds have been discussed in the context of radiocontrasting agents, surprisingly, so far as is known, there has been no report on the efficacy of indiumporphyrins as therapeutic photosensitizers. In view of the substantial prior art involving indium tetrapyrroles, it is indeed surprising to discover that complexes of non-radioactive indium with tetrapyrroles exhibit a marked improvement in their cytocidal effect in vivo when compared with other metallotetrapyrrole complexes.

Sakata, U.S. Pat. No. 4,849,207, discloses compounds having the following structure:

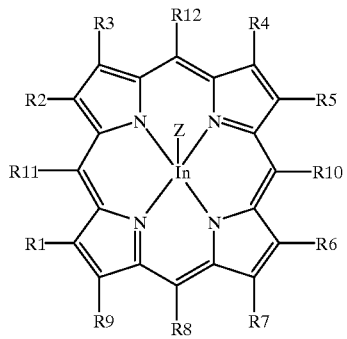

where:

R1, R2, R4 and R6 are methyl, R8, R10, R11 and R12 are H, and R7 and R9 are $CH_2CH_2COR13$ (where R13 is a residue which results when H is removed from an amino acid), R3 and R5 are ethyl, and In is not radioactive, i.e., is $In^{113}$ or $In^{115}$.

Japanese Kokai 5-97857 discloses compounds having the following structure

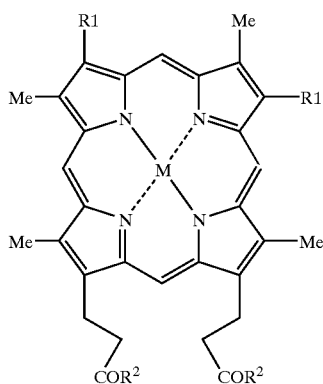

Where R1 is CH(OR)Me, R is alkyl, R2 is a residue derived by removing H from an amino acid, and M is 2H, Ga, Zn, Pd, In or Sn.

The Following References Are Cited Above

1. For an overview of photodynamic therapy see "Photodynamic Therapy of Neoplastic Disease", Vol. I and II, Ed. Kessel, D., CRC Press, 1990.
2. "Photodynamic Therapy of Neoplastic Disease", Vol. I and II, Ed. Kessel, D., CRC Press, 1990p1–12.
3. Byrne, C. J., Ward, A. D., Marshallsay, C. J. *Photochem. Photobiol.*, 46, 575, 1987.
4. a)Svaasand, L. O., Ellingsen, R. *Photochem. Photobiol.* 41, 73, 1985:b) Bolin, F. P., Preuss. L. E., Cain, B. W., in "Porphyrin Localization and Treatment of Tumours". Eds. Doiron, D. R., Gomer., C. J. Alan Liss, New York, 211, 1984.
5. Razum, N., Balchum, O. J., Profio, A. E., Carstens, C. *Photochem Photobiol* 46, 925, 1987.
6. Kessel, D., Morgan, A. R., Garbo, G. M., *Photochem. Photobiol.*, 54(2), 193, 1991.
7. Ginevra, F., Biffanti, S., Pagnan, A., Biolo, R., Reddi, E., Jori, G., *Cancer Letters*, 49, 59, 1990.
8. Aveline, B., Hasan, T., Redmond, R. W., *Photochem. Photobiol.*, 59(3), 328, 1994.
9. Bonnett, R., White, R. D., Winfield, U., Berenbaum, M. C., *Biochem. J.*, 261, 277, 1989.

SUMMARY OF THE INVENTION

It is an object of the present invention to provide pyrrolic compounds that absorb light at long wavelengths for use in photodynamic therapy and diagnosis of disease states.

It is another object to provide a reaction product of (A) P where P is a pyrrolic derivative and (B) $In^{113}X_3$ and/or $In^{115}X_3$ (where X is a charge balancing ion, either organic or inorganic) such as to provide the reaction product (C) $PIn^{113}{}_nX_n$ and/or $PIn^{115}{}_nX_n$, where indium is coordinated to the pyrrolic derivative and n=1, 2, 3.

It is yet another object of the invention to provide a reaction product of (C) $PIn^{113}{}_nX_n$ and/or $PIn^{115}{}_nX_n$ with a neucleophile Y, such that a reaction product (D) $PIn^{113}{}_nY_nX_z$ and/or $PIn^{115}{}_nY_nX_z$ is obtained (where Y is a charge balancing ion, either organic or inorganic n=1,2,3 and z=0, 1, 2, 3).

It is still another object to provide compounds $PIn^{113}X$ and/or $PIn^{115}X$ that may be used to treat diseases such as atherosclerosis, restenosis, cancer, cancer pre-cursors, non-cancerous hyperproliferating diseases, psoriasis, macular degeneration, glaucoma and viruses, benign prostate hyperplasia, rheumatoid arthritis and to aid in the diagnosis of these disease states.

DESCRIPTION OF THE PREFERRED EMBODIMENTS

Figure 1:
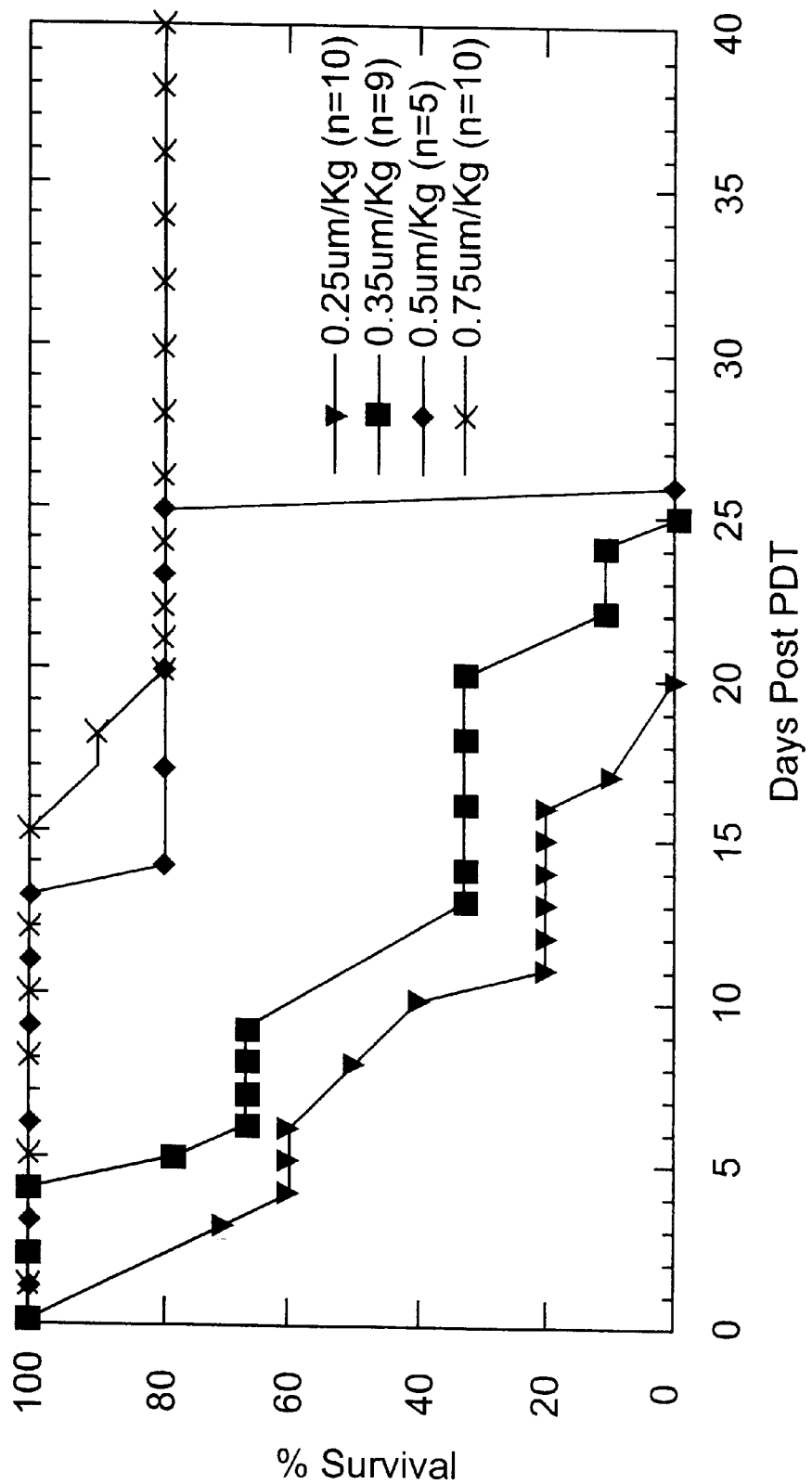
FIG. 1 is a Kaplan-Meier survival curve for tin octaethylbenzochlorin.

The present invention provides derivatives of photoactivatable compounds, some of which are shown in the following Examples, in Table 1, and in FIGS. 1–5 via the introduction of non-radioactive indium into the macrocycle. The resulting products can be used to diagnose and treat disease states. Additionally, the ligand on the indium complex may then be further chemically or biochemically modified ex-vivo or in-vivo to form a different pyrrolic indium complex which is capable of binding to important blood plasma components or cell transport proteins that enhance sensitizer uptake at the diseased tissue site.

Additional functionality around the pyrrolic structure can be used to attach biomolecules, examples of which may be antibodies, growth hormones and growth factors or other disease specific molecules, or to aid such factors as water solubility, lipophilicity or hydrophobicity which are known factors that influence drug uptake in tumor disease tissue.

The following Examples are presented solely for the purpose of disclosing and illustrating the invention, and are not to be construed as limiting. In all of the procedures described in the examples, indium, where used, was the natural material, a mixture of about 4.23% $In^{113}$ and 95.77% $In^{115}$. The following abbreviations are used in the examples: mL means milliliter or milliliters, g means gram or grams; mg means milligram or milligrams; μg means microgram or micrograms.

EXAMPLE 1

Preparation of Indium Methyl pyropheophorbide from methyl pyropheophorbide

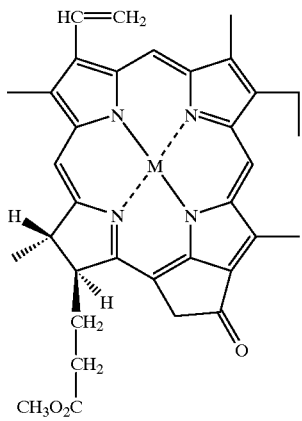

Methyl pyropheophorbide (0.5 g) was dissolved in acetic acid (100 mL); Indium chloride (0.5 g) and anhydrous sodium acetate (0.5 g) were added, and the solution was refluxed for 3 hrs. The solution was taken to dryness by rotary evaporation and the solid residue dissolved in dichloromethane/water (100 mL/100 mL). The organic layer was washed several times with 0.5 N HCl/water (200 mL), collected and dried over anhydrous sodium sulfate (20 g). The organic layer was filtered and evaporated to dryness. The resulting residue was crystallized from methanol/dichloromethane. Yield 0.45 g.

EXAMPLE 2

Preparation of Indium tert-butyl phthalocyanine

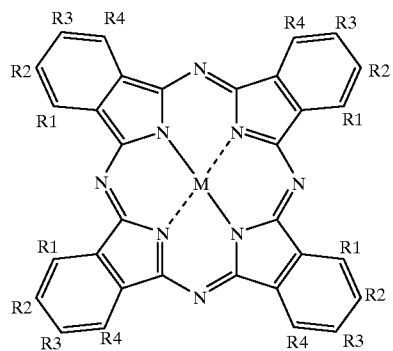

one of R2 and R3 is tert-butyl while the other and R1 and R4 are H; and M is $In^{113}Cl$, $In^{115}Cl$ or a mixture of $In^{113}Cl$ and $In^{115}Cl$.

4tert-butyl-1,2-dicyanobenzene (2 g) and Indium chloride (2.0 g) were mixed thoroughly in a round bottom flask with stirring. The mixture was heated at 160° C. for 2 hrs and the reaction vessel cooled to room temperature. The crude phthalocyanine was extracted from the resulting green solid using hot dichloroethane and the green solution evaporated by rotary evaporation. The resulting solid was dissolved in 7% acetone/dichloromethane and chromatographed on silica using 7% acetone/dichloromethane as eluent. The major green fraction was collected and recrystallized from methanol/dichloromethane. Yield, 1.1 g.

EXAMPLE 3

Preparation of Indium Benzoporphyrin derivative from Benzoporphyrin derivative dimethyl ester

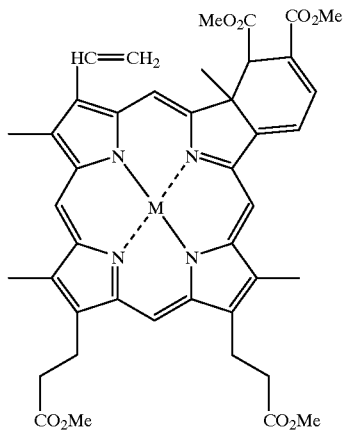

Where M is $In^{113}Cl$, $In^{115}Cl$, or a mixture of $In^{113}Cl$ and $In^{115}Cl$ in indium benzoporphyrin derivative dimethyl ester and 2H in Ring B isomer benzoporphyrin derivative dimethyl ester.

Ring B isomer, Benzoporphyrin derivative dimethyl ester (100 mg) was dissolved in acetic acid (50 mL) and Indium chloride (0.2 g) and anhydrous sodium acetate (0.2 g) were added; the solution was refluxed for 3 hrs. The solution was taken to dryness by rotary evaporation and the solid residue dissolved in dichloromethane/water (100 mL/100 mL). The organic layer was washed several times with 0.5 N HCl/water (200 mL), collected and dried over anhydrous sodium sulfate (20 g). The organic layer was filtered and evaporated to dryness. The resulting residue was chromatographed on silica using 5% MeOH/dichloromethane as eluent and the major green fraction collected. The solvent was removed by rotary evaporation and the solid crystallized from hexane/dichloromethane. Yield 50 mg.

EXAMPLE 4

Preparation of Indium m-hydroxy tetraphenylchlorin: from Tetrakis (3-hydroxyphenyl) chlorin

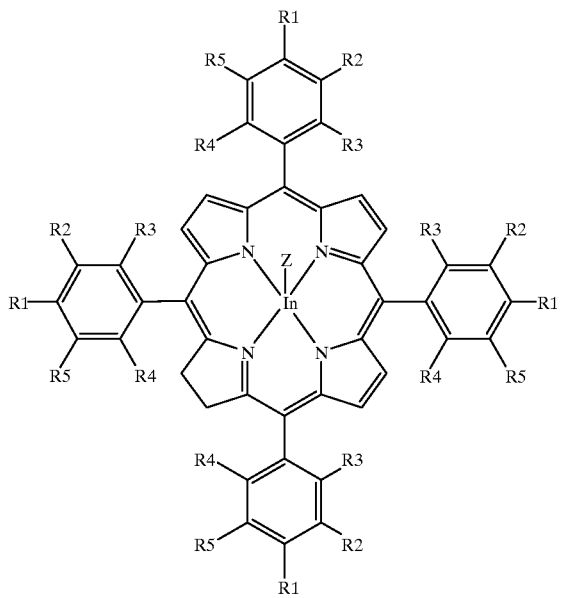

Where each R2 is OH, each R1, R3, R4 and R5 is Hydrogen, In is a mixture of $In^{113}Cl$ and $In^{115}Cl$, and Z is Cl.

Tetrakis (3-hydroxyphenyl)chlorin (100 mg) was dissolved in acetic acid and the solution purged with argon. Indium chloride (0.2 g) and anhydrous sodium acetate (0.2 g) was added and the solution refluxed for 3 hrs under argon. The solution was taken to dryness by rotary evaporation and the solid residue dissolved in dichloromethane/water (100 mL/100 mL). The organic layer was washed several times with 0.5 N HCl/water (200 mL), collected and dried over anhydrous sodium sulfate (20 g). The organic layer was filtered and evaporated to dryness. The resulting residue was chromatographed on silica using 5% MeOH/dichloromethane as eluent and the major green fraction collected. The solvent was removed by rotary evaporation and the solid crystallized from hexane/dichloromethane. Yield 60 mg.

EXAMPLE 5

Preparation of In Octaethylbenzochlorin (9) from Octaethylbenzochlorin ("OEBC")

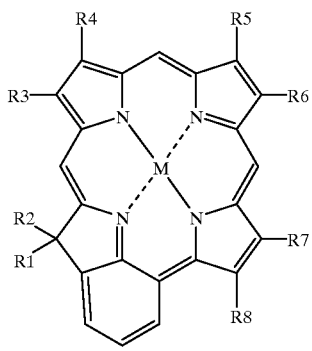

Each of R1 through R8 is ethyl, In Octaethyl benzochlorin, M is 2H, and in Indum octaethyl benzochlorin M is $In^{113}Z$, $In^{115}Z$ or a mixture of $In^{113}Z$, and $In^{115}Z$; Z is Cl.

Octaethylbenzochlorin (100 mg) was dissolved in acetic acid and Indium chloride (0.2 g) and anhydrous sodium acetate (0.2 g) were added. The solution was refluxed for 3 hrs under argon. The solution was taken to dryness by rotary evaporation and the solid residue dissolved in dichloromethane (10 mL). The resulting solution was chromatographed on silica using 5% MEOH/dichloromethane as eluent and the major green fraction collected. The solvent was removed by rotary evaporation and the solid crystallized from hexane/dichloromethane. Yield 110 mg.

EXAMPLE 6

Preparation of $InOEBCSO_2NH(CH_2)_3OH$ (10) from $OEBCSO_2NH(CH_2)_3OH$

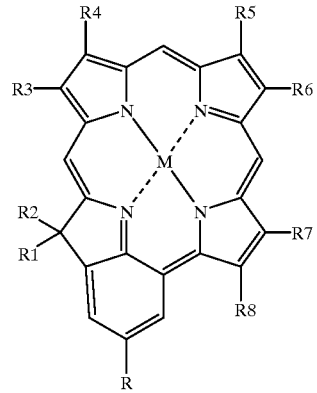

Each of R1 through R8 is ethyl In Octaethyl benzochlorin, M is 2H, and in Indium Octaethyl benzochlorin M is a mixture of $In^{113}Cl$ and $In^{115}Cl$ R is $SO_2NH(CH_2)_3OH$.

$OEBCSO_2NH(CH_2)_3OH$ (100 mg) was dissolved in dimethylformamide (DMF) (25 mL) and $InCl_3$ (100 mg) was added. The solution was refluxed for 6 hrs and the DMF was removed by rotary evaporation. The residue was dissolved in dichloromethane (10 mL) and the resulting solution was chromatographed on silica using 5% MeOH/dichloromethane as eluent. A minor fore running green band was collected and discarded and the more polar major green fraction was collected. The solvent was removed by rotary evaporation and the solid crystallized from hexane/dichloromethane. Yield 52 mg.

EXAMPLE 7

Preparation of

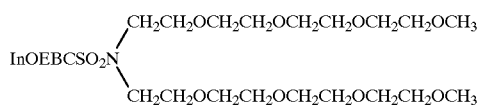

(17)

from

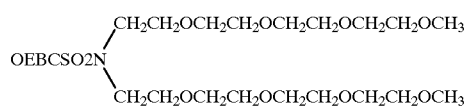

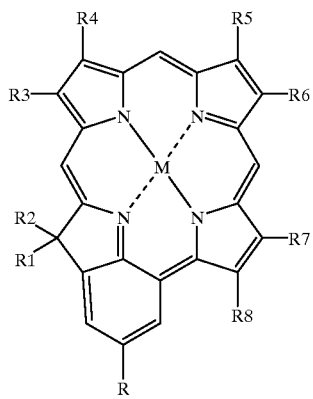

Where each of R1 through R8 is ethyl M is $In^{113}Z$, $In^{115}Z$, or a mixture of $In^{113}Z$ and $In^{115}Z$ in In Octaethyl benzochlorin and 2H in Octaethyl benzochlorin R is

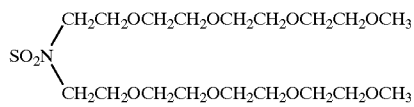

Z is Cl

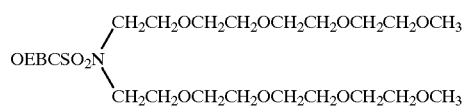

(400 mg) was dissolved in acetic acid (150 mL) and Indium chloride (0.4 g) and anhydrous sodium acetate (0.3 g) were added. The solution was refluxed for 3 hrs under argon. The solution was taken to dryness by rotary evaporation and the solid residue dissolved in dichloromethane (10 mL). The resulting solution was chromatographed on silica using 5% acetone/dichloromethane as eluent and the major green fraction collected. The solvent was removed by rotary evaporation and the solid crystallized from hexane/dichloromethane. Yield 420 mg.

EXAMPLE 8
Preparation of $InOEBCSO_2NHC(CH_2OH)_3$ (19) from OEBC $SO_2NHC(CH_2OH)_3$

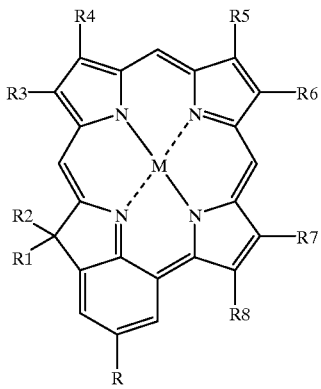

Each of R1 through R8 is ethyl In Octaethyl benzochlorin, M is 2H, and in Indium Octaethyl benzochlorin M is a mixture of $In^{113}Cl$ And $In^{115}Cl$
R is $SO_2NHC(CH_2OH)_3$.

$OEBCSO_2NHC(CH_2OH)_3$ (100 mg) was dissolved in bromobenzene (50 mL) and Indium chloride (0.2 g) and anhydrous sodium acetate (0.2 g) were added. The solution was refluxed for 5 hrs under argon. The solution was taken to dryness by rotary evaporation and the solid residue dissolved in dichloromethane (10 mL). The resulting solution was chromatographed on silica using 5% acetone/dichloromethane as eluent and the major green fraction collected. The solvent was removed by rotary evaporation and the solid crystallized from hexane/dichloromethane. Yield 105 mg.

EXAMPLE 9
Preparation of $InOEBCSO_2NH (CH_2)_4CH(NH_2)CO_2H$ (21) from $OEBCSO_2NH (CH_2)_4CH(NH_2)CO_2H$

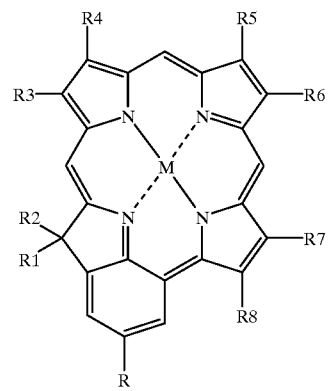

Each of R1 through R8 is ethyl In Octaethyl benzochlorin, M is 2H, and in Indium Octaethyl Benzochlorin M is a mixture of In113Cl and In115Cl
R is $SO_2NH(CH_2)_4CH(NH_2)CO_2H$.

$OEBCSO_2NH (CH_2)_4CH(NH_2)CO_2H$ (100 mg) was dissolved in acetic acid and Indium chloride (0.2 g) and anhydrous sodium acetate (0.2 g) were added. The solution refluxed for 3 hours under argon. The solution was taken to dryness by rotary evaporation and the solid residue dissolved in dichloromethane (10 mL). The resulting solution was chromatographed on silica using 5% MeOH/dichloromethane as eluent and the major green fraction collected. The solvent was removed by rotary evaporation and the solid crystallized from hexane/dichloromethane. Yield 110 mg.

EXAMPLE 10
Preparation of Indium 2-desvinyl-2-acetyl pyropheophorbide (26) from 2-desvinyl-2-acetyl pyropheophorbide (26)

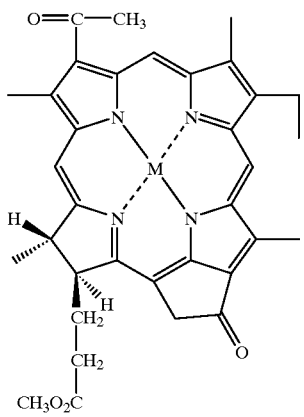

M is 2H in 2-desvinyl-2-acetyl Pyropheophorbide and a mixture of $In^{113}Cl$ and $In^{115}Cl$ in Indium-2-desvinyl-2-acetyl pyropheophorbide.

2-Desvinyl-2-acetyl pyrrpheophorbide (100 mg) was dissolved in acetic acid and Indium chloride (0.2 g) and anhydrous sodium acetate (0.2 g) were added. The solution was refluxed for 3 hrs under argon. The solution was taken to dryness by rotary evaporation and the solid residue dissolved in dichloromethane (10 mL). The resulting solution was chromatographed on silica using 5% acetone/dichloromethane as eluent and the major green fraction collected. The solvent was removed by rotary evaporation and the solid crystallized from hexane/dichloromethane. Yield 100 mg.

EXAMPLE 11

Preparation of Indium 2-desvinyl-2-formyl pyropheophorbide (27) from 2-desvinyl-2-formyl pyropheophorbide

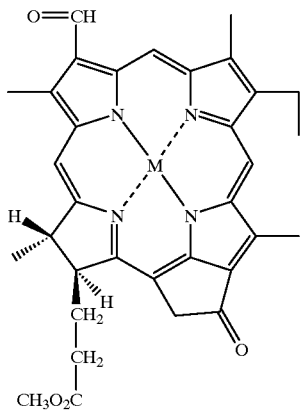

M is 2H in 2-desvinyl-2-formyl Pyropheophorbide and a mixture of $In^{113}Cl$ and $In^{115}Cl$ in Indium-2-desvinyl-2-formyl pyropheophorbide.

2-Desvinyl-2-formyl pyropheophorbide (100 mg) was dissolved in acetic acid (20 mL) and Indium chloride (100 mg) was added. Diisopropylethylamine (0.3 ml) was added and the solution refluxed until no more starting material remained by TLC (5% acetone/dichloromethane). The acetic acid was removed by rotary evaporation and the residue dissolved in dichloromethane and washed with 10% $NH_4Cl$ (2×50 mL). The organic phase was separated, dried over sodium sulfate filtered and rotoevaporated to dryness. The residue was dissolved in dichloromethane and purified by chromatography on silica using 5% acetone/dichloromethane as eluent followed by 20% acetone/dichloromethane as eluent. A less polar green fraction was collected and recrystallized from dichloromethane/hexane. A second more polar green fraction was collected and discarded. Yield of (27)=62 mg.

EXAMPLE 12

Preparation of Indium Chlorin e6 trimethyl ester (28) from Chlorin e6 trimethyl ester

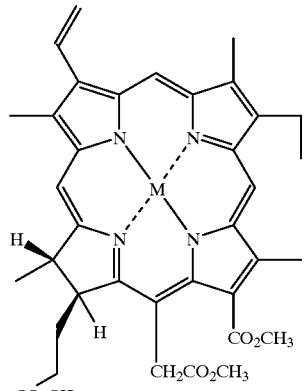

M is 2H in Chlorin e6 Trimethyl eater and a mixture of $In^{113}Cl$ and $In^{115}Cl$ in Indium-Chlorin e6 trimethyl ester Chlorin e6 trimethyl ester (150 mg) was dissolved in acetic acid (20 mL) and Indium chloride (150 mg) added. Diisopropylethylamine (0.3 ml) was added and the solution refluxed until no more starting material remained by TLC (5% acetone/dichloromethane). The acetic acid was removed by rotary evaporation and the residue dissolved in dichloromethane and washed with 10% $NH_4Cl$ (2×50 mL). The organic phase was separated, dried over sodium sulfate, filtered and rotoevaporated to dryness. The residue was dissolved in dichloromethane and purified by chromatography on silica using 5% acetone/dichloromethane as eluent followed by 20% acetone/dichloromethane as eluent. The major green fraction was collected and re-purified by chromatography on silica using 5% acetone/dichloromethane as eluent. The major green fraction was collected and recrystalized from dichloromethane/hexane. Yield, 67 mg Various compounds comprised essentially of a non-radioactive indium atom complexed with the inner nitrogens of a pyrrolic core have been evaluated biologically as photosensitizers. The results of some of this evaluation are summarized below.

In Vitro Biological Evaluation of Functionalized Benzochlorins

The in vitro biological evaluation of certain photosensitizers was determined, using standard procedures. Several of the photosensitizers had the following structure:

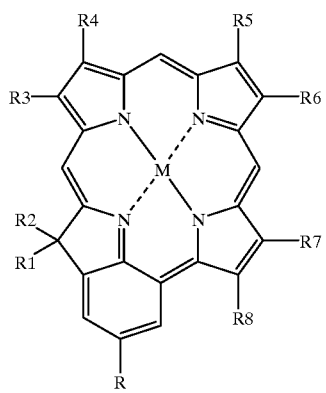

where each of R1 through R8 was ethyl and R and M had various meanings.

The identities of a first group of the compounds tested, all of which had the foregoing structure, of an arbitrary "Sensitizer Number" assigned for reference purposes, and the Example (if any) where their preparation is described are set forth below:

| Sensitizer Number | Example (if any) | Identity of M in Foregoing formula | Identity of R in Foregoing formula |
|---|---|---|---|
| 1 | | 2H | H |
| 2 | | 2H | $SO_2NH(CH_3)_2OH$ |
| 3 | | 2H | $CH_3$ |
| 4 | | Zn | H |
| 5 | | Zn | $SO_2NH(CH_3)_2OH$ |
| 6 | | Sn | H |
| 7 | | Sn | $SO_2NH(CH_3)_2OH$ |
| 8 | | Sn | $CH_3$ |
| 9 | 5 | In | H |
| 10 | 6 | In | $SO_2NH(CH_3)_2OH$ |
| 11 | | In | $CH_3$ |
| 12 | | In | $SO_2N(CH_2CH_2OH)_2$ |
| 13 | | In | $SO_2NH(CH_3)_5OH$ |
| 14 | | In | See structure below |
| 15 | | In | See structure below |
| 16 | | In | $SO_2NH(CH_2)_2O(CH_2)_2O(CH_2)_2OCH_3$ |
| 17 | 7 | In | $SO_2N[(CH_2)_2O(CH_2)_2O(CH_2)_2O(CH_2)OCH_3]_2$ |
| 18 | | In | $SO_2NH(CH_2)_3SH$ |
| 19 | 8 | In | See structure below |
| 20 | | In | $SO_2NHCH_2CO_2H$ |
| 21 | 9 | In | See structure below |

Sensitizer Number 14

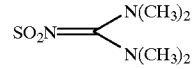

Sensitizer Number 15

Sensitizer Number 19

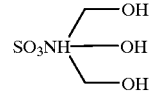

Sensitizer Number 21

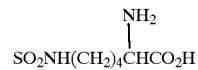

The identities of a second group of compounds tested, all of which had the following structure, of an arbitrary "Sensitizer Number" assigned for reference purposes, and the Example, (if any) where their preparation is described are set forth below:

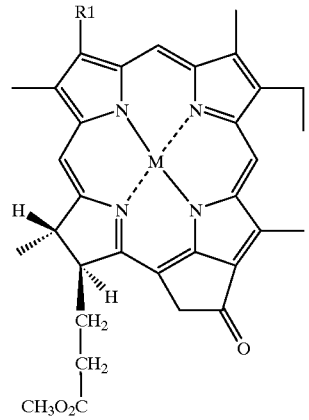

| Sensitizer Number | Example (if any) | Identity of M in foregoing formula | Identity of R1 in foregoing formula |
|---|---|---|---|
| 22 | | 2H | Vinyl |
| 23 | | $SnCl_2$ | Vinyl |
| 24 | | InCl | Vinyl |
| 25 | | InCl | Ethyl |
| 26 | 10 | InCl | $COCH_3$ |
| 27 | 11 | InCl | CHO |
| 28 | 12 | Pd | $COCH_3$ |

A third group of the sensitizers had the following formula:

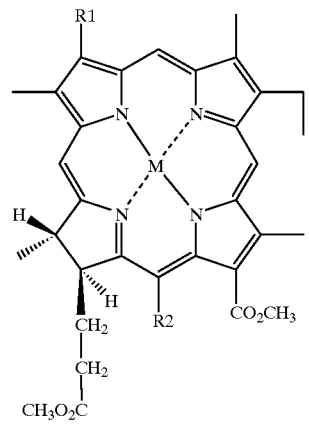

| Sensitizer Number | Example (if any) | Identity of M in foregoing formula | Identity of R1 in foregoing formula | Identity of R2 in foregoing formula |
|---|---|---|---|---|
| 29 | | a mixture of $In^{113}Cl$ and $In^{115}Cl$ | Vinyl | $CH_2CO_2CH_3$ |
| 30 | | a mixture of $In^{113}Cl$ and $In^{115}Cl$ | Ethyl | $CH_2CO_2CH_3$ |
| 31 | | a mixture of $In^{113}Cl$ and $In^{115}Cl$ | Vinyl | $CO_2CH_3$ |
| 32 | | a mixture of $In^{113}Cl$ and $In^{115}Cl$ | Ethyl | $CO_2CH_3$ |

For the Biological Evaluation, Chinese hamster lung fibroblasts (V-79) obtained from the American Tissue Culture Collection were grown in D-MEM supplemented with 10% fetal calf serum at 37° C., 5% $CO_2$, and 95% humidity. These cells were used to evaluate the sensitizers for dark and light toxicity, and cellular uptake. Medium was replaced with 5% fetal calf serum supplemented medium during sensitizer incubations.

In the first phase, the combination of intracellular and extracellular concentration of photosensitizer required for lethal damage to 50% of the cells in culture (DC(50)) on light exposure was determined by plating cells at a density of 100 cells/$cm^2$ and incubating for 1–3 hours to allow attachment of the cells. Cells were incubated with various concentrations of sensitizer ([C]=0.01–1.0 $\mu$M) delivered in non-toxic concentrations of DMSO/5% dextrose solution or in some cases in egg yolk phosphatidase (EYP) for 16–24 hours. The cells were then irradiated with laser light using a tunable Lexel argon pumped dye laser at the band I absorption of the photosensitizer. Total power density was adjusted to 12.5 mW/$cm^2$ and a total light dose of 1.25 J/$cm^2$ was applied. After treatment, cells were washed with HBSS, refed with 10% FBS supplemented DMEM with phenol red and incubated for 3–5 days to allow colony formation. Cells were fixed in methanol, stained with Giemsa, and colonies were counted. Plating efficiency was determined using a control colony and the mean percent survival fraction plotted against the sensitizer concentration and the DC50 established (Table 5).

Several photosensitizers were screened by a standard cellular uptake protocol. A 10 $\mu$M stock solution of photosensitizer in EYP was prepared by dilution of the photosensitizer stock (1 mM) using 5% dextrose solution. Monolayer V-79 cells in the log phase of growth in 12-well tissue culture plates were incubated with 0.2 mL of the 10 $\mu$M solution of photosensitizer for time periods of 0, 12, 36, 48 hrs. Following incubation the cells were washed with PBS (1 mL) three times, then washed with HBSS (1 mL) and detached using 100 $\mu$L of trypsin. Individual wells containing cells were lysed by three freeze thaws.

Spiking experiments were performed to confirm that the sensitizer could be adequately recovered using standard procedures. The sensitizer was then extracted from the cell debris with DMSO, centrifuged and the supernatant examined for fluorescence. Sensitizer concentration was determined by comparison to a standard curve. Results are expressed in ug/ug protein. Untreated monolayers are used to determine cell count. Treated cells of each time point were used to determine the protein concentration using the BCA assay. The results for the photosensitizers studied are presented in Table 2. Results shown are the mean of the three experiments for each timepoint.

As can be clearly seen for the compounds tested, indium compounds had clearly a much lower DC(50)(light) values, regardless of the functionality attached to the chlorin.

In Vivo Assay of Photosensitizers on Tumors

Female C3H/HeJ mice (8–9 weeks old) were subjected to trochar implantation of BA mammary carcinoma on the hind leg of the animals. Animals having tumors ca 5 mm in diameter were entered into the in vivo screen. For each new photosensitizer, a group of at least three mice were used to ascertain a drug dose that caused a response as described in table 3 when treated with the appropriate wavelength of light. Generally in this series, animals were injected with 1 $\mu$ mole of sensitizer/Kg of body weight, formulated in egg yolk phosphatidate (EYP), via the tail vein. At a defined time period later the animals were irradiated with light from a laser source tuned to the wavelength of activation of the sensitizer. The power density of the laser was set at 75 mW/$cm^2$ with a total light dose of 200 J/$cm^2$. The spot size was 1 cm diameter. Results for each photosensitizer are shown in Table 3.

Figure 2:
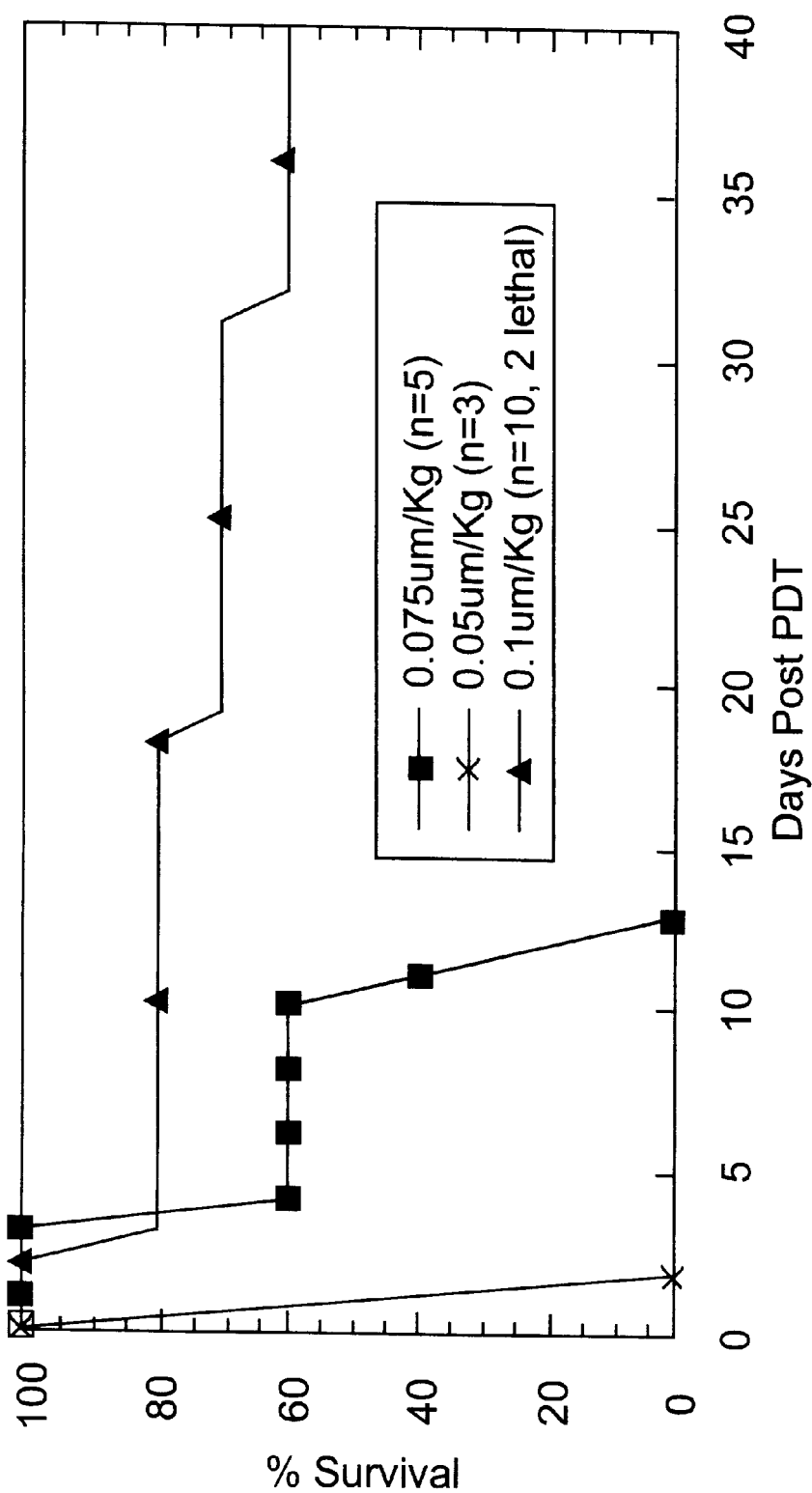
FIG. 2 is a Kaplan-Meier survival curve for indium octaethylbenzochlorin.
Figure 3:
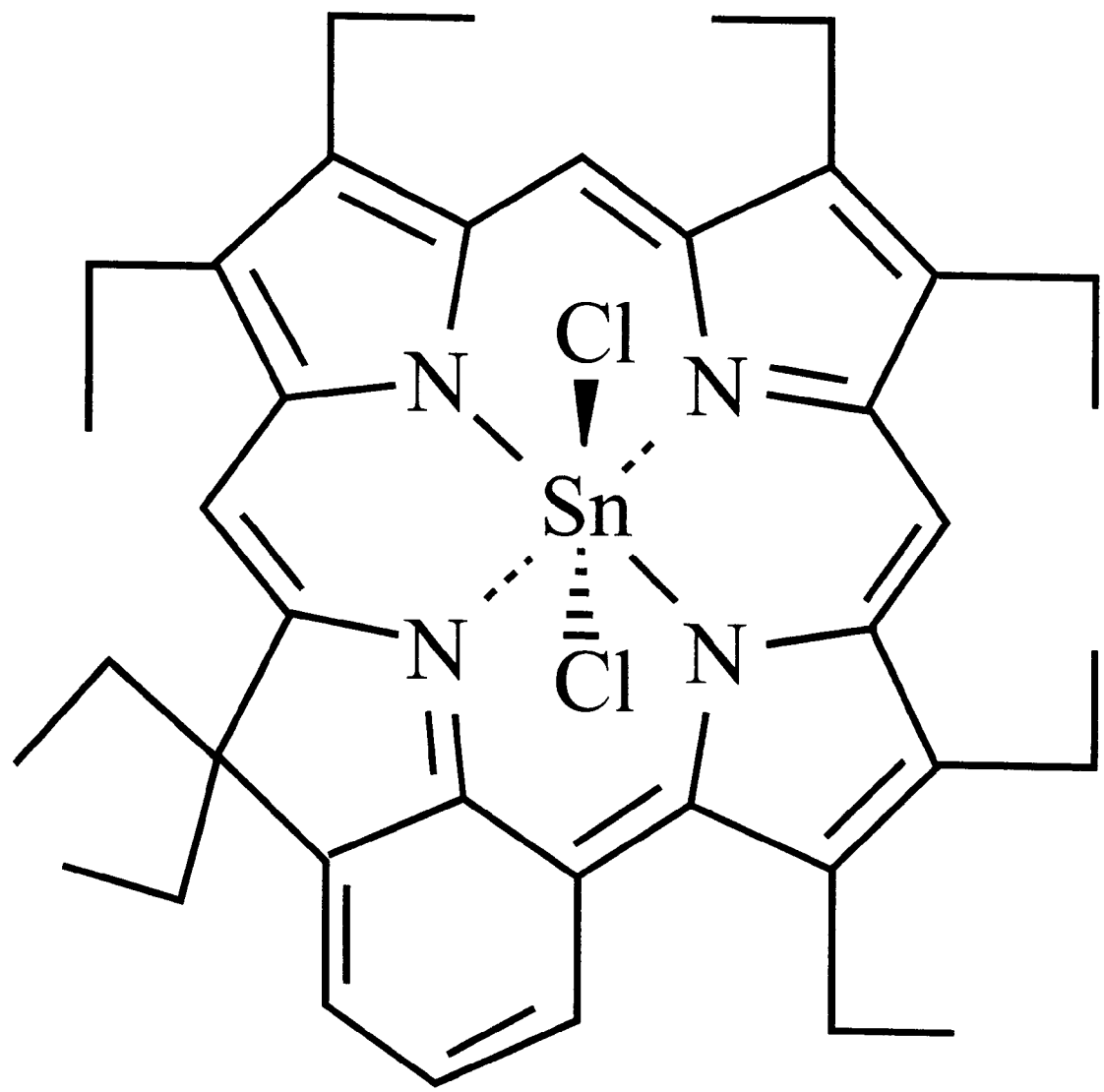
FIGS. 3 and 4 show the structures, espectively, of tin octaethylbenzochlorin and of indium octaethylbenzochlorin.
Figure 4:
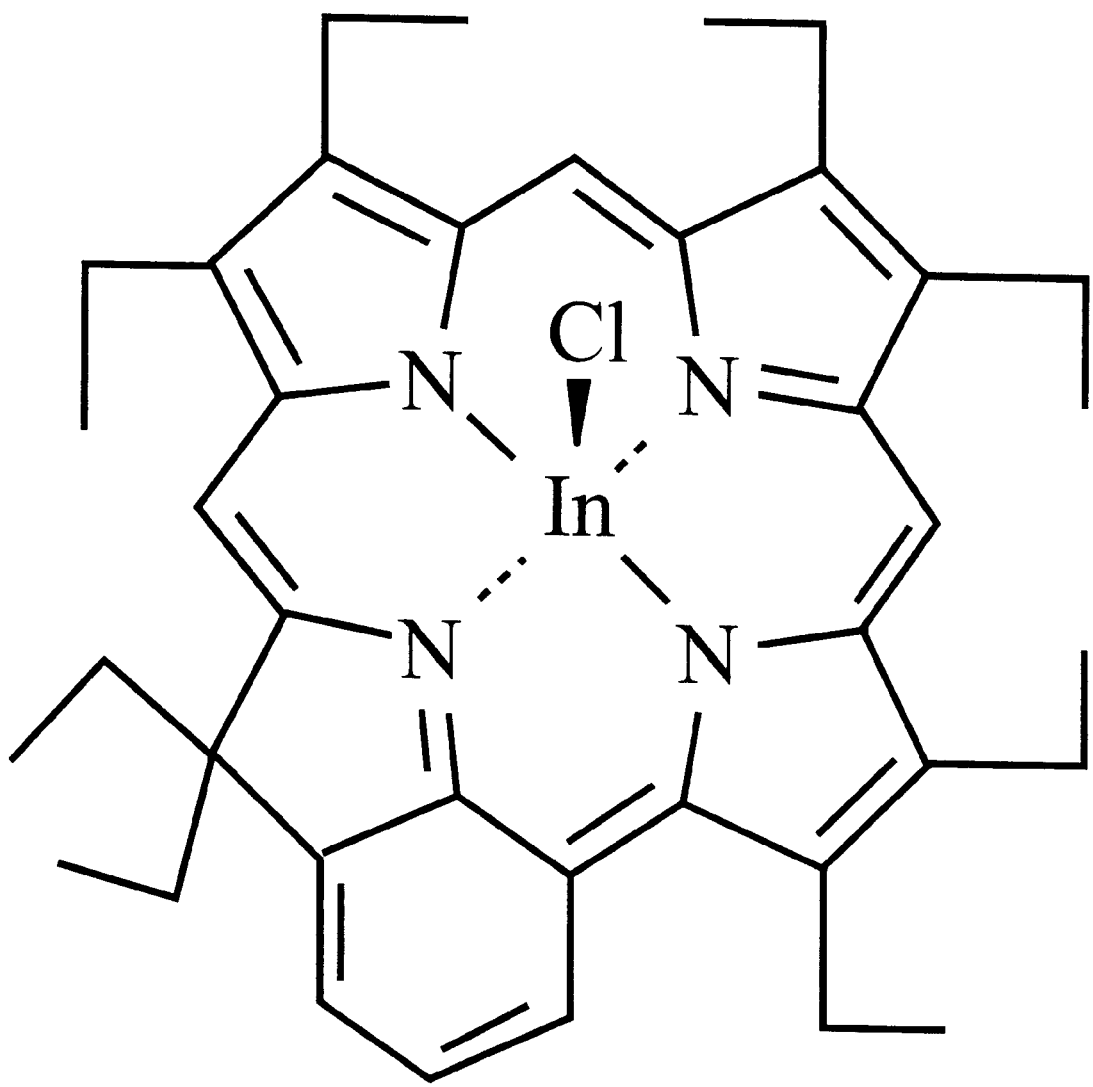
Figure 6:
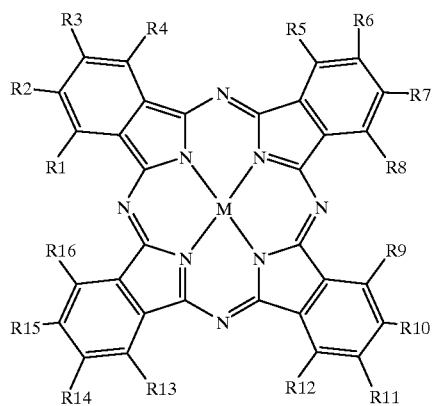
Figure 7:
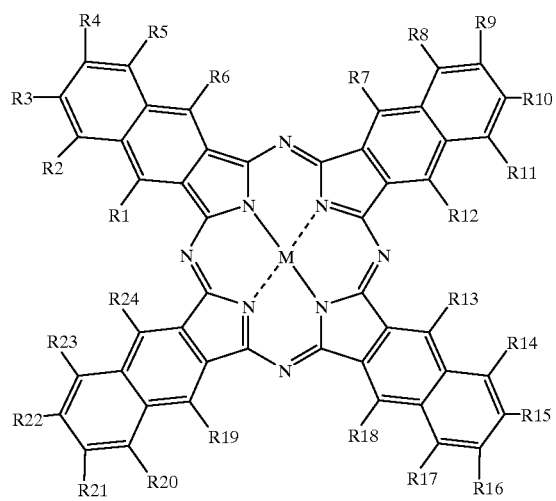

Selected Kaplan-Meier curves for two different benzochlorin metal classes are shown in FIGS. 1 and 2 of the drawings. Survival curves for SnOEBC are shown in FIG. 1, while the structure of SnOBEC is shown in FIG. 3. Survival curves for InOECB are shown in FIG. 2, while the structure of InOEBC is shown in FIG. 4.

TABLE 2

Photophysical measurements, DC(50)(light) and cellular uptake of Photosensitizers

Figure 16:
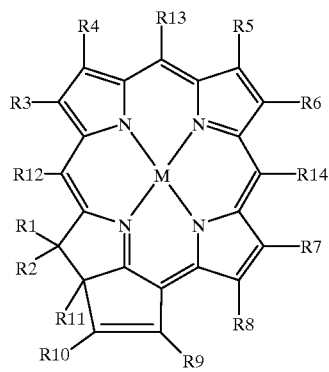
Figure 17:
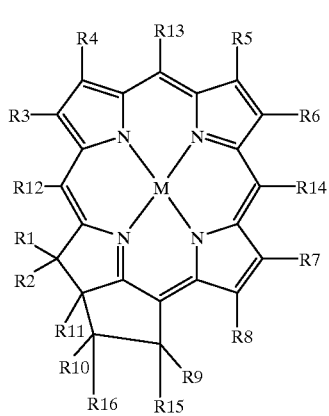
Figure 18:
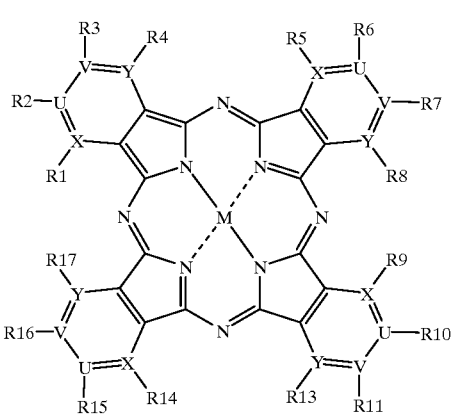
Figure 19:
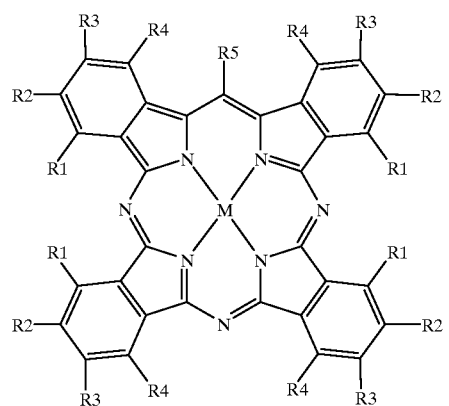
Figure 20:
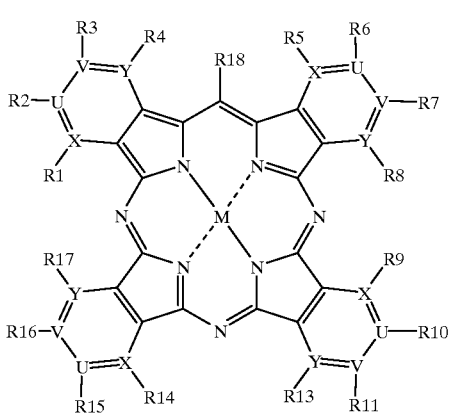
Figure 21:
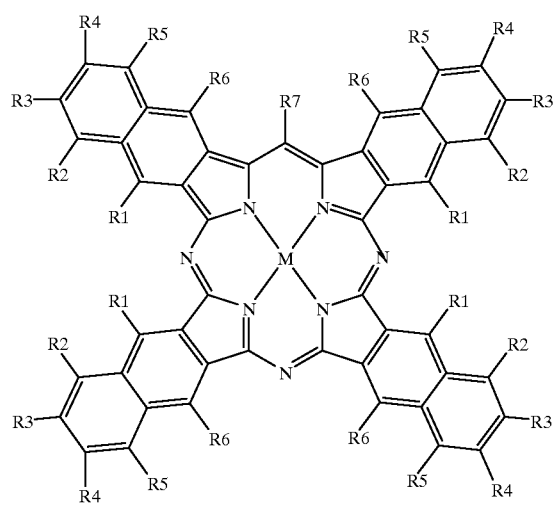
Figure 22:
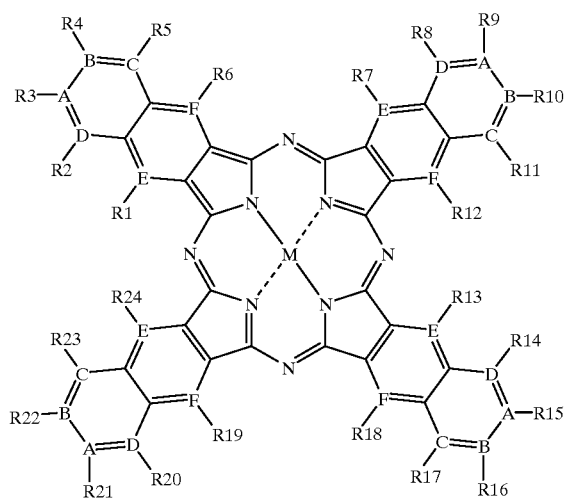
Figure 23:
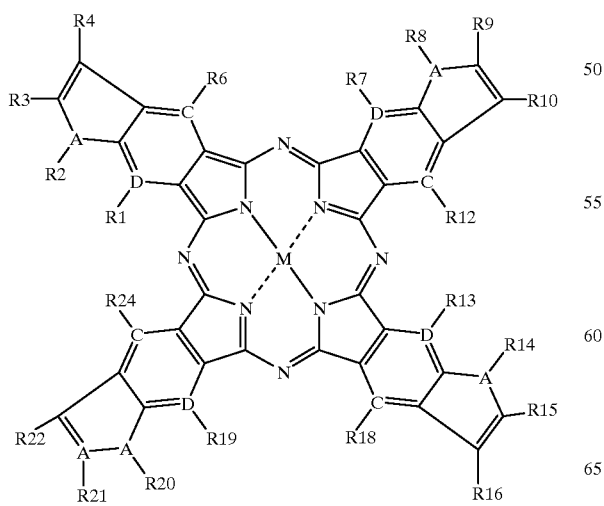
Figure 24:
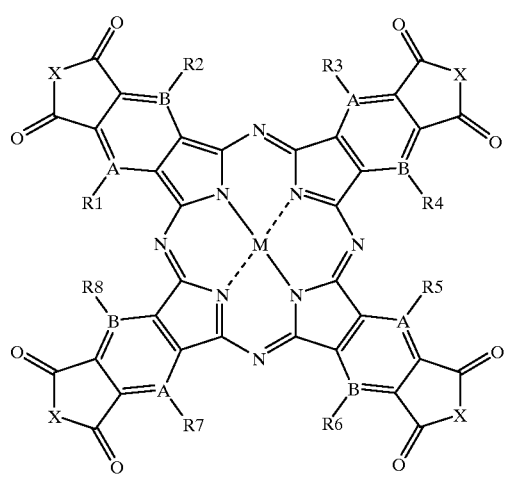
Figure 25:
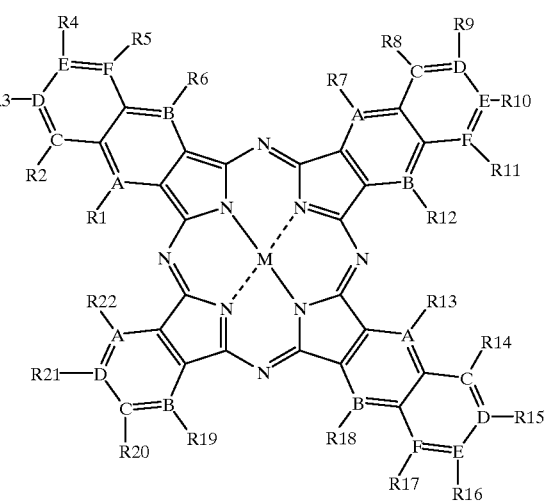
Figure 26:
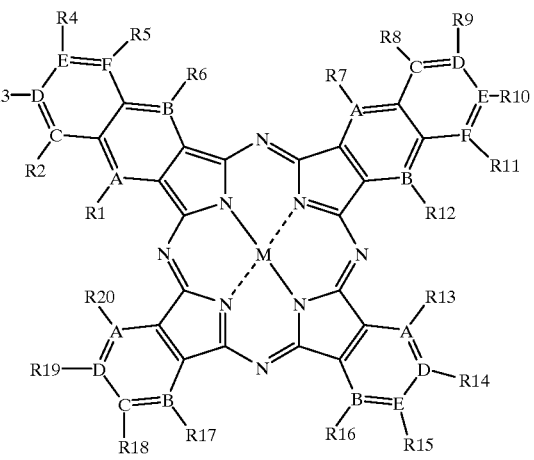
Figure 27:
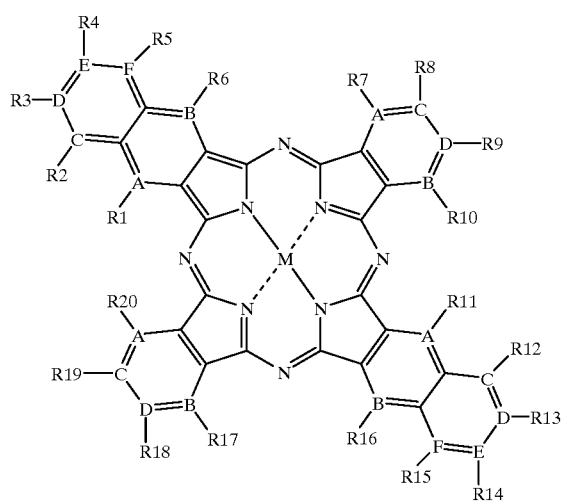
Figure 30:
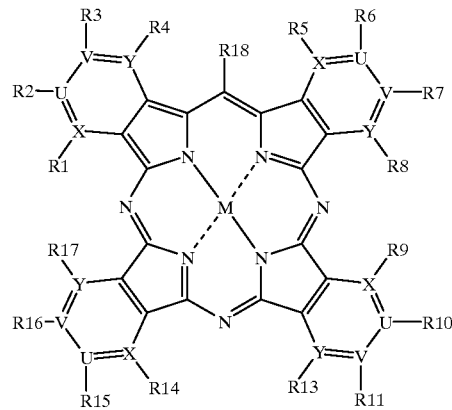
Figure 28:
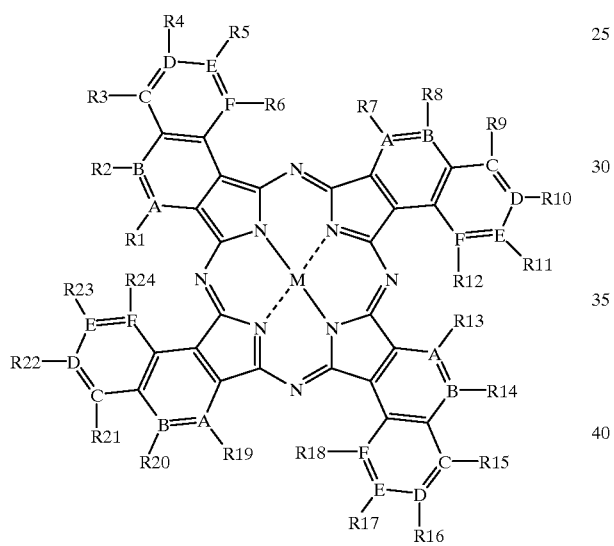
Figure 31:
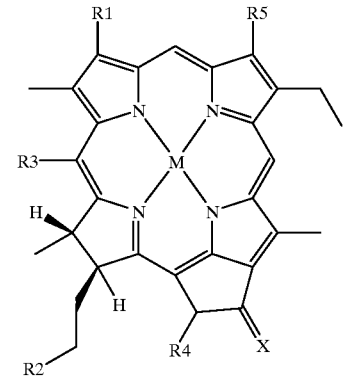
Figure 29:
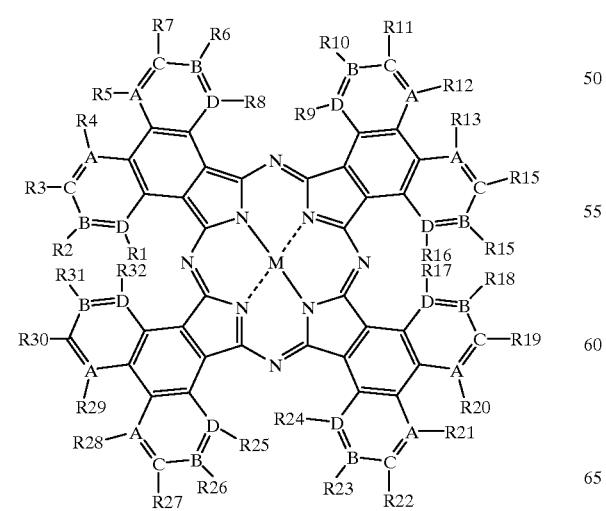
Figure 32:
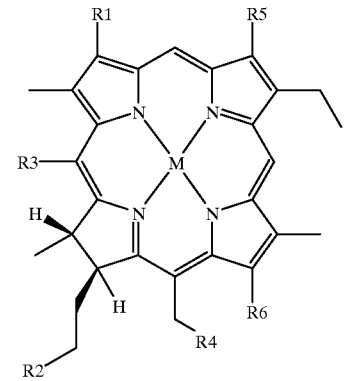
Figure 33:
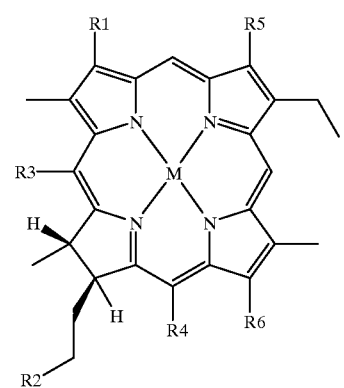
Figure 34:
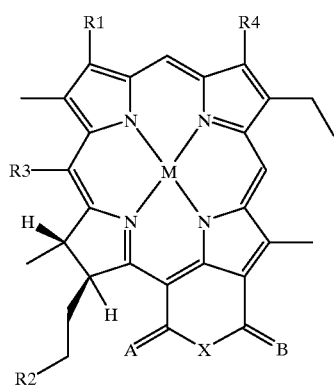
Figure 35:
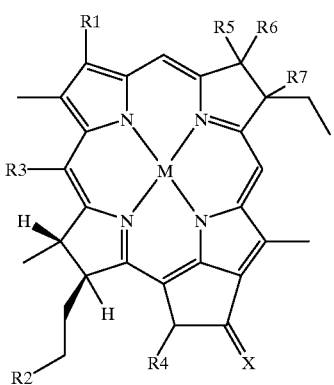
Figure 36:
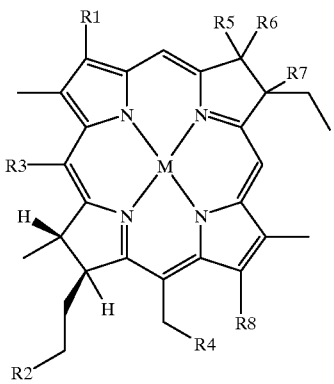
Figure 37:
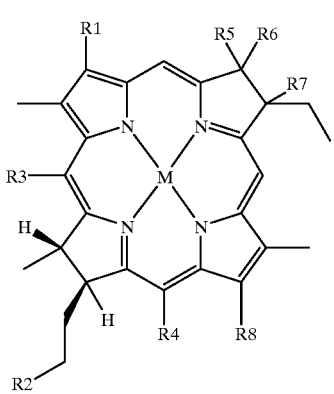
Figure 38:
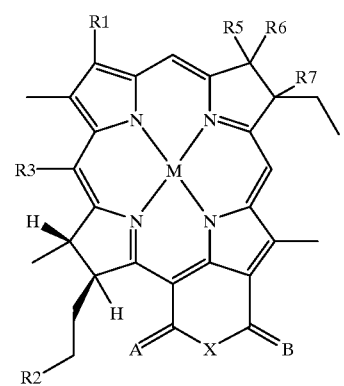
Figure 39:
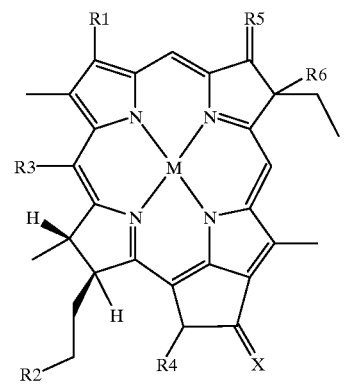
Figure 40:
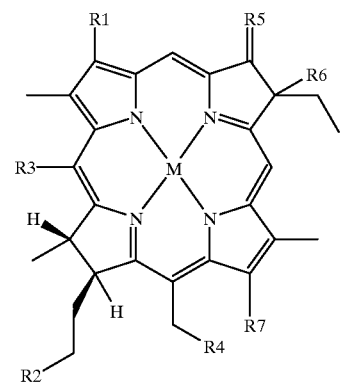
Figure 41:
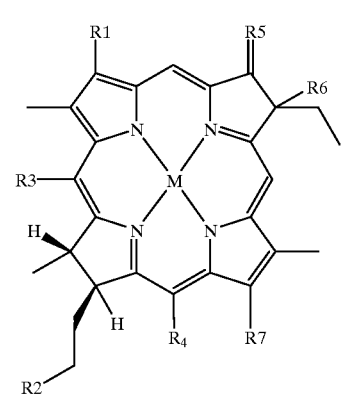
Figure 42:
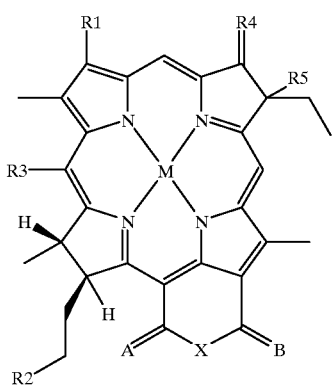
Figure 43:
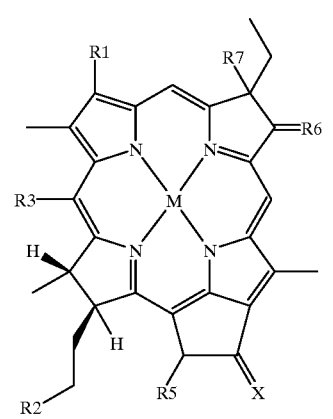
Figure 44:
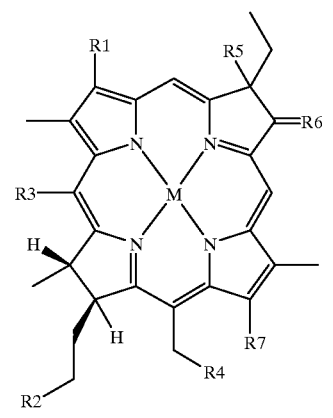
Figure 45:
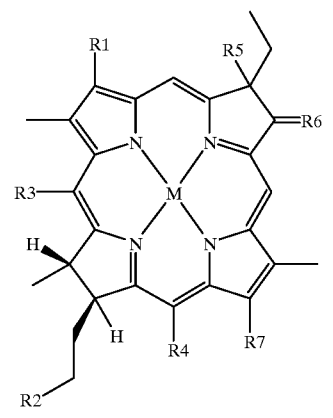
Figure 46:
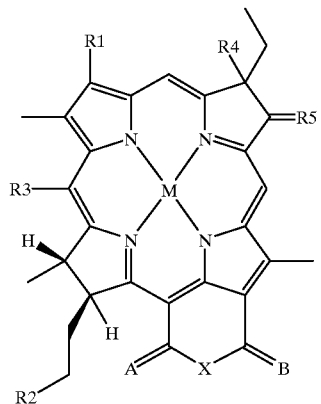
Figure 47:
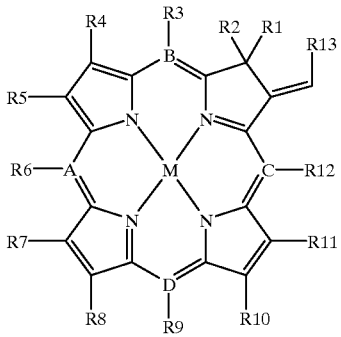
Figure 48:
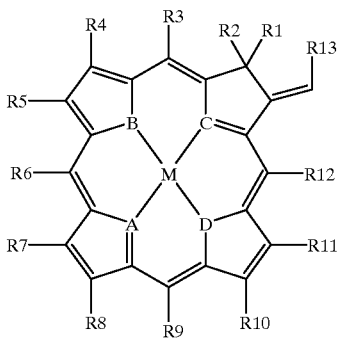
Figure 49:
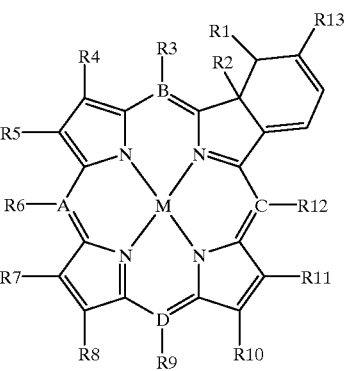
Figure 50:
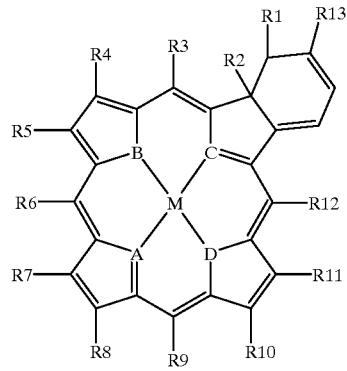
Figure 51:
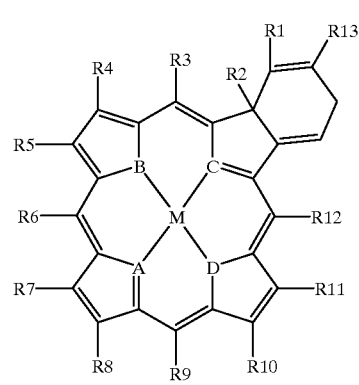
Figure 52:
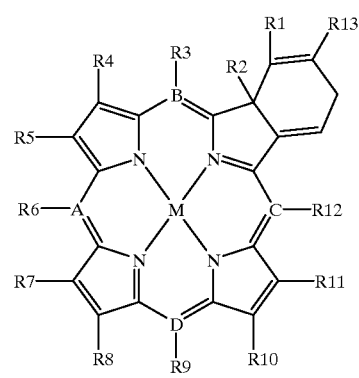
Figure 53:
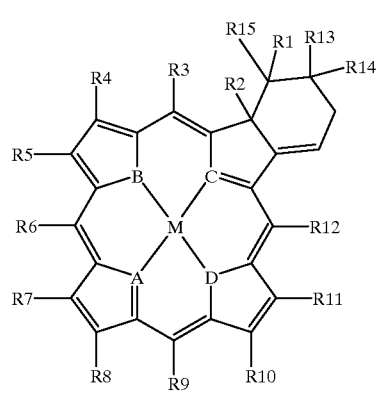
Figure 54:
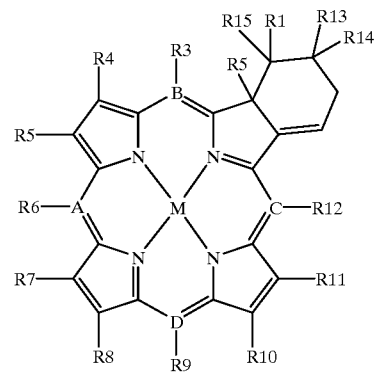
Figure 55:
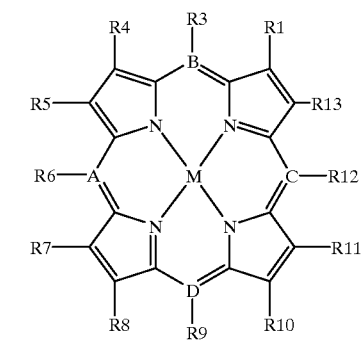
Figure 56:
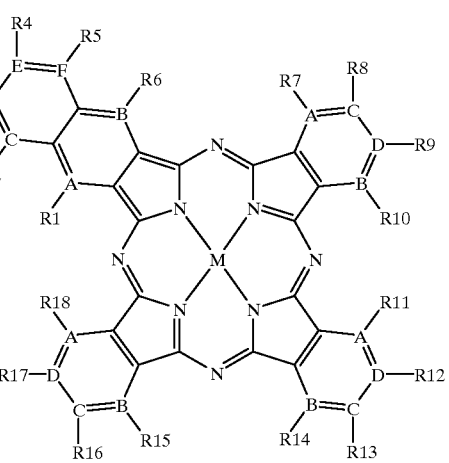

| Compound (FIG. 16) | λmax ($\epsilon$ $M^{-1}$ $cm^{-1}$) | $\phi$ f | DC (50) (light) ($\mu$M) | Cellular uptake (24 hrs) (pmole/$\mu$g protein) |
|---|---|---|---|---|
| (1) H2 | 658 (35,000) | 0.347 | >1.0 | — |
| (4) Zn | 678 (57,000) | 0.150 | >1.0 | — |
| (6) Sn | 691 (54,000) | 0.044 | 0.08–0.16 | 0.501 |
| (9) In | 691 (53,000) | 0.028 | 0.1 | 0.336 |
| (2) H2 | 665 (34,000) | 0.230 | 0.5–1.0 | 0.129 |
| (5) Zn | 678 (48,000) | 0.124 | 0.5–1.0 | 0.093 |
| (7) Sn | 684 (52,000) | 0.040 | 0.5–1.0 | — |
| (10) In | 684 (52,000) | 0.027 | 0.1–0.125 | — |
| (3) H2 | 658 (35,000) | 0.35 | — | — |
| (8) Sn | 694 (50,000) | 0.02 | — | — |
| (11) In | 687 (54,000) | 0.034 | — | — |
| (12) In | 684 (52,000) | ~0.03 | 0.04 | — |
| (13) In | 684 (52,000) | ~0.03 | 0.04 | — |
| (14) In | 684 (52,000) | ~0.03 | 0.05 | — |
| (15) In | 684 (52,000) | ~0.03 | 0.05 | — |
| (16) In | 684 (52,000) | ~0.03 | 0.04 | — |
| (17) In | 684 (52,000) | ~0.03 | 0.04 | — |
| (18) In | 684 (52,000) | ~0.03 | 0.04 | — |
| (19) In | 684 (52,000) | ~0.03 | 0.04 | — |
| (20) In | 684 (52,000) | ~0.03 | 0.04 | — |
| (21) In | 684 (52,000) | ~0.03 | 0.04 | — |
| (22) H2 | 666 (45,000) | — | — | — |
| (23) Sn | 658 (74,000) | — | >1.0 | — |
| (24) In | 666 (45,000) | — | — | — |
| (25) In | 655 | — | 0.03 | — |
| (26) In | 672 | — | 0.06 | — |
| (27) In | 683 | — | 0.05 | — |
| (28) Pd | 653 | — | 0.05 | — |
| (29) In | 641 | — | 0.05 | — |
| (30) In | 637 | — | 0.06 | — |
| (31) In | 650 | — | 0.08 | — |
| (32) In | 642 | — | 0.07 | — |

TABLE 3

Tumor cure rates for free base, Zinc, Tin and Indium Chlorins

| Compounds (FIG. 16) (M) | Drug Dose ($\mu$m/Kg) | Time of Treatment Post injection | Light Dose | % Cure (30 days) n = 10 |
|---|---|---|---|---|
| (1) H2 | 3 | 24 | 200 | 60% |
| (4) Zn | 3 | 24 | 200 | 0% |
| (6) Sn | 0.75 | 24 | 200 | 80% |
| (9) In | 0.1 | 24 | 200 | 70% |
| (2) H2 | 2.5 | 24 | 200 | 80% |
| (5) Zn | 2.25 | 24 | 200 | 100% |
| (7) Sn | 1.5 | 24 | 200 | 0% |
| (10) In | 0.1 | 24 | 200 | 100% |
| (3) H2 | 2.5 | 24 | 200 | 60% |
| (8) Sn | 1.0 | 24 | 200 | 100% |
| (11) In | 0.15 | 24 | 200 | 90% |
| (22) H2 | 10.6 | 3 | 200 | 50% |
| (23) Sn | 2.0 | 24 or 6 | 200 | 0% |
| (24) In | 0.2 | 6 or 8 | 200 | 80% |
| (12) In | 0.05 | 24 | 200 | 90% |
| (13) In | 0.075 | 24 | 200 | 80% |

TABLE 3-continued

Tumor cure rates for free base, Zinc, Tin and Indium Chlorins

| Compounds (FIG. 16) (M) | Drug Dose (μm/Kg) | Time of Treatment Post injection | Light Dose | % Cure (30 days) n = 10 |
|---|---|---|---|---|
| (14) In | 0.075 | 24 | 200 | 90% |
| (15) In | 0.05 | 24 | 200 | 100% |
| (16) In | 0.05 | 24 | 200 | 80% |
| (17) In | 0.075 | 6 | 200 | 100% |
| (25) In | 0.075 | 6 or 8 | 200 | 80% |
| (26) In | 0.125 | 8 | 200 | 90% |
| (27) In | 0.1 | 8 | 200 | 90% |
| (28) Pd | 0.2 | 8 | 200 | 80% |
| (29) In | 0.15 | 6 | 200 | 70% |

The procedures of Examples 1–12 can be modified to produce other phototherapeutic compositions according to the invention, each such composition being comprised essentially of a non-radioactive indium atom complexed with the inner nitrogens of a pyrrolic core composed of at least two pyrroles. The modification involves merely substituting an equivalent amount of the free base of another compound having a pyrrolic core composed of at least two pyrroles for the methyl pyropheophorbide, the benzoporphyrin derivative, the tetrakis (3-hydroxyphenyl)chlorin, the octaethylbenzochlorin of Examples 1, 3, 4, 5, and 6 or for the corresponding starting materials of Examples 7–12, or by substituting other dicyano compounds capable of forming functionalized phthalocyanines, functionalized naphthocyanines or the like for the 4-tertbutyl-1,2-dicyano benzene of Example 2.

Examples of compounds having a pyrrolic core composed of at least two pyrroles, and which can be substituted as described in the preceding paragraph to produce additional compounds according to the instant invention are named in Table 1, and defined by reference to FIGS. 1–58, which follow the Table.

Table 1

Pyrrole-derived macrocyclic compounds (FIG. 1).

Naturally occurring or synthetic porphyrins and derivatives thereof (FIG. 2)

Naturally occurring or synthetic chlorins and derivatives thereof (FIGS. 3, 16, 17, 32–35 and 48–55)

Bacteriochlorins and isobacteriochlorins (FIGS. 4, 5 and 36–47))

Phthalocyanines, Naphthalocyanines and derivatives thereof (FIGS. 6, 7, 15, 18–21, 24, 26, 29, 30, 31 and 56)

Figure 8:
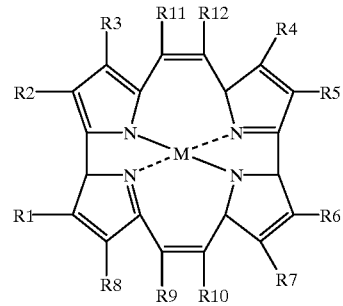

Porphycenes and derivatives thereof (FIG. 8)

Figure 9:
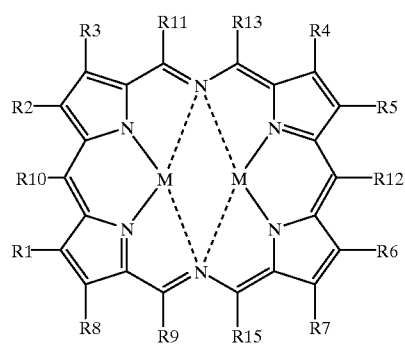

Porphycyanines and derivatives thereof (FIG. 9)

Figure 10:
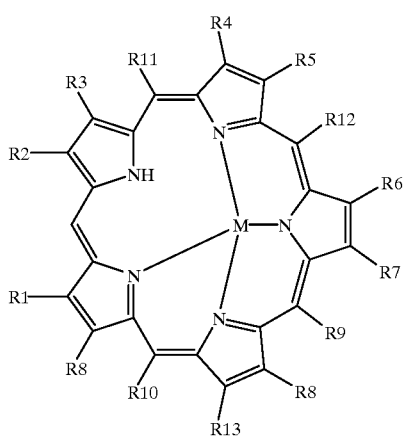
Figure 11:
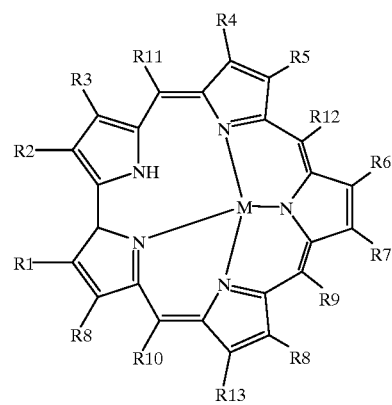

Pentaphyrins, sapphyrins and derivatives thereof (FIGS. 10 and 11)

Figure 12:
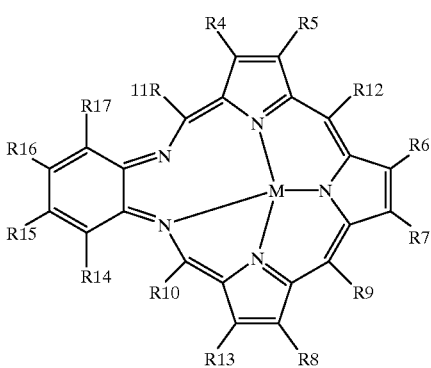

Texaphyrins and derivatives thereof (FIG. 12)

Figure 13:
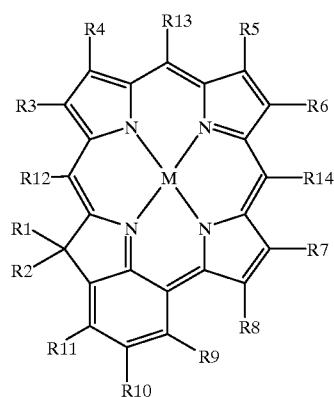

Benzochlorins and derivatives thereof (FIG. 13)

Figure 14:
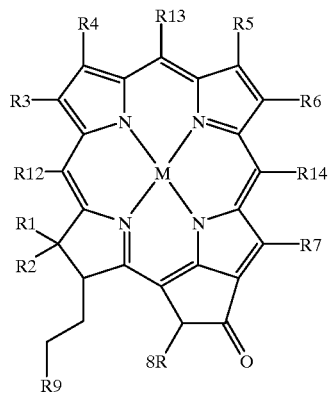
Figure 15:
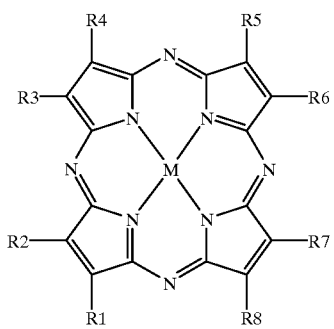

Chlorophylls and derivatives thereof (FIG. 14)

Corroles (FIG. 58)

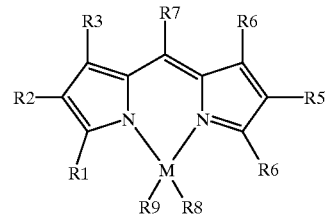

FIG. 1

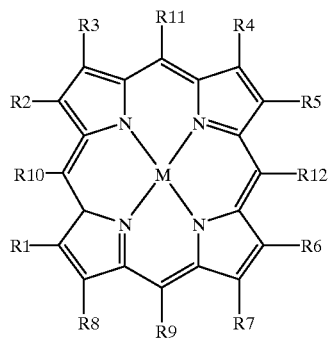

FIG. 2

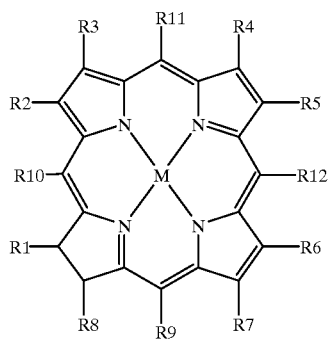

FIG. 3

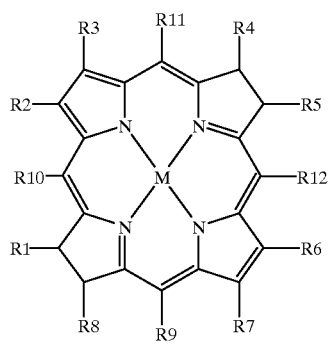

FIG. 4

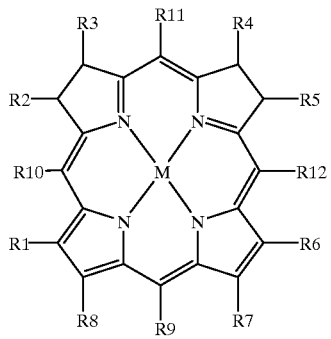

FIG. 5

Figure 57:
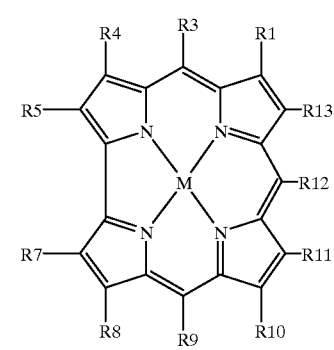

Examples and illustrations from the literature outlined in Table 1 and FIGS. 1 to 57 of types of photosensitizers that may be used in photodynamic therapy or imaging and are applicable to the insertion of indium into the central core are as follows:

Dipyrromethenes: (FIG. 1).

Dipyrromethenes have been used widely as intermediates in the synthesis of porphyrins (for example "The Porphyrins" Ed. D. Dolphin, Academic Press, 1978, Volume II 215–223; Volume I Chapter IV, 101–234. References within these volumes provide actual experimental details. These compounds can be coordinated with metal salts to produce metallo complexes (for example A. W. Johnson, I. T. Kay, R. Price, K. B. Shaw, J. Chem. Soc, Perkin Trans I, 3416–3424, 1959; S. M. Bloom, P. P. Garcia; J.H. Boyer, L. R. Morgan U.S. Pat. No. 5,189,029; date of patent Feb. 23, 1993; L. R. Morgan, J. H. Boyer, U.S Pat. No. 5,446,157). As shown in FIG. 1, these molecules can be synthesized such that a wide variety of functionality can be directly attached to the basic diyrromethene ring structure. Such functionality can be used to increase water solubility, lippophilicity, conjugation to biomolecules such as antibodies or proteins, to increase the wavelength of absorption of the molecules (by increasing the conjugation of the macrocycle). As such, these molecules can be used for light activated photochemistry or diagnosis.

Porphyrins: (FIG. 2)

Routes to the synthesis of the ubiquitous tetrapyrrolic macrocycles that contain in their macrocyclic ring system 11 double bonds (excluding peripheral substituents), is outlined in detail in several books including "Porphyrins and Metalloporphyrins" Ed. K. M. Smith, Elsevier Publishing Company, New York, 1975, Chapter 2, p29–55; chapter 19, p778–785 and "The Porphyrins" Ed. D. Dolphin, Academic Press, 1978, Volume I. References within these volumes provide actual experimental details. A very large number of porphyrinic compounds have been synthesized. As they are prevalent in nature, a large number of studies on the chemical modification of these compounds have been undertaken ("The Porphyrins" Ed. D. Dolphin, Academic Press, 1978, Volume I, p 289–339.). A great deal of work has been undertaken on the synthesis of porphyrins from monopyrrols ("The Porphyrins" Ed. D. Dolphin, Academic Press, 1978, Volume I chapter 3, 85–100; chapter 4, 101–234, chapter 5, 235–264; chapter 6, 265–288). Notable valuable examples of such work is in the synthesis of mono, di, tri and tetraphenyl porphyrins ("The Porphyrins" Ed. D. Dolphin, Academic Press, 1978, Volume I, chapter 3, 88–90; Gunter, M. J., Mander, L. N., J. Org. Chem. 46,4792–4795, 1981.). Such compounds can be widely functionalized as the aromatic rings may possess different substituents or have incorporated in them heteroatoms. Porphyrins also can be synthesized that possess annelated aromatic rings on the β-pyrrole positions (T. D. Lash, C. Wijesinghe, A. T. Osuma, J. R. Patel, Tetrahedron Letters, 38(12), 2031–2034, 1997.) which can have the effect of extending conjugation and modifying the absorption and photophysical properties of the compounds. Porphyrin type compounds have been synthesized from pyrroles and 5-membered ring heterocycles (such as thiophenes or furans for example) which incorporates one or more heteroatom besides nitrogen within the central porphyrin "core" ("Porphyrins and Metalloporphyrins" Ed. K. M. Smith, Elsevier Publishing Company, New York, 1975, Chapter 18, 729–732). Such compounds can be modified similarly to produce highly functionalized derivatives. In addition porphyrin dimers, trimers or oligomers have been synthesized with great abandon. (H. Meier, Y. Kobuke, S. Kugimiya, J. Chem. Soc. Chem. Commun., 923, 1989; G. M. Dubowchik, A. D. Hamilton, J. Chem. Soc. Chem. Commun., 904, 1985; R. K. Pandey, F- Y. Shaiu, C. J. Medforth, T. J. Dougherty, K. M. Smith, Tetrahedron Letters, 31, 7399, 1990; D. R. arnold, L. J. Nitschinsk, Tetrahedron Letters, 48, 8781, 1992; J. L. Sessler, S. Piering, Tetrahedron Letters, 28, 6569, 1987; A. Osaku, F. Kobayashi, K. Maruyama, Bull. Chem. Soc. Jpn, 64, 1213, 1991).

Chlorins: (FIGS. 3, 16, 17, 31–34, 47–54)

Chlorins or Hydroporphyrins are porphyrins that have only 10 double bonds in their macrocyclic ring system (excluding peripheral substituents). The "reduction" of the porphyrin macrocycle has pronounced effects on both the absorption profile of the macrocycle and the photophysical properties of the compound. Many naturally occurring chlorins may be extracted from plants, seaweeds or algae (e.g. "Porphyrins and Metalloporphyrins" Ed. K. M. Smith, Elsevier Publishing Company, New York, 1975, Section H, p774–778.) and simple chemical modifications to pheophorbide can give pyrropheophorbides, chlorin e6, purpurin 18 and other chlorin ring systems. Routes to the synthesis of chlorin macrocycles are outlined in "Porphyrins and Metalloporphyrins" Ed. K. M. Smith, Elsevier Publishing Company, New York, 1975, Chapter 2, p61–116; Chapter 19, 774–778, "The Porphyrins" Ed. D. Dolphin, Academic Press, 1978, Volume II, p1–37, p131–143. References within these volumes provide actual experimental details. Considerable research has been directed toward the synthesis of chlorin derivatives from porphyrins. Catalytic hydrogenation and hydroboration (H. H. Inhoffen, J. W. Buchler, R. Thomas, Tetrahedon Letters, 1145, 1969;.), diimide reductions (H. W. Whitlock Jr., R Hanauer, R., Oester, m. Y., B. K. Bower, J. Am. Chem. Soc. 91, 7585, 1969), osmium tetroxide (R. Bonnett, A. N. Nizhnick, M. C. Berenbaum, J. Chem. Soc. Chem. Comm., 1822, 1989) and hydrogen peroxide (C, K, Chang, Biochemistry, 19, 1971, 1971.), alkali metals and electrochemical reduction (N. S. Hush, J. R. Rowlands, J. Am. Chem. Soc., 89, 2976. 1967), aromatic radicals (G. L. Closs, L. E. Closs, J. Am. Chem. Soc, 85, 818, 1963) have all been successful at producing chlorins from porphyrins. The use of light as a reductive tool has also been extensively studied by several authors. The reaction of singlet oxygen on vinyl porphyrin has been used extensively to produce chlorins (H. H. Inhoffen, H. Brockman, K. M. Bleisnerv, Ann. Chem. 730, 173, 1969; D. Brault, C. Vever-Bizet, Mougee, C., Bensasson, R., Photochem. Photobiol., 47 151, 1988). The reduction of free base and metalloporphyrins with light and and reducing agents (such as amines or ascorbates) (Y. Harel, J. Manassen, J. Am. Chem. Soc., 100, 6228. 1977, J. H. Fuhrhop, T. Lumbantobing, Tetrahedron Letters, 2815, 1970; D. G. Whitten, J. C., Yau., F. A. Carol, J. Am. Chem. Soc., 93, 2291, 1971.) also produces chlorins. Cyclization of meso-acrylate containing porphyrins has been used extensively to produce purpurin derivatives (FIGS. 16 and 17) (A. R. Morgan, N. C. Tertel., J. Org. Chem., 51, 1347, 1986) while acid cyclization of meso-acrolein porphyrins has been used extensively to produce benzochlorins (FIG. 13.) (M. G. H, Vincente, I. N. Rezzano, K. M. Smith, Tetrahedron Letters, 31, 1365, 1990; M. J. Gunter, B. C. Robinson, Tetrahedron., 47, 7853, 1991). Diels alder addition of dienophiles with vinyl containing porphyrins has been used extensively to produce chlorins (FIGS. 49–54) (R. Grigg, A. W. Johnson, A. Sweeney, Chem. Commun., 697, 1968, H. J. Callot, A. W. Johnson, A. Sweeney, J. Chem. Soc. Perkin Trans. I, 1424, 1973; V. S. Pangka, A. R. Morgan, D. Dolphin J. Org. Chem. 51, 1094, 1986; P. Yon-Hin, T. P. Wijesekera, D. Dolphin, Tetrahedron Letters, 32, 2875, 1991; P. Yon-Hin, T. P. Wijesekera, D. Dolphin, New. J. Chem, 16, 527, 1992; A. R. Morgan, D. Skalkos, G. M. Garbo, R. W. Keck, S. H. Selman J. Med. Chem. 34, 1991). Acetamidoporphyrins can be cyclized to produce chlorins via a intramolecular Vilsmeier reaction (G. L. Collier, A. H. Jackson, G. W., Kenner, J. Chem. Soc., C., 564, 1969). Recently, chlorin analogues of Purpurin 18 based on purpurin 18, have been produced that possess nitrogens on the cyclic "anhydride" ring system (FIG. 35, A or B=NR) (A. N. Kosyrev, G. Zheng, E. Lazarou, T. J. Dougherty, K. M. Smith, R. Pandey, Tetrahedron Letters, 38, 3335, 1997).

Bacteriochlorins and isobacteriochlorins: (FIGS. 4, 5, 35 to 46)

Bacteriochlorin and isobacteriochlorins are tetrahydroporphyrins. These derivatives have only nine double bonds in their macrocyclic ring system (excluding peripheral groups). The "double" reduction of the porphyrin nucleus at the pyrrole positions has a pronounced effect on the absorption properties and photophysical properties. Typically bacteriochlorins absorb in the 720–850 nm range while isobacteriochlorins absorb in the 500–650 nm range ("The Porphyrins" Ed. D. Dolphin. Academic Press, 1978, Volume III, Chapter 1; References within these volumes provide actual experimental details). Examples of the synthesis of bacteriochlorins and isobacteriochlorins may be found in the following references; H, H Inhoffen. P. Jager and R. Mahlhop and C. D. Mengler, Justus Liebigs Ann. Chem. 704, 188, 1967; H, H Inhoffen, P. Jager and R. Mahlhop and C. D. Mengler, Justus Liebigs Ann. Chem. 704, 188, 1967; H. Mittenzwei, Hoppe-Seyler,s Z. Physiol. Chem. 275, 93, 1942; H. Brockmann Jr., G. Knobloch, Arch. Mikrobiol, 85, 123, 1972; J. J. Katz, H. H., Strain, A. L., Harkness, M. H. Studier, W. A., Svec, T. R. Janson, B. T. Cope, J. Am. Chem Soc. 94, 7983, 1972; D. Dolphin C. Bruckner, U.S. Pat. No. 5,648,485, Date of Patent Jul. 15, 1997; D. Dolphin, P. Y. Hin, T. Wijesekera U.S. Pat. No. 5,149,708, Date of Patent: Sep. 22, 1992; H. W. Whitlock, R. Hanauer, M. Y. Oester, B. K. Bower, J. Am. Chem Soc. 91, 7485, 1969; H, H Inhoffen, H. Sheer, Tetrahedron Letters, 1115, 1972; H, H Inhoffen, J. W. Buchier, R. Thomas, Tetrahedron Letters, 5145, 1969; J. H. Fuhrhop, T. Lumbantobing, Tetrahedron Letters, 2815, 1970; A. Scherz, Y. Saloman, L. Fiedor European patent No: 0584,552 A2; A. Scherz, Y. Saloman, L. Fiedor U.S. Pat. No. 5,650,292; (A. N. Kosyrev, G. Zheng, E. Lazarus, T. J. Dougherty, K. M. Smith, R. Pandey, Tetrahedron Letters, 38, 3335, 1997).

In particular, osmium tetroxide has proved useful in the synthesis of β,β-dihydroxy-bacteriochlorins and isobacteriochlorins from chlorins (R. K. Pandey, T. J. Dougherty, K. M. Smith, F. Y. Shiau, U.S. Pat. No. 5,591,847) and the acid rearrangement of these derivatives has produced numerous bacteriochlorin derivatives. The treatment of porphyrins and chlorins with hydrogen peroxide has been used to produce bacteriochlorins and isobacteriochlorins (H. H. Inhoffen, W. Nolte, Justus Liebigs Ann. Chem. 725, 167, 1969). Diels alder addition of dienophiles with porphyrins containing two β-vinyl substituents has been used extensively to produce bacteriochlorins and isobacteriochlorins (R. Grigg, A. W. Johnson, A. Sweeney, Chem. Commun., 697, 1968, H. J. Callot, A. W. Johnson, A. Sweeney, J. Chem. Soc. Perkin Trans. I, 1424, 1973.; P. Yon-Hin, T. P. Wijesekera, D. Dolphin, Tetrahedron Letters, 32, 2875, 1991; A. R. Morgan. D. Skalkos, G. M. Garbo, R. W. Keck, S. H. Selman J. Med. Chem. 34, 1991).

Phthalocyanines and Naphthalocyanines; (FIGS. 6, 18, 21–24, 28–30).

Phthalocyanines and phthalocyanine analogues are perhaps some of the most widely studied photosensitizers in the field of photodynamic therapy and are also widely used as optical recording media. As such the number of structurally different phthalocyanine derivatives is enormous. Not only can the peripheral functionality be widely varied which changes the electronic spectra and photophysics of the compounds, but metallation of the macrocycle also results in photophysical changes. In addition carbons in the aromatic rings may be substituted with heteroatoms (such as nitrogen, sulphur phosphorus) that change markedly the photophysical properties of the compounds. Examples of references that disclose the formation of such compounds are; "Phthalocyanines Properties and Applications, Eds. C. C. Leznoff, A. B. P. Lever, VCH Publishers Inc., 1989; "The Phthalocyanines", Eds, F. H. Moser, A. L. Thomas, CRC Press, Volumes I and II, 1983; "The Porphyrins" Ed. D. Dolphin, Academic Press, 1978, Volume I, Chapter 9, p 374–380, References within these volumes provide actual experimental details; A. K. Sobbi, D. Wohrle, D. Schlettwein, J. Chem. Soc. Perkin Trans. 2, 481–488, 1993; J. H. Weber, D. H. Busch, Inorg. Chem. 192, 713, 1988.; R. P. Linstead, F. T. Weiss, J. Chem. Soc., 2975, 1950; M. E. Kenney, N. L. Oleinick, U.S. Pat. No. 5,166,197, date of patent Nov. 24, 1992; M. E. Kenney, N. L. Oleinick, U.S. Pat. No. 5,484,778, date of patent: Jan. 16, 1996; P. Gregory, S. J. Reynolds, R. L. White, U.S. Pat. No. 5,484,915, date of patent: Jan. 16, 1996. A great number of binuclear phthalocyanines/napthalocyanines have been synthesised which share a common benzene or naphthalene ring (J. Yang, M. R. Van De Mark, Tetrahedron Letters, 34, 5223, 1993; N. Kobayashi, H Y. Higashi, T. Osa, Chemistry letters, 1813, 1994.

Azoporphyrins: (FIGS. 18, 20, 21, 30, 55)

Porphyrins that possess at least one meso-nitrogen linking atom are called azoporphyrins. The number of meso-nitrogen linking atoms may be extended from one to four. Phthalocyanines and Naphthalocyanine may be regarded as tetraazoporphyrins with extended conjugation due to annelated benzene and napthalene rings. The synthesis of mono, di, tri and tetraazoporphyrin analogues is discussed in "The Porphyrins" Ed. D. Dolphin, Academic Press, 1978, Volume I, Chapter 9, p 365–388; "Phthalocyanines Properties and Applications, Eds. C. C. Leznoff, A. B. P. Lever. VCH Publishers Inc., 1989; "The Phthalocyanines". Eds, F. H. Moser, A. L. Thomas, CRC Press, Volumes I and II, 1983. References within these volumes provide actual experimental details. The synthesis of a series of tetrabenzotriazoporphyrins and tetranapthotriazoporphyrins has recently been published (Y-H, Tse, A. Goel, M. Hue, A. B. P. Lever, C. C. Leznoff, Can. J. Chem. 71, 742, 1993.) and clearly it can be envisaged that chemistry typical of phthalocyanine chemistry and porphyrin chemistry may be applied to these compounds, such that hetero atoms may be introduced into the annelated benzene or napthalene rings.

Unsymmetrical benzonaphthoporphyrazines (FIGS. 25–27, 57)

Unsymmetrical tetraazoporphyrins that have both a benzene and a naphthalene annelated unit in the macrocyclic ring system are loosely called benzonaphthoporphyrazines. The synthesis of these derivatives is carried out using classical phthalocyanine syntheses however, using mixed aromatic dinitriles (U. Michelsen. H. Kliesch, G. Schnurpfeil, A. K. Sobbi, D. Wohrle, Photochem. Photobiol, 64, 694, 1996; S. V. Kudrevich, H. Ali, J. E. Van Lier: Canadian U.S. Pat. No. 2,130,853 Filed Jul. 25, 1994). References to the synthesis of these macrocycles can also be found in "Phthalocyanines Properties and Applications, Eds. C. C. Leznoff, A. B. P. Lever, VCH Publishers Inc., 1989; "The Phthalocyanines", Eds, F. H. Moser, A. L. Thomas, CRC Press, Volumes I and II, 1983.

Texaphyrins: (FIG. 12)

Texaphyrins are tripyrrol dimethene derived "expanded porphyrin" macrocycles who's central core is larger than that of a porphyrin. The reaction of diformyl tripyrranes with functionalized aromatic diamines in the presence of a metal, gives rise to functionalized metallated texaphyrins (J. L. Sessler, G. W. Hemmi, T. D. Mody, U.S. Pat. No. 5,252,720; J. L. Sessler, G. W. Hemmi, T. Murai, U.S. Pat. No. 4,935,498; D. Magda, J. L Sessler, B. Iverson, P. L. Jansen, M. Wright, T D. Mody, G. W. Hemmi, U.S. Pat. No. 5,567,687).

Pentaphyrins and Sapphyrins:—(FIGS. 10, 11)

Sapphyrins and pentaphyrins are fully conjugated macrocycles that possess five pyrrole units. Structural analogues of the sapphyrins and pentaphyrins are outlined in "Porphyrins and Metalloporhyrins", Ed. K. M. Smith, Elsevier, Chapter 18, p750–751; "The Porphyrins Ed. D Dolphin, Academic Press, NY, Chapter 10, p351–356; Broadherst et al, J. Chem. Soc. Perkin Trans. I, 2111, 1972; J. L Sessler, V. Kral, U.S. Pat. 5,543,514).

Porphycenes: (FIG. 8)

Porphycenes are isomeric analogues of porphyrins that have eleven double bonds in their macrocyclic core that are derived formally by a mere reshuffling of the pyrrole and methine moieties. Routes to the synthesis of functionalized porphycenes are outlined in the following references; E. Vogel, C. Richert, T. Benninghaus, M. Muller, A. D. Cross. U.S. Pat. No. 5,409,900; E. Vogel, C. Richert, T. Benninghaus, M. Muller, A. D. Cross. U.S. Pat. No. 5,262, 401; E. Vogel, P. A. Koch, A. Rahbar, A. D. Cross. U.S. Pat. 5,244,671; E. Vogel, M. Muller, A.D., O. Halpern, Cross. U.S. Pat. No. 5,610,175; E. Vogel, M. Muller, A.D,. O. Halpern, A. D. Cross. U.S. Pat. 5,637,608; E. Vogel, C. Richert, T. Benninghaus, M. Muller, A. D. Cross. U.S. Pat. No. 5,179,120; D. Martire, N. Jux, P. F. Armendia, R. M. Negri, J. Lex, S. E. Braslavsky, K. Schaffner, E. Vogel. J. Am. Chem. Soc,. 114, 1992; N. Jux, P. Koch, H. Schmickler, J. Lex, E. Vogel, Angew. Chem. Int. Ed. Engl. 29,1385, 1990.

Corroles: (FIG. 57)

Corroles contain an aromatic 18 electron chromophore. The synthesis and structural modifications of these compounds (such as N-alkylation) are discussed in detail in "The Porphyrins" Ed. D. Dolphin, Academic Press, 1978, Volume I, Chapter 9, p 357–363 and in "Porphyrins and Metalloporphyrins" Ed. K. M. Smith, Elsevier Publishing Company, New York, 1975, Chapter 18, p730 –749.

It will be appreciated that various changes and modifications can be made from the specific details of the invention as disclosed above, and as described in the foregoing examples and that, in its essential details, the invention is a composition which is comprised essentially of a non-radioactive indium atom complexed with the inner nitrogens of a pyrrolic core composed of at least two pyrroles, with the proviso that fully unsaturated porphyrins having the structures:

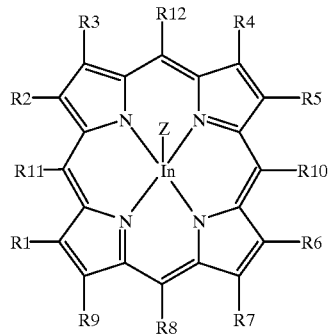

where R1, R2, R4 and R6 are methyl, R8, R10, R11 and R12 are hydrogen, and R7 and R8 are CH$_2$CH$_2$COR13 (where R13 is a moiety which results from the removal of H from an amino acid), and

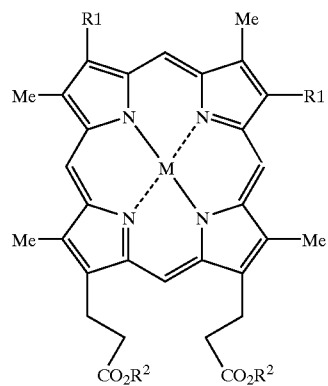

where R1 is CH(OH)Me, R is alkyl, and $R^2$ is a residue derived by removing H from an amino acid are excluded.

Preferably, the invention is a composition which is comprised essentially of a non-radioactive indium atom complexed with the inner nitrogens of a tetrapyrrolic core, with the proviso that the fully unsaturated porphyrins identified above are excluded. A non-radioactive indium atom complexed with the inner nitrogens of a photosensitive compound having a dihydro or tetrahydro tetrapyrrolic core is another preferred composition of the invention.

Other preferred families of compounds according to the invention have the structures of FIGS. 1 to 58, above. Specifically, one preferred family has the structure of FIG. 2, where each of R1 through R12 is H, halide, alkyl, cyclic alkyl (3–6 carbons), aryl, vinyl, substituted aryl, alkenyl, substituted alkenyl, alkynyl, substituted alkynyl, amide, ester, NR12R12, CN, OH, OR12, CHO, (CH$_2$)$_n$OH, (CH$_2$)$_n$SH, (CH$_2$)$_n$O-alkoxy, (CH$_2$)$_n$SR12, (CH$_2$)$_n$OR12 (where n=1, 2, 3, 4, and R12 is a functional group less than or equal to 100000 daltons), (CH$_2$)$_n$CO$_2$R12 (where R12 is H, a physiologically acceptable salt, aLkyl (1–6 carbons), aryl, substituted aryl, alkenyl, substituted alkenyl, alkynyl, or substituted alkynyl, and n=1, 2, 3, 4), (CH$_2$)$_n$CONHR12, (CH$_2$)$_n$CON(R12)$_2$, CO$_2$R12 (where R12 is a functional group less than or equal to 100000 daltons), SR12 (where R12 is a functional group less than or equal to 100000 daltons), SO$_3$H, SO$_3$R12, SO$_2$NHR12, SO$_2$N(R12)$_2$, SO$_2$N(R12)$_3^+$X$^-$ (where R12 is a functional group less than or equal to 100000 daltons and X is a charge balancing ion).

Z is a halide, acetate, OH, alkyl, aryl, substituted aryl, alkenyl, substituted alkenyl, alkynyl, substituted alkynyl, or a functional group less than or equal to 100000 daltons, protein or biomolecule, with the exclusions noted above when the pyrrolic core is fully unsaturated.

Still another preferred family has the following structure:

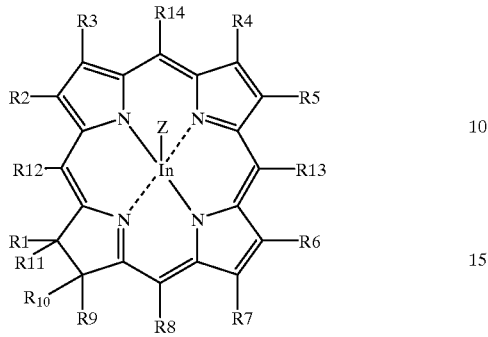

where each of R1 through R14 is H, halide, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR15R15, CN, OH, OR15, CHO, $COCH_3$, $(CH_2)_nOH$, $(CH_2)_nSH$, $(CH_2)_nO$-alkoxy, $(CH_2)_nSR15$, $(CH_2)_nOR15$ (where n=1, 2, 3, 4, and R15 is a functional group less than or equal to 100000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR15$, $(CH_2)_nCON(R15)_2$, $CO_2R15$, $CONHR15$, $CON(R15)_2$, (where R15 is a functional groups less than or equal to 100000 daltons), SR15 (where R15 is a functional group less than or equal to 100000 daltons), $SO_3H$, $SO_3R15$, $SO_2NHR15$, $SO_2N(R15)_2$, $SO_2N(R15)_3{}^+X^-$ (where R15 is a functional group less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, or a functional group less than or equal to 100000 daltons, proteins or biomolecules.

M in the foregoing formula can also be Pd, Sn, Pt, Al, Ru, Ga.

Another preferred family has the following structure:

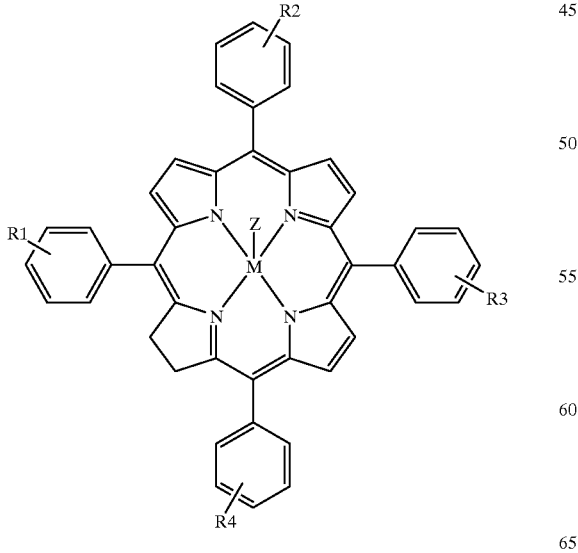

Where each of R1 through R4 is selected from $SO_3H$ (or a salt thereof), $SO_2NHR5$, $CO_2H$ (or a salt thereof), CONHR5, OH, OR5 (wherein R5 is a alcohol or ether containing group), amide, $N(CH_3)_2$, $N(Et)_2$.

M is $In^{113}$, $In^{115}$ or a mixture of $In^{113}$ and In115

Z is a halide, acetate, OH.

M in the foregoing formula can also be Pd, Sn, Pt, Al, Ru, Ga.

Another preferred family has the following structure:

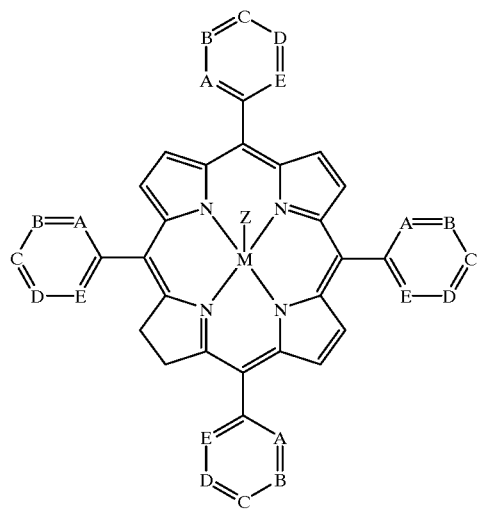

Where each of A, B, C, D and E is C, N, $N^+R$ (where R is alkyl charged or uncharged) or combinations thereof;

M is $In^{113}$, $In^{115}$ or a mixture of $In^{113}$ and $In^{115}$ and

Z is a halide, acetate, OH.

M is the foregoing formula can also be Pd, Sn, Pt, Al, Zn, Ru, Ga.

Still another preferred family has the structure:

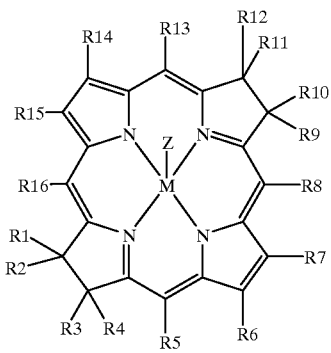

Where each of R1 through R16 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3$ $X^-$ (where X is a charge balancing ion), $C(X)_2C(X)_3$ (where X is a halogen), NR17R17, CN, OH, OR17, CHO, $COCH_3$, $CH(OR17)CH_3$, $(CH_2)_nOH$, $(CH_2)_nSH$, $(CH_2)_nO$-alkoxy, $(CH_2)_nSR17$, $(CH_2)_nOR17$ (where n=1, 2, 3, 4, and R17 is a functional groups less than or equal to 100000 daltons), $(CH_2)_nCO_2R17$ (where R17 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR17$, $(CH_2)_nCON(R17)_2$, $CO_2R17$, $CONHR17$, $CONR17R17$, $SR17$ (where R17 is a functional groups less than or equal to 100000 daltons), $SO_3H$, $SO_3R17$, $SO_2NHR17$, $SO_2N(R17)_2$ $SO_2N(R17)_3{+}X^-$ (where R17 is a functional groups less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkyne, or functional groups less than or equal to 100000 daltons, proteins or biomolecules.

Yet another family has the structure:

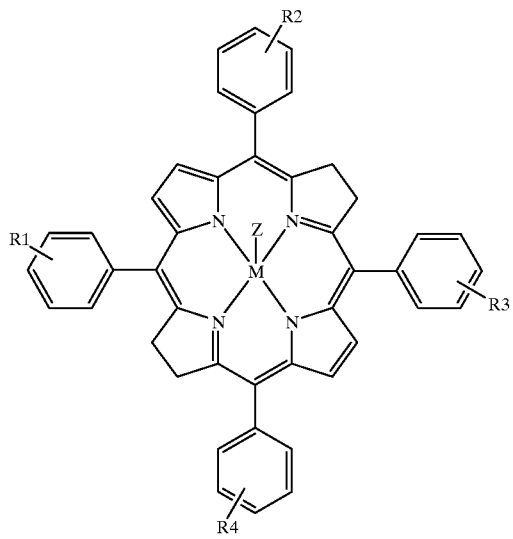

Where each of R1 through R4 is $SO_3H$ (or a salt thereof), $SO_2NHR5$, $CO_2H$ (or a salt thereof), $CONHR5$, OH, OR5 (wherein R5 is a alcohol or ether containing group), amide, $N(CH_3)_2$, $N(Et)_2$.

M is $In^{113}$, $In^{115}$ or a mixture of $In^{113}$ and $In^{115}$

Z is a halide, acetate, OH.

M can also be Pd, Sn, Pt, Al, Zn, Ru, Ga.

Still another family has the structure:

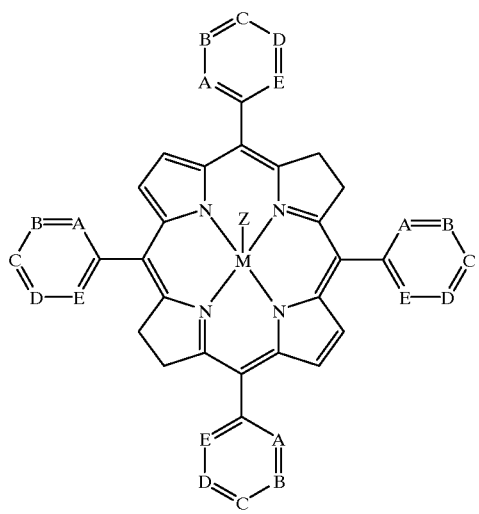

Where each of A–E is C, N, or $N^+R$ (where R is a charged or uncharged alkyl group);

M is $In^{113}$, $In^{115}$ or a mixture of $In^{113}$ and $In^{115}$

Z is halide, acetate, or OH.

M can also be Pd, Sn, Pt, Al, Zn, Ru, Ga.

Another family has the structure:

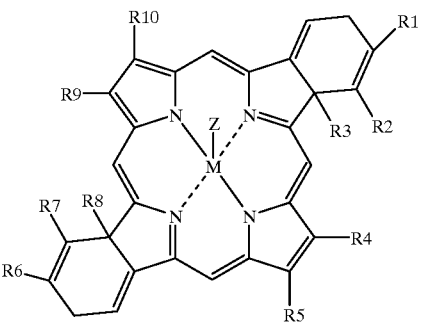

Where each of R1 through R10 is H, halide, alkyl, cyclic alkyl (1–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3$ $X^-$ (where X is a charge balancing ion), $C(X)_2C(X)_3$ (where X is a halogen), $NR11R11$, CN, OH, $OR11$, CHO, $COCH_3$, $CH(OR11)CH_3$, $(CH_2)_nOH$, $(CH_2)_nSH$, $(CH_2)_nO$-alkoxy, $(CH_2)_nSR11$, $(CH_2)_nOR11$ (where n=1, 2, 3, 4, and R11 is a functional groups less than or equal to 100000 daltons), $(CH_2)_nCO_2R11$ (where R11 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR11$, $(CH_2)_nCON(R11)_2$, $CO_2R11$, $CONHR11$, $CONR11R11$, $SR11$ (where R11 is a functional groups less than or equal to 100000 daltons), $SO_3H$, $SO_3R11$, $SO_2NHR11$, $SO_2N(R11)_2$, $SO_3N(R11)_3{+}X^-$ (where R11 is a functional groups less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, or a functional group less than or equal to 100000 daltons, proteins or biomolecules.

M can also be Pd, Sn, Pt, Al, Zn, Ru, Ga.

Another family of compounds has the structure immediately above, where each of R1, R2, R6, R7 is $CO_2H$ (or a salt thereof), or $CO_2R11$ (where R11 is alkyl or aryl).

Each of R3 and R8 is methyl or ethyl.

Each of R4, R5, R9, R10 is methyl, ethyl alkyl, $CH_2CH_2CO_2H$ (or salts thereof), or $CH_2CH_2CO_2R11$ (where R11 is alkyl or aryl).

M is $In^{113}$, $In^{115}$ or a mixture of $In^{113}$ and $In^{115}$ and Z is a halide, acetate, OH.

M can also be Pd, Sn, Pt, Al, Zn, Ru, Ga.

Still another family of compounds has the structure:

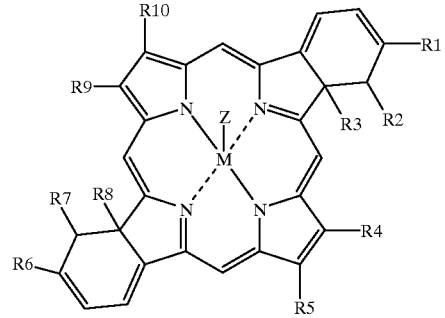

Where each of R1–R10 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3 X^-$ (where X is a charge balancing ion), $C(X)_2C(X)_3$ (where X is a halogen), NR11R11, CN, OH, OR11, CHO, $COCH_3$, $CH(OR11)CH_3$, $(CH_2)_nOH$, $(CH_2)_nSH$, $(CH_2)_n$O-alkoxy, $(CH_2)_nSR11$, $(CH_2)_nOR11$ (where n=1, 2, 3, 4, and R11 is a functional group less than or equal to 100000 daltons), $(CH_2)_nCO_2R11$ (where R11 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR11$, $(CH_2)_nCON(R11)_2$, $CO_2R11$, CONHR11, CONR11R11, SR11 (where R11 is a functional groups less than or equal to 100000 daltons), $SO_3H$, $SO_3R11$, $SO_2NHR11$, $SO_2N(R11)_2$, $SO_3N(R11)_3^+X^-$ (where R11 is a functional groups less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl; substituted alkynyl, or a functional group less than or equal to 100000 daltons, proteins or biomolecules.

Another family of compounds has the structure:

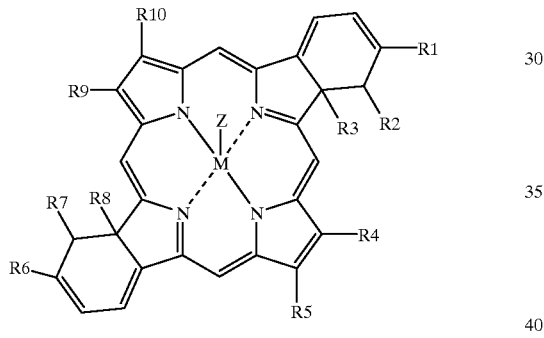

Where each of R1–R10 is H, halide, alkyl, cyclic alkyl (3–6 carbons), aryl, substituted aryl, alkenyl, substituted alkenyl, alkynyl, substituted alkynyil, amide, ester, $CH=CHCH_2N(CH_3)_2$, $CH=CHCH_2N^+(CH_3)_3 X^-$ (where X is a charge balancing ion), $C(X)_2C(X)_3$ (where X is a halogen), NR11R11, CN, OH, OR11, CHO, $COCH_3$, $CH(OR11)CH_3$, $(CH_2)_nOH$, $(CH_2)_nSH$, $(CH_2)_n$O-alkoxy, $(CH_2)_nSR11$, $(CH_2)_nOR11$ (where n=1, 2, 3, 4, and R11 is a functional group less than or equal to 100000 daltons), $(CH_2)_nCO_2R11$ (where R11 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR11$, $(CH_2)_nCON(R11)_2$, $CO_2R11$, CONHR11, CONR11R11, SR11, (where R11 is a functional group less than or equal to 100000 daltons), $SO_3H$, $SO_3R11$, $SO_2NHR11$, $SO_2N(R11)_2$, $SO_3N(R11)_3^+X^-$ (where R11 is a functional groups less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, or a functional group less than or equal to 100000 daltons, protein or biomolecule.

M can also be Pd, Sn, Pt, Al, Zn, Ru, Ga.

Another family has the structure:

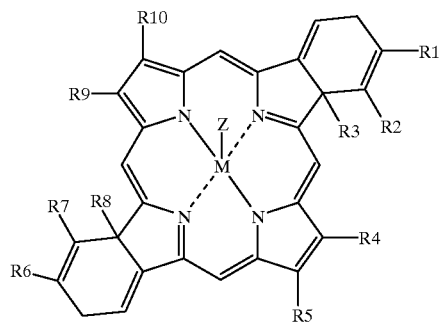

where each of R1, R2, R6, R7 is $CO_2H$ (or a salt thereof), $CO_2R11$ (where R11 is alkyl or aryl).

each of R3 and R8 is methyl or ethyl.

each of R4, R5, R9, R10 is methyl, ethyl, alkyl, $CH_2CH_2CO_2H$ (or a salt therof), or $CH_2CH_2CO_2R11$ (where R11 is alkyl or aryl).

M is $In^{113}$, $In^{115}$ or a mixture of $In^{113}$ and $In^{115}$; and Z is a halide, acetate, OH.

M can also be Pd, Sn, Pt, Al, Zn, Ru, Ga.

Yet another family of compounds has the following structure;

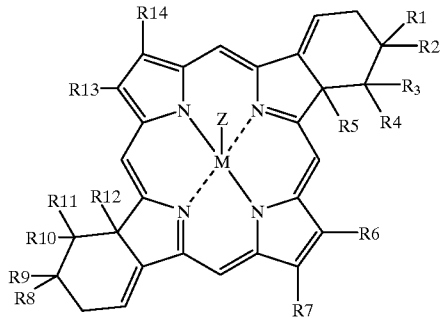

Where each of R1–R14 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3 X^-$ (where X is a charge balancing ion), $C(X)_2C(X)_3$ (where X is a halogen), NR15R15, CN, OH, OR15, CHO, $COCH_3$, $CH(OR15)CH_3$, $(CH_2)_nOH$, $(CH_2)_nSH$, $(CH_2)_n$O-alkoxy, $(CH_2)_nSR15$, $(CH_2)_nOR15$ (where n=1, 2, 3, 4, and R15 is a functional groups less than or equal to 100000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR15$, $(CH_2)_nCON(R15)_2$, $CO_2R15$, CONHR15, CONR15R15, SR15 (where R15 is a functional group less than or equal to 100000 daltons), $SO_3H$, $SO_3R15$, $SO_2NHR15$, $SO_2N(R15)_2$, $SO_3N(R15)_3^+X^-$ (where R15 is a functional group less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, or a functional group less than or equal to 100000 daltons, protein or biomolecule.

Still another family of compounds has the structure:

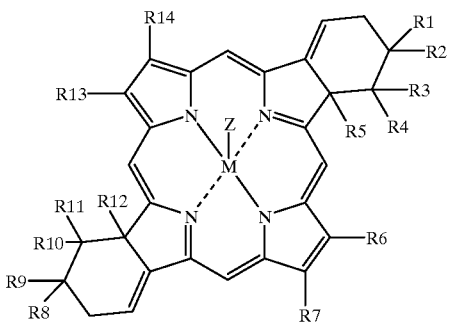

Where each of R1, R2, R3, R4, R8, R9, R10, R11 is CN
Each of R5 and R12 is methyl or ethyl.
Each of R6, R7, R13 and R14 is methyl, ethyl, alkyl, $CH_2CH_2CO_2H$ (or salts thereof), or $CH_2CH_2CO_2R15$ (where R15 is alkyl, aryl).
M is $In^{113}$, $In^{115}$ or a mixture of $In^{113}$ and $In^{115}$.
Z is a halide, acetate, or OH.
M can also be Pd, Sn, Pt, Al, Zn, Ru, Ga.
Another family of compounds has the structure:

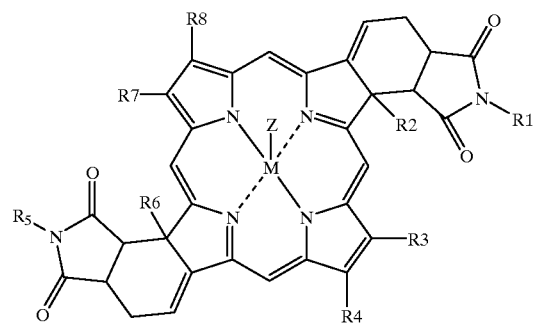

Where each of R1–R8 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3$ $X^-$ (where X is a charge balancing ion), $C(X)_2C(X)_3$ (where X is a halogen), NR9R9, CN, OH, OR9, CHO, $COCH_3$, $CH(OR9)CH_3$, $(CH_2)_nOH$, $(CH_2)_nSH$, $(CH_2)_nO$-alkoxy, $(CH_2)_nSR9$, $(CH_2)_nOR9$ (where n=1, 2, 3, 4, and R9 is a functional group less than or equal to 100000 daltons), $(CH_2)_nCO_2R9$ (where R9 is H, a physiologically acceptable salt, alkyl (1–6 carbons), aryl, substituted aryl, alkenyl, substituted alkenyl, alkynyl, or substituted alkynyl, and n=1, 2, 3,4), $(CH_2)_nCONHR9$, $(CH_2)_nCON(R9)_2$, $CO_2R9$, CONHR9, CONR9R9, SR9 (where R9 is a functional groups less than or equal to 100000 daltons), $SO_3H$, $SO_3R9$, $SO_2NHR9$, $SO_2N(R9)_2$, $SO_3N(R9)_3^+X^-$ (where R9 is a functional group less than or equal to 100000 daltons and X is a charge balancing ion): M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, or a functional group less than or equal to 100000 daltons, protein or biomolecule.

Another family of compounds has the structure:

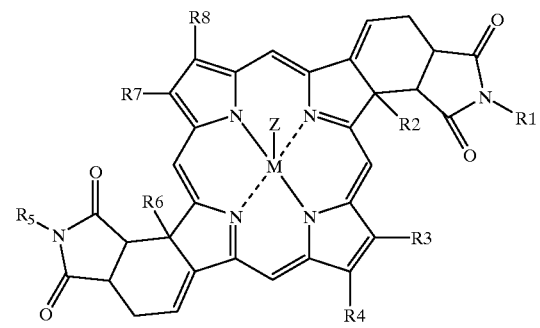

where each of R1 and R5 is alkyl or aryl.
Each of R2 and R6 is methyl or ethyl.
Each of R7, R8, R3, and R4 is methyl, ethyl alkyl, $CH_2CH_2CO_2H$ (or a salt thereof), or $CH_2CH_2CO_2R9$ (where R9 is alkyl or aryl).
M is $In^{113}$, $In^{115}$ or a mixture of $In^{113}$ and $In^{115}$.
Z is a halide, acetate, OH.
M can also be Pd, Sn, Pt, Al, Zn, Ru, Ga.
Yet another family of compounds has the structure:

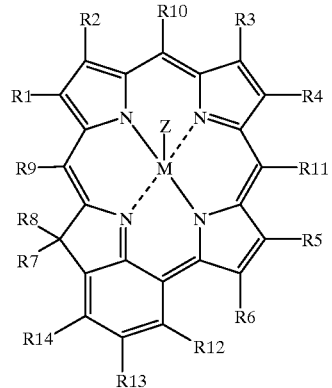

Where each of R1–R14 is H, halide, methyl, ethyl, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR15R15, CN, OH, OR15, CHO, $COCH_3$, $CH(OR15)CH_3$, $(CH_2)_nOH$, $(CH_2)_nSH$, $(CH_2)_nO$-alkoxy, $(CH_2)_nSR15$, $(CH_2)_nOR15$ (where n=1, 2, 3, 4, and R15 is a functional groups less than or equal to 100000 daltons), $(CH_2)_nCO_2R15$ (where R14 is H, a physiologically acceptable salt, alkyl (1–6 carbons), aryl, substituted aryl, alkenyl, substituted alkenyl, alkynyl, or substituted alkynyl and n=1, 2, 3, 4), $(CH_2)_nCONHR15$, $(CH_2)_nCON(R15)_2$, $CO_2R15$, CONHR15, CONR15R15, SR15 (where R 15 is a functional group less than or equal to 100000 daltons and n=1, 2, 3, 4), $SO_3H$, $SO_3R15$, $SO_2NHR15$, $SO_2N(R15)_2$, $SO_3N(R15)_3^+X^-$ (where R15 is a functional group less than or equal to 100000 daltons and X is a charge balancing ion); M is $In^{113}$, $In^{115}$ or a mixture of $In^{113}$ and $In^{115}$ Z is a halide, acetate, OH, alkyl, aryl, substituted aryl, alkenyl, substituted alkenyl, alkynyl, substituted alkynyl, or a functional group less than or equal to 100000 daltons, protein or biomolecule.
M can also be Pd, Sn, Pt, Al, Zn, Ru, Ga.

47

Another family of compounds has the structure:

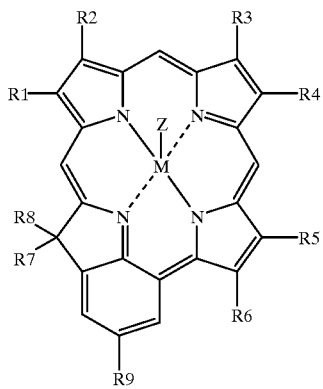

where each of R1–R8 is ethyl or methyl

R9 is $CH_3$, $SO_2NH(CH_2CH_2O)_nCH_3$ (n=1 to 1000), $SO_2N((CH_2CH_2O)_nCH_3)_2$ (n=1 to 1000); $SO_2NH(CH_2)_nOH$ (n=1 to 1000), $CH_3$, $SO_2N((CH_2CH_2)_nOH)_2$ (n=1 to 1000); $SO_2NC((N(CH_3)_2)_2$; $SO_2NH(CH_2)_nN(CH_3)_2$ (n=1 to 1000); $SO_2NH(CH_2)_nSH$ (n=1 to 1000); $SO_2NHC(CH_2CH_2OH)_3$; $SO_2NHCH_2CO_2H$ (or salts thereof); $SO_2NH(CH_2)_nCH(NH_2)CO_2H$ (or salts thereof) (n=1 to 5); $SO_2NHCH_2CO_2R10$ (R10 is alkyl, aryl); $SO_2NH(CH_2)_nCH(NH_2)CO_2R10$ (R10 is alkyl, aryl) (n=1 to 5)

M is $In^{113}$, $In^{115}$ or a mixture of $In^{113}$ and $In^{115}$ is a halide, acetate, OH.

M can also be Pd, Sn, Pt, Al, Zn, Ru, Ga.

Another family of compounds has the structure:

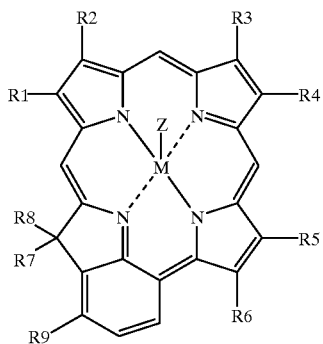

where each of R1–R8 is ethyl or methyl.

R9 is; $CH_2CO_2NH(CH_2CH_2O)_nCH_3$ (n=1 to 1000), $CH_2CO_2N((CH_2CH_2O)_nCH_3)_2$ (n=1 to 1000): $CH_2CO_2NH(CH_2)_nOH$ (n=1 to 1000), $CH_2CO_2N((CH_2CH_2)_nOH)_2$(n=1 to 1000); $CH_2CO_2NC((N(CH_3)_2)_2$; $CH_2CO_2NH(CH_2)_nN(CH_3)_2$ n=1 to 1000); $CH_2CO_2NH(CH_2)_nSH$ (n=1 to 1000); $CH_2CO_2NHC(CH_2CH_2OH)_3$; $CH_2CO_2NHCH_2CO_2H$ (or salts thereof); $CH_2CO_2NH(CH_2)_nCH(NH_2)CO_2H$ (or salts thereof) (n=1 to 5); $CH_2CO_2NHCH_2CO_2R10$ (R10 is alkyl or aryl); $CH_2CO_2NH(CH_2)_nCH(NH_2)CO_2R10$ (R10 is alkyl, aryl) (n=1 to 5)

M is $In^{113}$, $In^{115}$ or a mixture of $In^{113}$ and $In^{115}$.

Z is a halide, acetate, OH.

M can also be Pd, Sn, Pt, Al, Zn, Ru, Ga.

48

Another family has the structure:

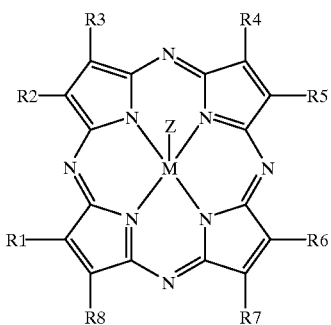

where each of R1–R8 is H, halide, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR9R9, CN, OH, OR9, CHO, $COCH_3$, $(CH_2)_nOH$, $(CH_2)_nSH$, CH(OR9)$CH_3$, $(CH_2)_nO$-alkoxy, $(CH_2)_nSR9$, $(CH_2)_nOR9$ (where n=1, 2, 3, 4, and R9 is a functional group less than or equal to 100000 daltons), $(CH_2)_nCO_2R9$ (where R9 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR9$, $(CH_2)_nCON(R9)_2$, $CO_2R9$, CONHR9, CONR9R9, SR9 (where R9 is a functional groups less than or equal to 100000 daltons), $SO_3H$, $SO_3R9$, $SO_2NHR9$, $SO_2N(R9)_2$, $SO_2N(R9)_3^+X^-$ (where R9 is a functional group less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd, Sn, Pt, Al, Zn, Ru, Ga.

Another family of compounds has the structure:

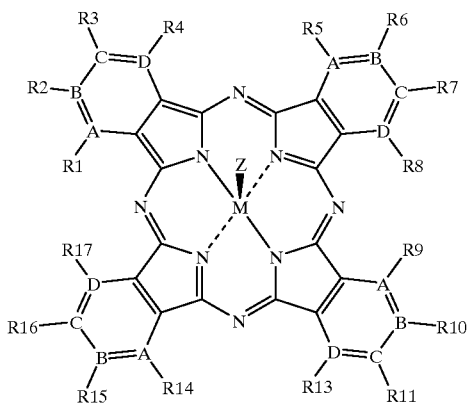

where each of R1–R17 is H, halide, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR18R18, CN, OH, OR18, CHO, $COCH_3$, $(CH_2)_nOH$, $(CH_2)_nSH$, CH(OR18)$CH_3$, $(CH_2)_nO$-alkoxy, $(CH_2)_nSR18$, $(CH_2)_nOR18$(where n=1, 2, 3, 4, and R5 is a functional group less than or equal to 100000 daltons), $(CH_2)_nCO_2R18$ (where R18 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n CONHR18$, $(CH_2)_n CON(R18)_2$, $CO_2R18$, $CONHR18$, $CONR18R18$, $SR18$ (where R18 is a functional groups less than or equal to 100000 daltons), $SO_3X$, $S_3R18$, $SO_2NHR18$, $SO_2N(R18)_2$, $SO_2N(R18)_3^+X^-$ (where R18 is a functional group less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyil, protein or biomolecule or functional group less than or equal to 100000 daltons.

M can also be Pd, or Ga.

Still another family has the structure:

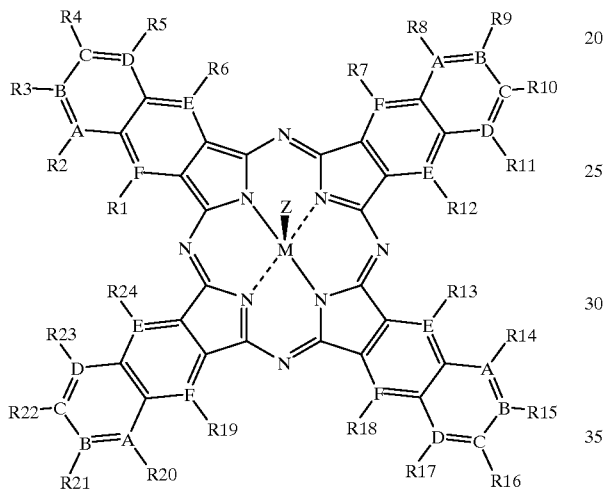

where each of R1–R24 is H, halide, alkyl, cyclic alkyl (3–6 carbons), aryl, substituted aryl, alkenyl, substituted alkenyl alkynyl, substituted alkynyl, amide, ester, $C(X)_2C(X)_3$ (where X is a halogen), NR25R25, CN, OH, OR25, CHO, $COCH_3$, $(CH_2)_n OH$, $(CH_2)_n SH$, $CH(OR25)CH_3$, $(CH_2)_n$O-alkoxy, $(CH_2)_n SR25$ $(CH_2)_n OR25$ (where n=1, 2, 3, 4, and R25 is a functional groups less than or equal to 100000 daltons), $(CH_2)_n CO_2R25$ (where R25 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n CONHR25$, $(CH_2)_n CON(R25)_2$, $CO_2R25$, $CONHR25$, $CONR25R25$, $SR25$ (where R25 is a functional group less than or equal to 100000 daltons), $SO_3H$, $SO_3R25$, $SO_2NHR25$, $SO_2N(R25)_2$, $SO_2N(R25)_3^+X^-$ (where R25 is a functional group less than or equal to 100000 daltons and X is a charge balancing ion); M is $In^{113}$, $In^{115}$ or a mixture of $In^{113}$ and $In^{115}$; A, B, C, D, E, F are; C, N, O+, O, S, Te, P, $N^+(R25)X^-$ (where R25 is a functional groups less than or equal to 100000 daltons and X is a charge balancing ion), or combinations thereof; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga.

Another family of compounds has the structure:

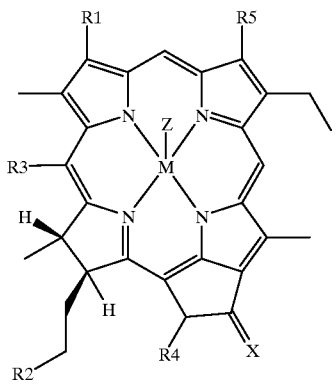

where each of R1–R5 is $CH_2CH_3$, $CH=CH_2$, $CH=CHCH_2N(CH_3)_2$ $CH=CHCH_2N^+$ $(CH_3)_3$ $X^-$ (where X is a charge balancing ion), $C(X)_2C(X)_3$ (where X is a halogen), CHO, $COCH_3$, $CO_2H$, $CO_2R6$, CONHR7, $CH=CHCHO$, $CH_2Y$, (where Y=H, halogen, OH, OR6 or is a functional group less than or equal to 100000 daltons), $CH=CHCH_2OH$, $CH=CHCH_2OR6$, $CH(OH)CH_3$, $CH(OR6)CH_3$, H, halide, alkyl, cyclic alkyl (1–6 carbons), aryl, substituted aryl, alkenyl, substituted alkenyl, alkynyl, substituted alkynyl, amide, ester, NR6R6, CN, OH, OR6, $(CH_2)_n OH$, $(CH_2)_n SH$, $(CH_2)_n$O-alkoxy, $(CH_2)_n SR6$, $(CH_2)_n OR6$ (where n=1, 2, 3, 4, and R6 is a functional group less than or equal to 100000 daltons), $(CH_2)_n CO_2R6$ (where R6 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n CONHR6$, $(CH_2)_n CON(R6)_2$, $CO_2R6$, CONHR6, CONR6R6, SR6 (where R6 is a functional group less than or equal to 100000 daltons), $SO_3H$, $SO_3R6$, $SO_2NHR6$, $SO_2N(R6)_2$, $SO_2N(R6)_3^+X^-$ (where R6 is a functional group less than or equal to 100000 daltons and X is a charge balancing ion); X is, O, 2H, (H, OH), S, (H, OR6) or a ketone protecting group; M is $In^{1131}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd, Sn, Pt, Al, Zn, Ru, Ga.

Still another family of compounds has the structure:

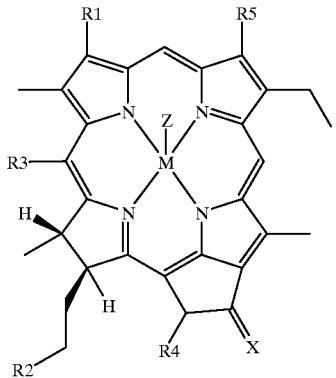

wherein:

R1 is CH=CH$_2$, CHO, Et, COCH$_3$
R2 is CO$_2$CH$_3$, CO$_2$H, amide
R3 and R4 are H
R5 is CH$_3$
X is O
M is In$^{113}$, In$^{115}$ or a mixture of In$^{113}$ and In$^{115}$
Z is a halide, acetate or OH.
M can also be Ag, Al, Ce, Co, Cr, Cu, Dy, Er, Fe, Ga, Hf, Ho, La, Lu, Mo, Nd, Pb, Pd, Pr, Pt, Rh, Sb, Sc, Sm, Sn, Pt, Ru, Tb, Th, Ti, Tl, Tm, U, V, Y, Yb, Zn or Zr, preferably Pd, Sn, Pt, Al, Zn, Ru, Ga.

Another family of compounds has the structure:

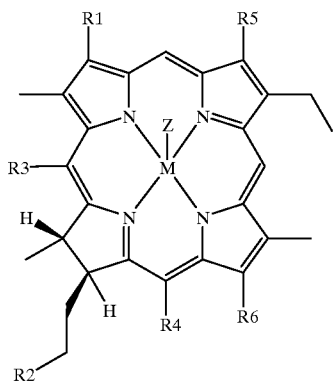

where each of R1–R6 is; CH$_2$CH$_3$, CH=CH$_2$, CH=CHCH$_2$N(CH$_3$)$_2$, CH=CHCH$_2$N$^+$ (CH$_3$)$_3$ X$^-$ (where X is a charge balancing ion), C(X)$_2$C(X)$_3$ (where X is a halogen), CHO, COCH$_3$, CO$_2$H, C$_2$R7, CONHR7, CH=CHCHO, CH$_2$Y, (where Y=H, halogen, OH, OR7 or is a functional group less than or equal to 100000 daltons), CH=CHCH$_2$OH, CH=CHCH$_2$OR7, CH(OH)CH$_3$, CH(OR7)CH$_3$, H, halide, alkyl, cyclic alkyl (1–6 carbons), aryl, substituted aryl, alkenyl, substituted alkenyl, alkynyl, substituted alkynyl, amide, ester, NR7R7, CN, OH, OR7, (CH$_2$)$_n$OH, (CH$_2$)$_n$SH, (CH$_2$)$_n$O-alkoxy, (CH$_2$)$_n$SR7, (CH$_2$)$_n$OR7 (where n=1, 2, 3, 4, and R7 is a functional group less than or equal to 100000 daltons), (CH$_2$)$_n$CO$_2$R7 (where R7 is H, a physiologically acceptable salt, alkyl (1–6 carbons), aryl, substituted aryl, alkenyl, substituted alkenyl, alkynyl, or substituted alkynyl, and n=1, 2, 3, 4), (CH$_2$)$_n$CONHR7, (CH$_2$)$_n$CON(R7)$_2$, CO$_2$R7, CONHR7, CONR7R7, SR7 (where R7 is a functional group less than or equal to 100000 daltons), SO$_3$H, SO$_3$R7, SO$_2$NHR7, SO$_2$N (R7)$_2$, SO$_2$N(R7)$_3$$^+$X$^-$ (where R7 is a functional group less than or equal to 100000 daltons and X is a charge balancing ion); M is In$^{113}$, In$^{115}$ or a mixture of In$^{113}$ and In$^{115}$Z; is a halide, acetate, OH, alkyl, aryl, substituted aryl, alkenyl, substituted alkenyl, alkynyl, substituted alkynyl, protein or biomolecule or functional group less than or equal to 100000 daltons; with the proviso that when R2 =CO,NHR6, R6 can not be a mono- or di-carboxylic acid of an amino acid.

M can also be Ag, Al, Ce, Co, Cr, Cu, Dy, Er, Fe, Ga, Hf, Ho, La, Lu, Mo, Nd, Pb, Pd, Pr, Pt, Rh, Sb, Sc, Sm, Th, Th, Ti, Tl, Tm, U, V, Y, Yb, Zr, preferably Pd, Pt, Ga, Al, Ru, Sn or Zn.

Another family of compounds has the following structure:

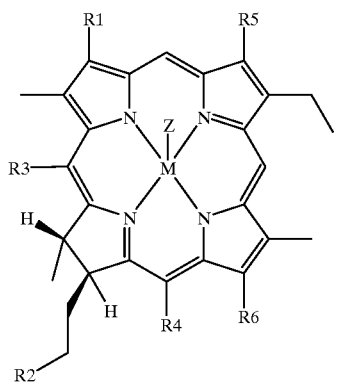

where each of R1–R6 is; CH$_2$CH$_3$, CH=CH$_2$, CH=CHCH$_2$N(CH$_3$)$_2$, CH=CHCH$_2$N$^+$ (CH$_3$)$_3$X$^-$ (where X is a charge balancing ion), C(X)$_2$C(X)$_3$ (where X is a halogen), CHO, COCH$_3$, CO$_2$H, CO$_2$R7, CONHR7, CH=CHCHO, CH$_2$Y, (where Y=H, halogen, OH, OR7 or is a functional group less than or equal to 100000 daltons), CH=CHCH$_2$OH, CH=CHCH$_2$OR7, CH(OH)CH$_3$, CH(OR7)CH$_3$, H, halide, alkyl, cyclic alkyl (3–6 carbons), aryl, substituted aryl, alkenyl, substituted alkenyl, alkynyl, substituted alkynyl, amide, ester, NR7R7, CN, OH, OR7, (CH$_2$)$_n$OH, (CH$_2$)$_n$SH, (CH$_2$)$_n$O-alkoxy, (CH$_2$)$_n$SR7, (CH$_2$)$_n$OR7 (where n=1, 2, 3, 4, and R7 is a functional group less than or equal to 100000 daltons), (CH$_2$)$_n$CO$_2$R7 (where R7 is H, a physiologically acceptable salt, alkyl (1–6 carbons), aryl, substituted aryl, alkenyl, substituted alkenyl, alkynyl or substituted alkynyl, and n=1, 2, 3, 4), (CH$_2$)$_n$CONHR7, (CH$_2$)$_n$CON(R7)$_2$, CO$_2$R7, CONHR7, CONR7R7, SR7, (where R7 is a functional group less than or equal to 100000 daltons), SO$_3$H, SO$_3$R7, SO$_2$NHR7, SO$_2$N (R7)$_2$, SO$_2$N(R7)$_3$$^+$X$^-$ (where R7 is a functional group less than or equal to 100000 daltons and X is a charge balancing ion); M is In$^{113}$, In$^{115}$ or a mixture of In$^{113}$ and In$^{115}$Z is a halide, acetate, OH, alkyl, aryl, substituted aryl, alkenyl, substituted alkenyl, alkynyl, substituted alkynyl, protein or biomolecule or functional group less than or equal to 100000 daltons.

Still another family of compounds has the following structure:

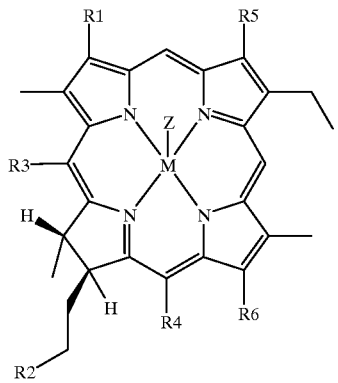

wherein;

R1 is CH=CH$_2$, CHO, Et, COCH$_3$

R2 is CO$_2$CH$_3$

R3 is H

R4 is CH$_2$CO$_2$CH$_3$, CO$_2$CH$_3$, CH$_2$CO$_2$H (or a salt thereof), CO$_2$H (or a salt thereof).

R5 is CH$_3$

R6 is CO$_2$H, CO$_2$Me or an amide

M is In$^{113}$, In$^{115}$ or a mixture of In$^{113}$ and In$^{115}$

Z is a halide, acetate, or OH.

M can also be Ag, Al, Ce, Co, Cr, Cu, Dy, Er, Fe, Ga, Hf, Ho, In, La, Lu, Mo, Nd, Pb, Pd, Pr, Pt, Rh, Sb, Sc, Sm, Sn, Tb, Th, Ti, Tl, Tm, U, V, Y, Yb, Zn, or Zr, preferably Pd, Pt, Ga, Al, Ru, Sn or Zn.

Another family of compounds has the structure:

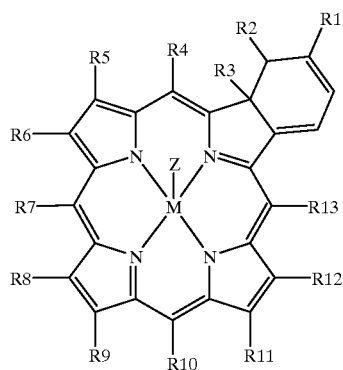

where each R1–R13 is H, halide, alkyl, vinyl, cyclic alkyl (3–6 carbons), aryl, substituted aryl, alkenyl, substituted alkenyl, alkynyl, substituted alkynyl, amide, ester, CH=CHCH$_2$N(CH$_3$)$_2$, CH=CHCH$_2$N$^+$ (CH$_3$)$_3$ X$^-$ (where X is a charge balancing ion), C(X)$_2$C(X)$_3$ (where X is a halogen), NR14R14, CN, OH, OR14, CHO, COCH$_3$, (CH$_2$)$_2$OH, (CH$_2$)$_n$SH, (CH$_2$)$_n$O-alkoxy, CH(OH)CH$_3$, CH(OR14)CH$_3$ (CH$_2$)$_n$SR14, (CH$_2$)$_n$OR14 (where n=1, 2, 3, 4, and R14 is a functional group less than or equal to 100000 daltons), (CH$_2$)$_n$CO$_2$R14 (where R14 is H, a physiologically acceptable salt, alkyl (1–6 carbons), aryl, substituted aryl, alkenyl, substituted alkenyl, alkynyl, or substituted alkynyl, and n=1, 2, 3, 4), (CH$_2$)$_n$CONHR14, (CH$_2$)$_n$CON(R14)$_2$, CO$_2$R14, CONHR14, CONR14R14, SR14 (where R14 is a functional group less than or equal to 100000 daltons), SO$_3$X, SO$_3$R14, SO$_2$R14, SO$_2$NHR14, SO$_2$N(R14)$_2$, SO$_2$N(R14)$_3$$^+$X$^-$ (where R14 is a functional group less than or equal to 100000 daltons and X is a charge balancing ion): M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, suibstituted alkynyl, protein or biomolecule or functional group less than or equal to 100000 daltons.

Still another family of compounds has the following structure:

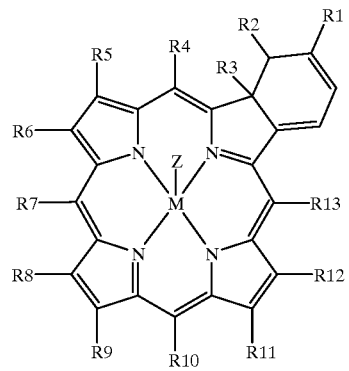

where each of R1 and R2 is CO$_2$R14 (where R14 is alkyl or aryl), CO$_2$H (or a salt therof), SO$_2$Ph, or CN;

R3, R6 R8, and R12 are Me.

R5 is CH=CH$_2$, or CH(OR14)CH$_3$ (where R14 is alkyl or aryl)

R4, R7, R13, R10 are H

R9, R11 are CH$_2$CH$_2$CO$_2$R15 (where R15 is alkyl or H or a salt of the carboxylic acid)

M is In$^{113}$, In$^{115}$ or a mixture of In$^{113}$ and In$^{115}$; Z is a halide, acetate, OH.

M can also be Ag, Al, Ce, Co, Cr, Cu, Dy, Er, Fe, Ga, Hf, Ho, La, Lu, Mo, Nd, Pb, Pd, Pr, Pt, Rh, Sb, Sc, Sm, Tb, Th, Ti, Tl, Tm, U, V, Y, Yb or Zr, preferably Pd, Pt, Ga, Al, Ru, Sn or Zn.

Still another family of compounds has the following structure:

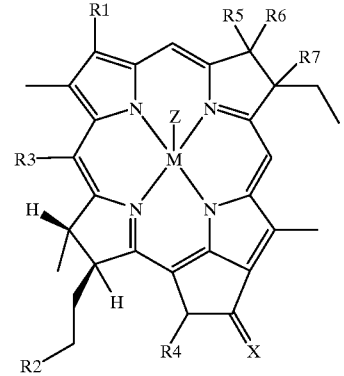

where each of R1–R7 is CH$_2$CH$_3$, CH=CH$_2$, CH=CHCH$_2$N(CH$_3$)$_2$, CH=CHCH$_2$N$^+$ (CH$_3$)$_3$X$^-$ (where X is a charge balancing ion), C(X)$_2$C(X)$_3$ (where X is a halogen), CHO, OR8 or is a functional group less than or equal to 100000 daltons), CH$_2$CO$_2$R8, CH$_2$CONHR8, CH=CHCH$_2$OH, CH=CHCH$_2$OR8, CH(OH)CH$_3$, CH(OR8)CH$_3$, H, halide, alkyl, cyclic alkyl (3–6 carbons), aryl, substituted aryl, alkenyl, substituted alkenyl, alkynyl, substituted alkynyl, amide, ester, NR8R8, CN, OH, OR8, CHO, (CH$_2$)$_n$OH, (CH$_2$)$_n$SH, (CH$_2$)$_n$O-alkoxy, (CH$_2$)$_n$SR8, (CH$_2$)$_n$OR8 (where n=1, 2, 3, 4, and R8 is a functional group less than or equal to 100000 daltons), (CH$_2$)$_n$CO$_2$R8 (where R8 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR8$, $(CH_2)_nCON(R8)_2$, $CO_2R8$, $CONHR8$, $CONR8R8$, $SR8$ (where R8 is a functional group less than or equal to 100000 daltons), $SO_3H$, $SO_3R8$, $SO_2NHR8$, $SO_2N(R8)_2$, $SO_2N(R8)_3{}^+X^-$ (where R8 is a functional group less than or equal to 100000 daltons and X is a charge balancing ion), protein or biomolecule or functional group less than or equal to 100000 daltons; X is O, $H_2$, (H, OH), S, (H, OR8) or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, La, Lu, Mo, Nd, Pb, Pd, Pr, Pt, Rh, Sb, Sc, Sm, Th, Tb, Ti, Tl, Tm, U, V, Y, Yb or Zr, preferably Pd, Pt, Ga, Al or Ru.

Still another family of compounds has the following structure:

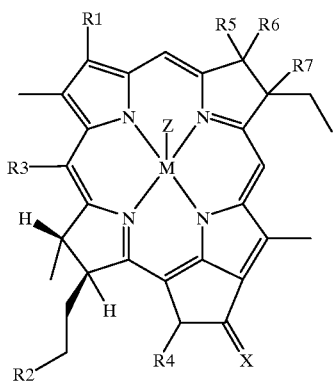

wherein;

R1 =$COCH_3$

R3 and R5=H, $CH_3$

R7=H or OH

R6=Me or OH

R4=H or $CO_2CH_3$

R2=$CO_2R8$ (where R8 is alkyl)

M is $In^{113}$, $In^{115}$ or a mixture of $In^{113}$ and $In^{115}$

Z is a halide, acetate, or OH.

X=O

M can also be Ag, Al, Ce, Co, Cr, Cu, Dy, Er, Fe, Ga, Hf, Ho, La, Lu, Mo, Nd, Pb, Pd, Pr, Pt, Rh, Sb, Sc, Sm, Tb, Th, Ti, Tl, Tm, U, V, Y, Yb or Zr, preferably Pd, Pt, Ga, Al or Ru.

Another family of compounds has the structure:

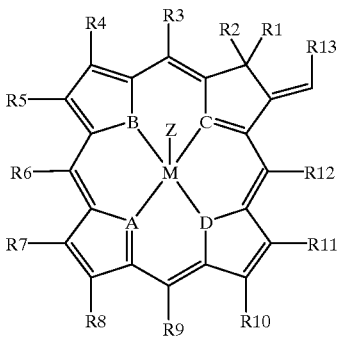

wherein each of R1–R13 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3 X^-$ (where X is a charge balancing ion), $C(X)_2C(X)_3$ (where X is a halogen), NR14R14, CN, OH, OR14, CHO, $(CH_2)_nOH$, $(CH_2)_nSH$, $(CH_2)_nO$-alkoxy, $CH(OH)CH_3$, $CH(OR14)CH_3$, $(CH_2)_nSR14$, $(CH_2)_nOR14$ (where n=1, 2, 3, 4, and R14 is a functional group less than or equal to 100000 daltons), $(CH_2)_nCO_2R14$ (where R14 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR14$, $(CH_2)_nCON(R14)_2$, $CO_2R14$, $CONHR14$, CONR14R14, SR14 (where R14 is a functional group less than or equal to 100000 daltons), $SO_3H$, $SO_3R14$, $SO_2NHR14$, $SO_2N(R14)_2$, $SO_2N(R14)_3{}^+X^-$ (where R14 is a functional group less than or equal to 2000 daltons and X is a charge balancing ion); A, B, C, D are; C, N, $O^+$, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sn, Sm, Tb, Th, Ti, Tl, Tm, U, V, Y, Yb, Zn, Zr.

Still another family of compounds has the following structure:

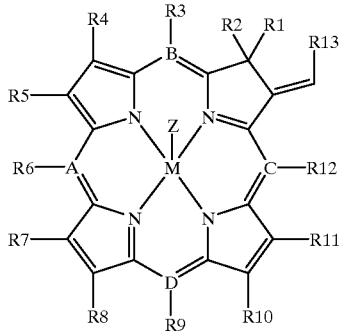

were each of R1–R13 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3X^-$ (where X is a charge balancing ion), $C(X)_2C(X)_3$ (where X is a halogen), NR14R14, CN, OH, OR14, CHO, $(CH_2)_nOH$, $(CH_2)_nSH$, $(CH_2)_nO$-alkoxy, $CH(OH)CH_3$, $CH(OR14)CH_3$, $(CH_2)_nSR14$, $(CH_2)_nOR14$ (where n=1, 2, 3, 4, and R14 is a functional group less than or equal to 100000 daltons), $(CH_2)_nCO_2R14$ (where R14 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR14$, $(CH_2)_nCON(R14)_2$, $CO_2R14$, $CONHR14$, CONR14R14, SR14 (where R14 is a functional group less than or equal to 100000 daltons), $SO_3H$, $SO_3R14$, $SO_2NHR14$, $SO_2N(R14)_2$, $SO_2N(R14)_3{}^+X^-$ (where R14 is a functional group less than or equal to 100000 daltons and X is a charge balancing ion); A, B, C, D are; C, N, $O^+$, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, La, Lu, Mo, Mg, Nd, Pb, Pd, Pr, Pt, Rh, Sb, Sc, Sn, Sm, Tb, Th, Ti, Tl, Tm, U, V, Y, Yb, Zn or Zr.

Another family of compounds has the following structure:

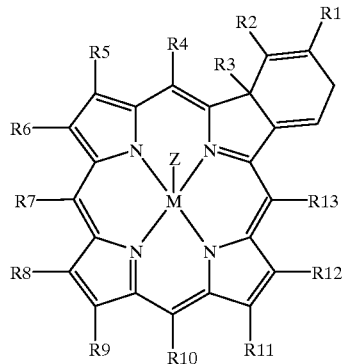

were each of R1–R13 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3X^-$ (where X is a charge balancing ion), $C(X)_2C(X)_3$ (where X is a halogen), NR14R14, CN, OH, OR14, CHO, $(CH_2)_nOH$, $(CH_2)_nSH$, $(CH_2)_nO$-alkoxy, $CH(OH)CH_3$, $CH(OR14)CH_3$ $(CH_2)_nSR14$, $(CH_2)_nOR14$ (where n=1, 2, 3, 4, and R14 is a functional group less than or equal to 100000 daltons), $(CH_2)_nCO_2R14$ (where R14 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR14$, $(C_2)_nCONH(R14)_2$, $CO_2R14$, CONHR14, CONR14R14, SR14 (where R14 is a functional group less than or equal to 100000 daltons), $SO_3H$, $SO_3R_{14}$, $SO_2NHR14$, $SO_2N(R14)_2$, $SO_2N(R14)_3^+X^-$ (where R14 is a functional group less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sn, Sm, Tb, Th, Ti, Tl, Tm, U, V, Y, Yb, Zn or Zr.

Another family of compounds has the following structure:

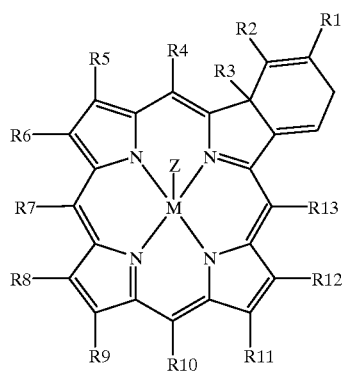

Where each of R1 and R2 is $CO_2R14$ (where R14 is alkyl or aryl), $CO_2H$ (or a salt thereof), $SO_2Ph$, CN or a combination thereof;

Each of R3, R6, R8, R12 is Me.

R5 is $CH=CH_2$, or $CH(OR14)CH_3$ (where R14 is alkyl or aryl)

Each of R4, R7, R13, R10 is H

R9 and R11 are $CH_2CH_2CO_2R15$ (where R15 is alkyl or H or a salt of the carboxylic acid).

M is $In^{113}$, $In^{115}$ or a mixture of $In^{113}$ and $In^{115}$.

Z is a halide, acetate, or OH.

M can also be Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sm, Sn, Tb, Th, Ti, Tl, Tm, U, V, Y, Yb, Zn or Zr, preferably Pd, Pt, Ga, Al, Ru, Sn or Zn.

Another family of compounds has the following structure:

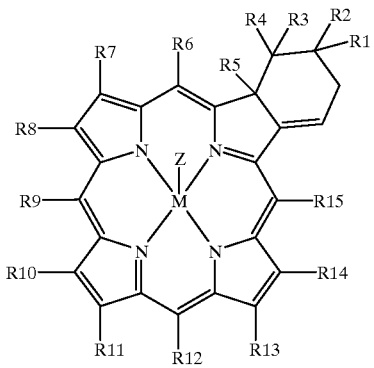

where each of R1–R15 is H, halide, alkyl, vinyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+$ $(CH_3)_3X^-$ (where X is a charge balancing ion), $C(X)_2C(X)_3$ (where X is a halogen), NR16R16, CN, OH, OR16, CHO, $COCH_3$, $(CH_2)_nOH$, $(CH_2)_nSH$, $(CH_2)_nO$-alkoxy, $SO_2Ph$, $CH(OH)CH_3$, $CH(OR14)CH_3$ $(CH_2)_nSR16$, $(CH_2)_nOR16$ (where n=1, 2, 3, 4, and R16 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR16$, $(CH_2)_nCON(R16)_2$, $CO_2R16$, CONHR16, CONR16R16, SR16 (where R16 is a functional group less than or equal to 100000 daltons), $SO_3X$, $SO_3R16$, $SO_2NHR16$, $SO_2N(R16)_2$, $SO_2N(R16)_3^+X^-$ (where R16 is a functional group less than or equal to 100000 daltons and X is a charge balancing ion); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sm, Sn, Tb, Th, Ti, Tl, Tm, U, V, Y, Yb, Zn or Zr, preferably Pd, Pt, Ga, Al, Ru, Sn or Zn.

Another family of compounds has the following structure:

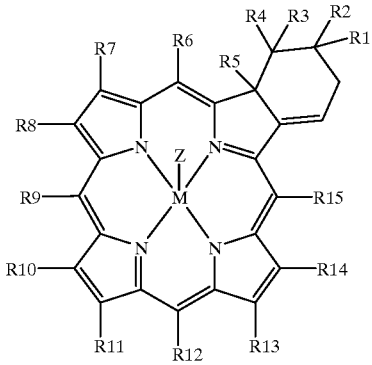

where each of R1, R2, R3 and R4 is CO₂R16 (where R16 is alkyl or aryl), CO₂H (or a salt thereof) or SO₂Ph, CN;
Each of R5, R8, R10 and R14 is Me.
R7 is CH=CH₂ or CH(OR16)CH₃ (where R16 is alkyl or aryl)
Each of R6, R9, R12 and R15 is H
Each of R11 and R13 is CH₂CH₂CO₂R16 (where R16 is alkyl or H or a salt of the carboxylic acid), or an amide
M is $In^{113}$, $In^{115}$ or a mixture of $In^{113}$ and $In^{115}$
Z is a halide, acetate, or OH.
M can also be Ag, Al, Ce, Co, Cr, Cu, Dy, Er, Fe, Ga, Hf, Ho, La, Lu, Mo, Mg, Nd, Pb, Pd, Pr, Pt, Rh, Sb, Sc, Sm, Tb, Th, Ti, Tl, Tm, U, V, Y, Yb or Zr, preferably Pd, Pt, Ga, Al, Ru, Sn or Zn.

Still another family of compounds has the following structure:

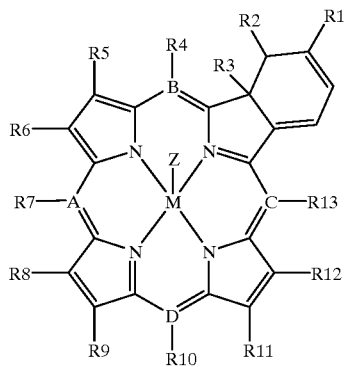

Where each of R1–R13 is H, halide, alkyl, cyclic alkyl (3–6 carbons), aryl, substituted aryl, alkenyl, substituted alkenyl, alkynyl, substituted alkynyl, amide, ester, CH=CHCH₂N(CH₃)₂, CH=CHCH₂N⁺(CH₃)₃X⁻ (where X is a charge balancing ion), C(X)₂C(X)₃ (where X is a halogen), NR14R14, CN, OH, OR14, CHO, (CH₂)$_n$OH, (CH₂)$_n$SH, (CH₂)$_n$O-alkoxy, CH(OH)CH₃, CH(OR14)CH₃ (CH₂)$_n$SR14, (CH₂)$_n$OR14 (where n=1, 2, 3, 4, and R14 is a functional group less than or equal to 100000 daltons), (CH₂)$_n$CO₂R14 (where R14 is H, a physiologically acceptable salt, alkyl (1–6 carbons), aryl, substituted aryl, alkenyl, substituted alkenyl, alkynyl, or substituted alkynyl, and n=1, 2, 3, 4), (CH₂)$_n$CONHR14, (CH₂)$_n$CON(R14)₂, CO₂R14, CONHR14, CONR14R14, SR14 (where R14 is a functional group less than or equal to 100000 daltons), SO₃H, SO₃R14, SO₂NHR14, SO₂N(R14)₂, SO₂N(R14)₃⁺X⁻ (where R14 is a functional group less than or equal to 100000 daltons and X is a charge balancing ion); A, B, C, D are; C, N, O⁺, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sm, Sn, Tb, Th, Ti, Tl, Tm, U, V, Y, Yb, Zn or Zr, preferably Pd, Pt, Ga, Al, Ru, Sn or Zn.

Another family of compounds has the structure:

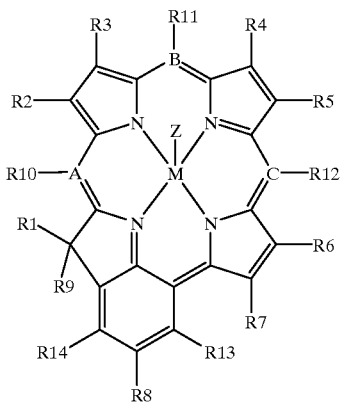

Where each of R1–R14 is H, halide, alkyl, cyclic alkyl (3–6 carbons), aryl, substituted aryl, alkenyl, substituted alkenyl, alkynyl, substituted alkynyl, amide, ester, CH=CHCH₂N(CH₃)₂, CH=CHCH₂N⁺(CH₃)₃X⁻ (where X is a charge balancing ion), C(X)₂C(X)₃ (where X is a halogen), NR15R15, CN, OH, OR15, CHO, (CH₂)$_n$OH, (CH₂)$_n$SH, (CH₂)$_n$O-alkoxy, CH(OH)CH₃, CH(OR15)CH₃ (CH₂)$_n$SR15, (CH₂)$_n$OR15 (where n=1, 2, 3, 4, and R15 is a functional group less than or equal to 100000 daltons), (CH₂)$_n$CO₂R15 (where R15 is H, a physiologically acceptable salt, alkyl (1–6 carbons), aryl, substituted aryl, alkenyl, substituted alkenyl, alkynyl, or substituted alkynyl, and n=1, 2, 3, 4), (CH₂)$_n$CONHR15, (CH₂)$_n$CON(R15)₂, CO₂R15, CONHR15, CONR15R15, SR15 (where R15 is a functional group less than or equal to 100000 daltons), SO₃H, SO₃R15, SO₂NHR15, SO₂N(R15)₂, SO₂N(R15)₃⁺X⁻ (where R15 is a functional group less than or equal to 100000 daltons and X is a charge balancing ion); A, B, C, D are; C, N, O⁺, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, La, Lu, Mo, Mg, Nd, Pb, Pd, Pr, Pt, Rh, Sb, Sc, Sm, Sn, Tb, Th, Ti, Tl, Tm, U, V, Y, Yb, Zn or Zr.

Another family of compounds has the following structure:

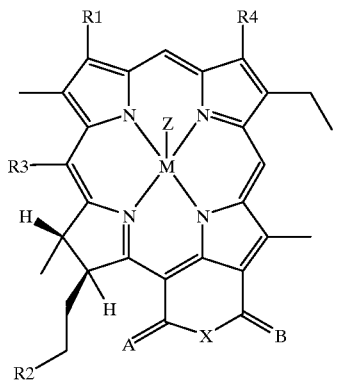

Where each of R1–R4 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R5$, CONHR5, $CH=CHCHO$, $CH_2Y$, (where Y=H, halogen, OH, OR5 or is a functional group less than or equal to 100000 daltons), $CH_2CO_2R5$, $CH_2CONHR5$, $CH=CHCH_2OH$, $CH=CHCH_2OR5$, $CH(OH)CH_3$, $CH(OR5)CH_3$, H, halide, alkyl, cyclic alkyl (3–6 carbons), aryl, substituted aryl, alkenyl, substituted alkenyl, alkynyl, substituted alkynyl, amide, ester, NR5R5, CN, OH, OR5, CHO, $(CH_2)_nOH$, $(CH_2)_nSH$, $(CH_2)_n$O-alkoxy, $(CH_2)_nSR5$, $(CH_2)_nOR5$ (where n=1, 2, 3, 4, and R5 is a functional group less than or equal to 100000 daltons), $(CH_2)_nCO_2R5$ (where R5 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR5$, $(CH_2)_nCON(R5)_2$, $CO_2R5$, CONHR5, CONR5R5, SR5 (where R5 is a functional group less than or equal to 100000 daltons), $SO_3H$, $SO_3R5$, $SO_2NHR5$, $SO_2N(R5)_2$, $SO_2N(R5)_3{}^+X^-$ (where R5 is a functional group less than or equal to 100000 daltons and X is a charge balancing ion), protein or biomolecules or functional groups less than or equal to 100000 daltons; A and B are O, NH, NR5 or combinations thereof; X is, O, NR5 (where R5 is H, alkyl (1–10 carbons), aryl, substituted aryl, alkenyl, substituted alkenyl, alkynyl, substituted alkynyl, an amino acid, an amino acid ester or a functional group less than or equal to 100000 daltons); M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Al, Ce, Co, Cr, Cu, Dy, Er, Fe, Ga, Hf, Ho, La, Lu, Mo, Mg, Nd, Pb, Pd, Pr, Pt, Rh, Sb, Sc, Sm, Tb, Th, Ti, Tl, Tm, U, V, Y, Yb or Zr, preferably Pd, Pt, Ga, Al, Ru, Sn or Zn.

Another family of compounds has the following structure:

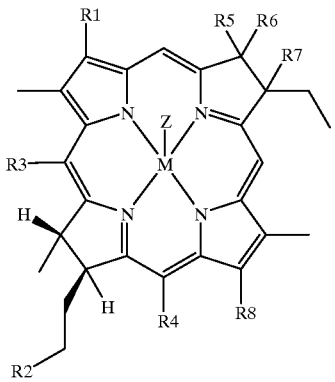

Where each of R1–R8 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R9$, CONHR9, $CH=CHCHO$, $CH_2Y$, (where Y=H, halogen, OH, OR9 or is a functional group less than or equal to 100000 daltons), $CH_2CO_2R9$, $CH_2CONHR9$, $CH=CHCH_2OH$, $CH=CHCH_2OR9$, $CH(OH)CH_3$, $CH(OR9)CH_3$, H, halide, alkyl, cyclic alkyl (3–6 carbons), aryl, substituted aryl, alkenyl, substituted alkenyl, alkynyl, substituted alkynyl, amide, ester, NR9R9, CN, OH, OR9, CHO, $(CH_2)_nOH$, $(CH_2)_nSH$, $(CH_2)_n$O-alkoxy, $(CH_2)_nSR9$, $(CH_2)_nOR9$ (where n=1, 2, 3, 4, and R9 is a functional group less than or equal to 100000 daltons), $(CH_2)_nCO_2R9$ (where R9 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR9$, $(CH_2)_nCON(R9)_2$, $CO_2R9$, CONHR9, CONR9R9, SR9 (where R9 is a functional group less than or equal to 100000 daltons), $SO_3H$, $SO_3R9$, $SO_2NHR9$, $SO_2N(R9)_2$, $SO_2N(R9)_3{}^+X^-$ (where R9 is a functional group less than or equal to 100000 daltons and X is a charge balancing ion), protein or biomolecule or functional group less than or equal to 100000 daltons; X is O, $H_2$, (H, OH), (H, OR9), S, or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkyinyl, protein or biomolecule or functional group less than or equal to 100000 daltons.

M can also be Ag, Ce, Co, Cr, Cu, Dy, Er, Fe, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the following structure:

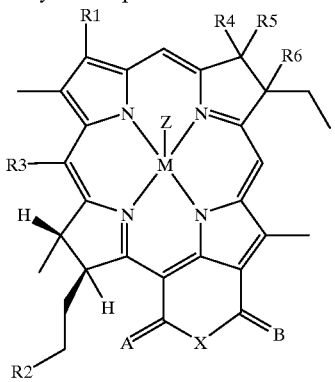

Where each of R1–R6 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R7$, CONHR7, CH=CHCHO, $CH_2Y$, (where Y=H, halogen, OH, OR7 or is a functional group less than or equal to 100000 daltons), $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, OH, OR7, CHO, $(CH_2)_nOH$, $(CH_2)_nSH$, $(CH_2)_nO$-alkoxy, $(CH_2)_nSR7$, $(CH_2)_nOR7$ (where n=1, 2, 3, 4, and R7 is a functional group less than or equal to 100000 daltons), $(CH_2)_nCO_2R7$ (where R7 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR7$, $(CH_2)_nCON(R7)_2$, $CO_2R7$, CONHR7, CONR7R7, SR7 (where R7 is a functional group less than or equal to 100000 daltons), $SO_3H$, $SO_3R7$, $SO_2NHR7$, $SO_2N(R7)_2$, $SO_2N(R7)_3{}^+X^-$ (where R7 is a functional group less than or equal to 100000 daltons and X is a charge balancing ion), protein or biomolecule or functional group less than or equal to 100000 daltons; X is, O, NR7 (where R7 is H, alkyl (1–10 carbons), aryl, substituted aryl, alkenyl, substituted alkenyl, alkynyl, substituted alkynyl, an amino acid, an amino acid ester or a functional group less than or equal to 100000 daltons); A and B are O, NH, NR7 or combinations thereof; M is $In^{113}$, $In^{115}$ or a mixture of $In^{113}$ and $In^{115}$; Z is a halide, acetate, OH, alkyl, thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the following structure:

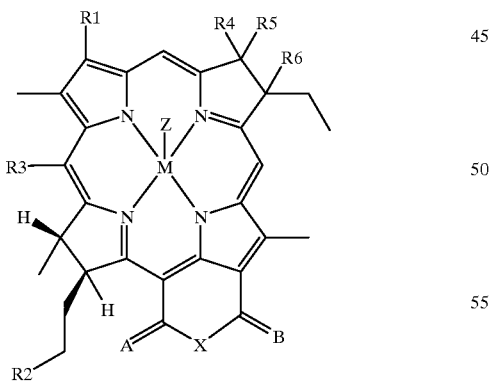

wherein;

R1 is $CH=CH_2$, Et, CHO, or $COCH_3$

R2 is $CO_2CH_3$, $CO_2H$, $CO_2R7$ (R7 is an alkyl, phenyl), or an amide

R3 is H

R4 is Me

Each of R5 and R6 is OH

Each of A and B is O or NR7 (R7 is alkyl).

X is O or NR7 (R7 is alkyl, an amino acid, an alcohol containing group, or an ether containing group)

M is $In^{113}$, $In^{115}$ or a mixture of $In^{113}$ and $In^{115}$

Z is a halide, acetate, or OH.

M can also be Ag, Al, Ce, Co, Cr, Cu, Dy, Er, Fe, Ga, Hf, Ho, La, Lu, Mo, Mg, Nd, Pb, Pr, Rh, Sb, Sc, Sm, Tb, Th, Ti, Tl, Tm, U, V, Y, Yb or Zr, preferably Pd, Pt, Ga, Al, Ru, Sn or Zn.

Another family of compounds has the following structure:

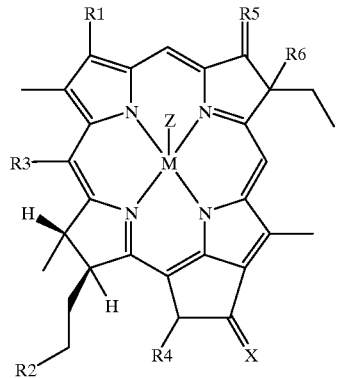

where each of R1–R6 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R7$, CONHR7, CH=CHCHO, $CH_2Y$, (where Y=H, halogen, OH, OR7 or is a functional group less than or equal to 100000 daltons), $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, $(CH_2)_nOH$, $(CH_2)_nSH$, $(CH_2)_nO$-alkoxy, $(CH_2)_nSR7$, $(CH_2)_nOR7$ where n=1, 2, 3, 4, and R7 is a functional group less than or equal to 100000 daltons), $(CH_2)_nCO_2R7$ (where R7 is H, a physiologically acceptable salt, alkyl (1–6 carbons), aryl, substituted aryl, alkenyl, alkynyl or substituted alkynyl, and n=1, 2, 3, 4), $(CH_2)_nCONR7$, $CO_2R7$, CONHR7, CONR10R7, SR7 (where R7 is a functional group less than or equal to 100000 daltons), $SO_3H$, $SO_3R7$, $SO_2NHR7$, $SO_2N(R7)_2$, $SO_2N(R7)_3{}^+X^-$ (where R7 is a functional group less than or equal to 100000 daltons and X is a charge balancing ion), protein or biomolecule or functional group less than or equal to 100000 daltons; X is O, $H_2$, (H, OH), (H, OR8) S, or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn,.

Another family of compounds has the following structure:

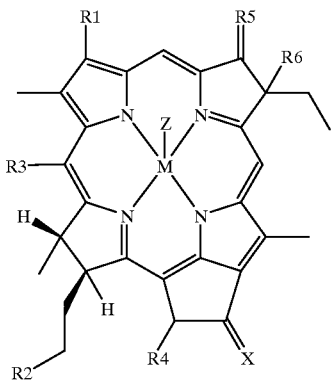

wherein;

R1 is CH=CH$_2$, Et, CHO, or COCH$_3$

R2 is CO$_2$CH$_3$, CO$_2$H, CO$_2$R7 (R7 is an alkyl or phenyl group), or an amide R3 is H R4 is H or CO$_2$CH$_3$ R5 is O, or NR7 (where R7 is alkyl)

R6 is Me

X is O

M is In$^{113}$, In$^{115}$ or a mixture of In$^{113}$ and In$^{115}$

Z is a halide, acetate or OH.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the following structure:

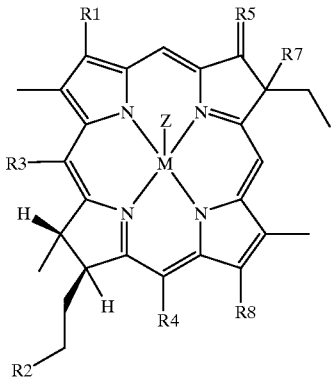

where each of R1–R8 is CH$_2$CH$_3$, CH=CH$_2$, CH=CHCH$_2$N(CH$_3$)$_2$, CH=CHCH$_2$N$^+$(CH$_3$)$_3$X$^-$ (where X is a charge balancing ion), C(X)$_2$C(X)$_3$ (where X is a halogen), CHO, COCH$_3$, CO$_2$H, CO$_2$R9, CONHR9, CH=CHCHO, CH$_2$Y, (where Y=H, halogen, OH, OR9 or is a functional group less than or equal to 100000 daltons), CH$_2$CO$_2$R9, CH$_2$CONHR9, CH=CHCH$_2$OH, CH=CHCH$_2$OR9, CH(OH)CH$_3$, CH(OR9)CH$_3$, H, halide, alkyl, cyclic alkyl (3–6 carbons), aryl, substituted aryl, alkenyl, substituted alkenyl, alkynyl, substituted alkynyl, amide, ester, NR9R9, CN, O, S, NHR9, OH, OR9, CHO, (CH$_2$)$_n$OH, (CH$_2$)$_n$SH, (CH$_2$)$_n$O-alkoxy, (CH$_2$)$_n$SR9, (CH$_2$)$_n$OR9 (where n=1, 2, 3, 4, and R9 is a functional groups less than or equal to 100000 daltons), (CH$_2$)$_n$CO$_2$R9 (where R9 is H, a physiologically acceptable salt, alkyl (1–6 carbons), aryl, substituted aryl, alkenyl, substituted alkenyl, alkynyl, or substituted alkynyl, and n=1, 2, 3, 4), (CH$_2$)$_n$CONHR9, (CH$_2$)$_n$CON(R9)$_2$, CO$_2$R9, CONHR9, CONR10R9, SR9 (where R9 is a functional groups less than or equal to 100000 daltons), SO$_3$H, SO$_3$R9, SO$_2$NHR9, SO$_2$N(R9)$_2$, SO$_2$N(R9)$_3$$^+$X$^-$ (where R9 is a functional groups less than or equal to 100000 daltons and X is a charge balancing ion), protein or biomolecule or functional group less than or equal to 100000 daltons; M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, substituted alkynyl, a protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Still another family of compounds has the following structure:

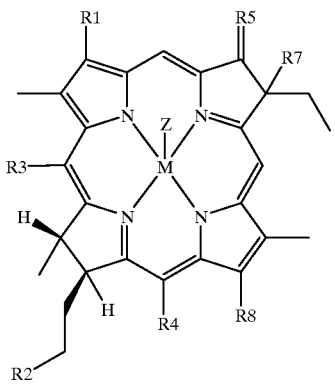

wherein;

R1 is CH=CH$_2$, Et, CHO, or COCH$_3$

R5 is O or NR7 (where R7 is alkyl)

R7 is Me

R3 is H

R4 and R8 are H, CO$_2$CH$_3$, CO$_2$H (or a salt thereof), CO$_2$R7 (R7 is an alkyl or phenyl group), an amide, CH$_2$CO$_2$CH$_3$, CH$_2$CO$_2$H (or a salt thereof), CO$_2$R9 (R9 is an alkyl or a phenyl group), or an amide R2 is CO$_2$CH$_3$, CO$_2$H, CO$_2$R9 (R9 is an alkyl or phenyl group), or an amide M is In$^{113}$, In$^{115}$ or a mixture of In$^{113}$ and In$^{115}$ Z is a halide, acetate, or OH.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the following structure:

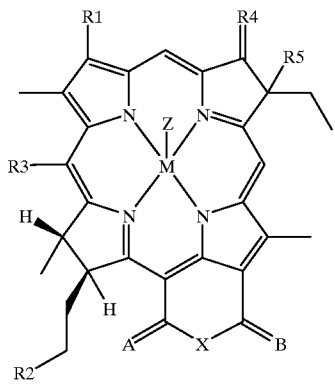

where each of R1–R5 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R6$, CONHR6, $CH=CHCHO$, $CH_2Y$, (where Y=H, halogen, OH, OR6 or is a functional group less than or equal to 100000 daltons), $CH_2CO_2R6$, $CH_2CONHR6$, $CH=CHCH_2OH$, $CH=CHCH_2OR8$, $CH(OH)CH_3$, $CH(OR6)CH_3$, H, halide, alkyl, cyclic alkyl (3–6 carbons), aryl, substituted aryl, alkenyl, substituted alkenyl, alkynyl, substituted alkynyl, amide, ester, NR6R6, CN, O, S, NHR6, OH, OR6, CHO, $(CH_2)_nOH$, $(CH_2)_nSH$, $(CH_2)_nO$-alkoxy, $(CH_2)_nSR6$, $(CH_2)_nOR6$ (where n=1, 2, 3, 4, and R6 is a functional goroup less than or equal to 100000 daltons), $(CH_2)_nCO_2R6$ (where R6 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONR6$, $CO_2R6$, CONHR6, CONR6R6, SR6 (where R6 is a functional group less than or equal to 100000 daltons), $SO_3H$, $SO_3R6$, $SO_2NHR6$, $SO_2N(R6)_2$, $SO_2N(R6)_3^+X^-$ (where R6 is a functional group less than or equal to 100000 daltons), $SO_3H$, $SO_3R6$, $SO_2NHR6$, $SO_2N(R6)_2$, $SO_2N(R6)_3^+X^-$ (where R6 is a functional group less than or equal to 100000 daltons and X is a charge balancing ion), protein or biomolecule or functional group less than or equal to 100000 daltons; X is O, NR6 (where R6 is H, alkyl (1–10 carbons), aryl, substituted aryl, alkenyl, substituted alkenyl, alkynyl, substituted alkynyl, an amino acid, an amino acid ester or a functional group less than or equal to 100000 daltons); A and B are O, NH, NR6 or combinations thereof; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, S or Zn.

Another family of compounds has the following structure:

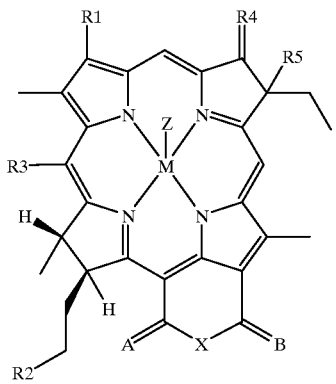

Wherein:

Each of A and B is O or NR6 (where R6 is an alkyl or phenyl group)

R1 is $CH=CH_2$, Et, CHO, or $COCH_3$

R4 is O or NR6 (where R6 is alkyl)

R5 is Me

R3 is H

R2 is $CO_2CH_3$, $CO_2H$, $CO_2R6$ (R6 is an alkyl or phenyl group), or an amide X is O, NR6 (R6 is alkyl, an amino acid, an alcohol containing group, or an ether containing group)

M is $In^{113}$, $In^{115}$ or a mixture of $In^{113}$ and $In^{115}$

Z is a halide, acetate, OH.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the following structure:

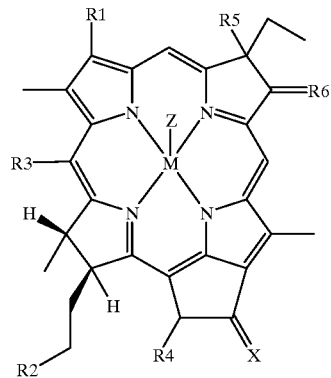

Where each of R1–R6 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R7$, CONHR7, $CH=CHCHO$, $CH_2Y$, (where Y=H, halogen, OH, OR7 or is a functional group less than or equal to 100000 daltons), $CH_2CO_2R7$, $CH_2CONHR7$, $CH=CHCH_2OH$, $CH=CHCH_2OR7$, $CH(OH)CH_3$, CH(OR7)CH₃, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, (CH₂)ₙOH, (CH₂)ₙSH, (CH₂)ₙO-alkoxy, (CH₂)ₙSR7, (CH₂)ₙOR7 (where n=1, 2, 3, 4, and R7 is a functional groups less than or equal to 100000 daltons), (CH₂)ₙCO₂R7 (where R7 is H, a physiologically acceptable salt, alkyl (1–6 carbons), aryl, substituted aryl, alkenyl, substituted alkenyl, alkynyl, or substituted alkynyl, and n=1, 2, 3, 4), (CH₂)ₙCONR7, CO₂R7, CONHR7, CONR7R7, SR7 (where R7 is a functional group less than or equal to 100000 daltons), SO₃H, SO₃R7, SO₂NHR7, SO₂N(R7)₂, SO₂N(R7)₃⁺X⁻ where R7 is a functional group less than or equal to 100000 daltons and X is a charge balancing ion), protein or biomolecule or functional group less than or equal to 100000 daltons; X is O, H₂, (H, OH), (H, OR7), S, or a ketone protecting group; M is In¹¹³, In¹¹⁵ or a mixture of In¹¹³ and In¹¹⁵; Z is a halide, acetate, OH, alkyl, aryl, substituted aryl, alkenyl, substituted alkenyl, alkynyl, substituted alkynyl, protein or biomolecules or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Ti, Tm, U, V, Y, Yb or Zr, preferably Pd, Pt, Ga, Al, Ru, Sn or Zn.

Another family of compounds has the structure:

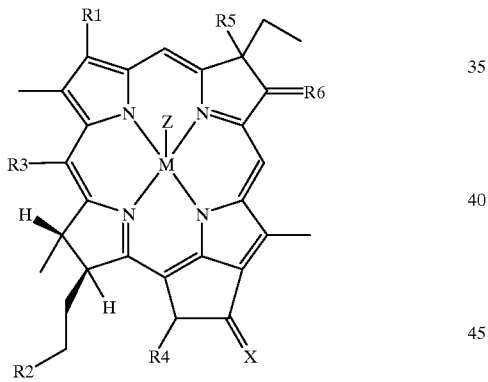

wherein;

R1 is CH=CH₂, Et, CHO, or COCH₃

R6 is O or NR7 (where R7 is an alkyl group)

R5 is Me

R3 is H

R4 is H or CO₂CH₃

R2 is CO₂CH₃, CO₂H, CO₂R7 (R7 is an alkyl, phenyl), or an amide

X is O

M is In¹¹³, In¹¹⁵ or a mixture of In¹¹³ and In¹¹⁵

Z is a halide, acetate, or OH.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the structure:

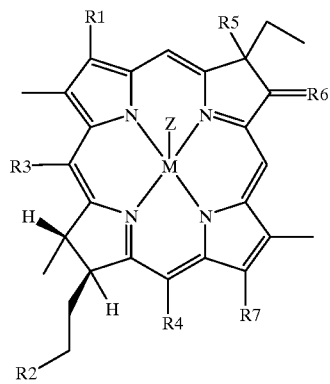

Where each of R1–R7 is CH₂CH₃, CH=CH₂, CH=CHCH₂N(CH₃)₂, CH=CHCH₂N⁺(CH₃)₃X⁻ (where X is a charge balancing ion), C(X)₂C(X)₃ (where X is a halogen), CHO, COCH₃, CO₂H, CO₂R8, CONHR8, CH=CHCHO, CH₂Y, (where Y=H, halogen, OH, OR8 or is a functional group less than or equal to 100000 daltons), CH₂CO₂R8, CH₂CONHR8, CH=CHCH₂OH, CH=CHCH₂OR8, CH(OH)CH₃, CH(OR8)CH₃, H, halide, alkyl, cyclic alkyl (3–6 carbons), aryl, substituted aryl, alkenyl, substituted alkenyl, alkynyl, substituted alkynyl, amide, ester, NR8R8, CN, O, S, NHR8, OH, OR8, CHO, (CH₂)ₙOH, (CH₂)ₙSH, (CH₂)ₙO-alkoxy, (CH₂)ₙSR8, (CH₂)ₙOR8 (where n=1, 2, 3, 4, and R8 is a functional groups less than or equal to 100000 daltons), (CH₂)ₙCO₂R8 (where R8 is H, a physiologically acceptable salt, alkyl (1–6 carbons), aryl, substituted aryl, alkenyl, substituted alkenyl, alkynyl, or substituted alkynyl, and n=1, 2, 3, 4), (CH₂)ₙCONR8, CO₂R8, CONHR8, CONR8R8, SR8 (where R8 is a functional groups less than or equal to 100000 daltons), SO₃H, SO₃R8, SO₂NHR8, SO₂N(R8)₂, SO₂N(R8)₃⁺X⁻ (where R8 is a functional groups less than or equal to 100000 daltons and X is a charge balancing ion), protein or biomolecules or functional groups less than or equal to 100000 daltons; M is In¹¹³, In¹¹⁵ or a mixture of In¹¹³ and In¹¹⁵; Z is a halide, acetate, OH, alkyl, aryl, substituted aryl, alkenyl, substituted alkenyl, alkynyl, substituted alkynyl, protein or biomolecules or functional groups less than or equal to 100000 daltons.

Another family of compounds has the structure:

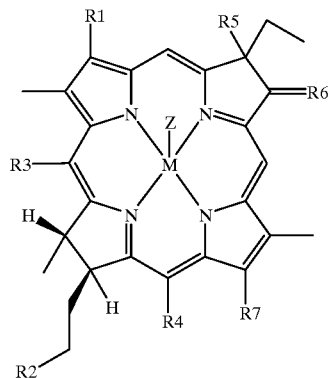

wherein;
R1 is CH=CH$_2$, Et, CHO, or COCH$_3$
R6 is O, or NR8 (where R8 is alkyl)
R5 is Me
R3 is H
R4 and R7 are H, CO$_2$CH$_3$, CO$_2$H (or a salt thereof), CO$_2$R8 (R8 is alkyl or phenyl), an amide, CH$_2$CO$_2$CH$_3$, CH$_2$CO$_2$H (or a salt thereof), CO$_2$R8 (R8 is an alkyl or phenyl group)
R2 is CO$_2$CH$_3$, CO$_2$H, CO$_2$R8 (R8 is alkyl or phenyl), or an amide
M is In$^{113}$, In$^{115}$ or a mixture of In$^{113}$ and In$^{115}$
Z is a halide, acetate, OH.
M can also be Pd Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Another family of compounds has the following structure:

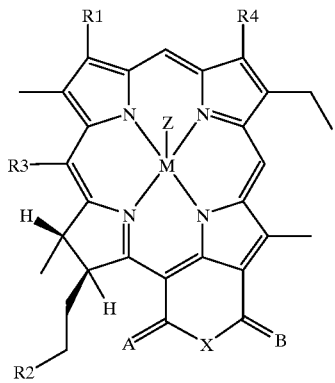

Wherein:
R1 is CH=CH$_2$, Et, CHO or COCH$_3$
R4 is Me
R3 is H
R2 is CO$_2$CH$_3$, CO$_2$H, CO$_2$R5 (R5 is alkyl or phenyl), or an amide
Each of A and B is O or NR5 (R5 is alkyl)
X is O, NR5 (R5 is alkyl, an amino acid, an alcohol containing group, or an ether containing group)
M is In$^{113}$, In$^{115}$ or a mixture of In$^{113}$ and In$^{115}$.
M can also be Ag, Al, Ce, Co, Cr, Cu, Dy, Er, Fe, Ga, Hf, Ho, La, Lu, Mo, Mg, Nd, Pb, Pr, Rh, Sb, Sc, Sm, Tb, Th, Ti, Tl, Tm, U, V, Y, Yb or Zr, preferably Pd, Pt, Ga, Al, Ru, Sn or Zn.

Another family of compounds has the structure:

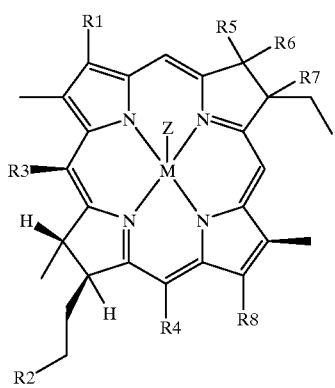

Wherein:
R1 is CH=CH$_2$, Et, CHO or COCH$_3$
Each of R6 and R7 is H or OH
R5 is Me
R4 is CO$_2$CH$_3$, CO$_2$H, CO$_2$R9 (R9 is an alkyl or a phenyl group), an amide, CH$_2$CO$_2$CH$_3$, CH$_2$CO$_2$H, or CH$_2$CO$_2$R9 (R9 is an alkyl or a phenyl group).
R3 is H
each of R2 and R8 is CO$_2$CH$_3$, CO$_2$H, CO$_2$R9 (R9 is an alkyl or a phenyl group), or an amide
M is In$^{113}$, In$^{115}$ or a mixture of In$^{113}$ and In$^{115}$
Z is a halide, acetate, or OH.
M can also be Ag, Ce, Co, Cr, Cu, Dy, Er, Fe, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Still another family of compounds has the structure:

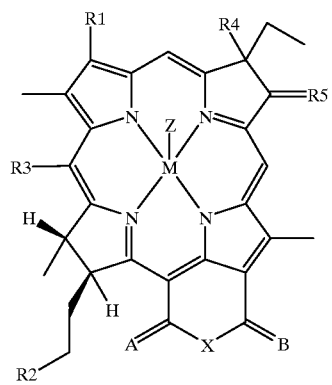

wherein each of R1–R5 is CH$_2$CH$_3$, CH=CH$_2$, CH=CHCH$_2$N(CH$_3$)$_2$, CH=CHCH$_2$N$^+$(CH$_3$)$_3$X$^-$ (where X is a charge balancing ion), C(X)$_2$C(X)$_3$ (where X is a halogen), CHO, COCH$_3$, CO$_2$H, CO$_2$R6, CONHR6, CH=CHCHO, CH$_2$Y, (where Y=H, halogen, OH or OR6 or is a functional group less than or equal to 100000 daltons), CH$_2$CO$_2$R6, CH$_2$CONHR6, CH=CHCH$_2$OH, CH=CHCH$_2$OR6, CH(OH)CH$_3$, CH(OR6)CH$_3$, H, halide, alkyl, cyclic alkyl (3–6 carbons), aryl, substituted aryl, alkenyl, substituted alkenyl, alkynyl, substituted alkynyl, amide, ester, NR6R6, CN, O, S, NHR6, OH, OR6, CHO, (CH$_2$)$_n$OH, (CH$_2$)$_n$SH, (CH$_2$)$_n$O-alkoxy, (CH$_2$)$_n$SR6, (CH$_2$)$_n$OR6 (where n=1, 2, 3, 4, and R6 is a functional group less than or equal to 100000 daltons), (CH$_2$)$_n$CO$_2$R6 (where R6 is H, a physiologically acceptable salt, alkyl (1–6 carbons), aryl, substituted aryl, alkenyl, substituted alkenyl, alkynyl, or substituted alkynyl, and n=1, 2, 3, 4), (CH$_2$)$_n$CONR6, CO$_2$R6, CONHR6, CONR6R6, SR6 (where R6 is a functional group less than or equal to 100000 daltons), SO$_3$H, SO$_3$R6, SO$_2$NHR6, SO$_2$N(R6)$_2$, SO$_2$N(R6)$_3^+$ X$^-$ (where R6 is a functional group less than or equal to 100000 daltons and X is a charge balancing ion), protein or biomolecule or functional group less than or equal to 100000 daltons; A and B are O, NH, NR6 or combinations thereof; X is, O, NR6 (where R6 is H, alkyl (1–10 carbons), aryl, substituted aryl, alkenyl, substituted alkenyl, alkynyl, substituted alkynyl, an amino acid, an amino acid ester or a functional group less than or equal to 100000 daltons); M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Still another family of compounds has the structure:

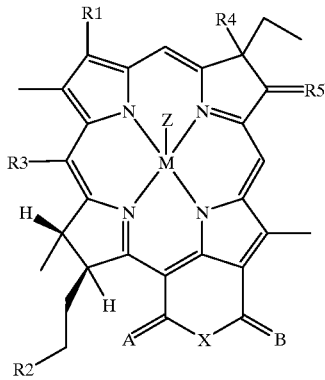

wherein:
R1 is $CH=CH_2$, Et, CHO or $COCH_3$
R5 is O or NR6 (where R6 is alkyl)
R4 is Me
R3 is H
R2 is $CO_2CH_3$, $CO_2H$, $CO_2R5$ (R5 is alkyl or phenyl), or an amide
A and B are O or NR6 (R6 is an alkyl or a phenyl group)
X is O, NR6 (R6 is alkyl), an amino acid, an alcohol containing group, or an ether or amine containing group
M is $In^{113}$, $In^{115}$ or a mixture of $In^{113}$ and $In^{115}$
Z is a halide, acetate, or OH.

M can also be Ag, Ce, Co, Cr, Cu, Dy, Er, Fe, Ga, Hf, Ho, La, Lu, Mo, Mg, Nd, Pb, Pr or Rh, preferably Ga, Al, Ru, Sn or Zn.

Still another family of compounds has the structure:

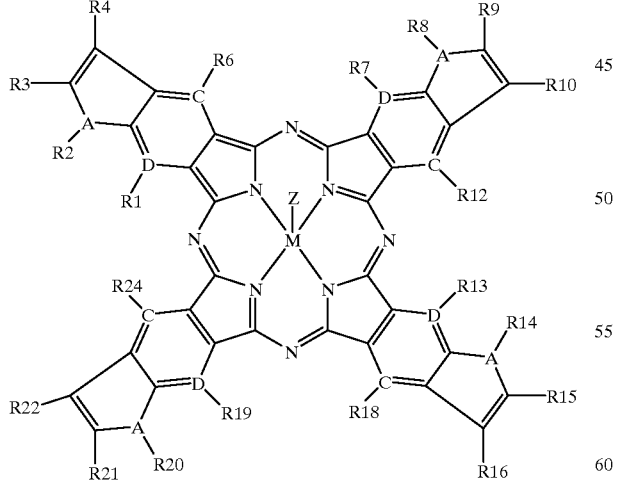

Wherein each of R1–R24 is $CH_2CH_3$, $CH=CHCH_2N(CH_3)_2$, $CH=CHCH_2N^+(CH_3)_3X^-$ (where X is a charge balancing ion), $CH=CH_2$, $C(X)_2C(X)_3$ (where X is a halogen), CHO, $COCH_3$, $CO_2H$, $CO_2R25$, CONHR25, CH=CHCHO, $CH_2Y$, (where Y=H, halogen, OH, OR25 or is a functional group less than or equal to 100000 daltons), $CH_2CO_2R25$, $CH_2CONHR25$, $CH=CHCH_2OH$, $CH=CHCH_2OR25$, $CH(OH)CH_3$, $CH(OR25)CH_3$, H, halide, alkyl, cyclic alkyl (3–6 carbons), aryl, substituted aryl, alkenyl, substituted alkenyl, alkynyl, substituted alkynyl, amide, ester, NR25R25, CN, O, S, NHR25, OH, OR25, CHO, $(CH_2)_nOH$, $(CH_2)_nSH$, $(CH_2)_n$O-alkoxy, $(CH_2)_nSR25$, $(CH_2)_nOR25$ (where n=1, 2, 3, 4, and R25 is a functional group less than or equal to 100000 daltons), $(CH_2)_nCO_2R25$ (where R25 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCON(R25)_2$, $(CH_2)_nCONHR25$, $CO_2R25$, CONHR25, CONR25R25, SR25 (where R25 is a functional group less than or equal to 100000 daltons), $SO_3H$, $SO_3R25$, $SO_2NHR25$, $SO_2N(R25)_2$, $SO_2N(R25)_3^+X^-$ (where R25 is a functional group less than or equal to 100000 daltons and X is a charge balancing ion), protein or biomolecule or functional group less than or equal to 100000 daltons; A, B, C, D are; C, N, $O^+$, O, S, Te, P, $N^+(R25)X^-$ (where R25 is a functional group less than or equal to 100000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl substituted alkynyl, protein or biomolecule or functional group less than or equal to 100000 daltons.

M can also be Pd or Ga.

Yet another family of compounds has the structure:

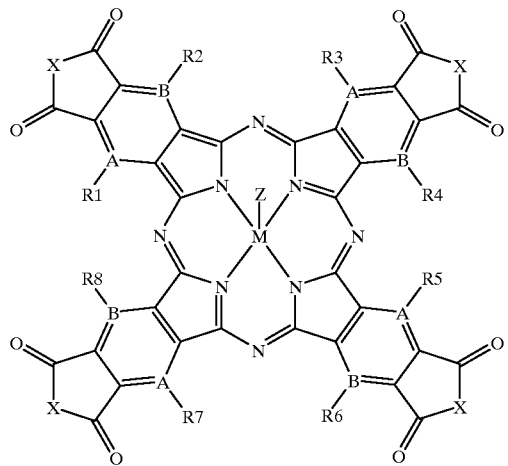

Wherein each of R1–R8 is $CH_2CH_3$, $CH=CH_2$, $CH=CHCH_2N(CH_3)_2$, $CH=CHCH_2N^+(CH_3)_3$ $X^-$ (where X is a charge balancing ion), $C(X)_2C(X)_3$ (where X is a halogen), CHO, $COCH_3$, $CO_2H$, $CO_2R9$, CONHR9, CH=CHCHO, $CH_2Y$, (where Y=H, halogen, OH, OR9 or is a functional group less than or equal to 100000 daltons), $CH_2CO_2R9$, $CH_2CONHR9$, $CH=CHCH_2OH$, $CH=CHCH_2OR9$, $CH(OH)CH_3$, $CH(OR9)CH_3$, H, halide, alkyl, cyclic alkyl (3–6 carbons), aryl, substituted aryl, alkenyl, substituted alkenyl, alkynyl, substituted alkynyl, amide, ester, NR9R9, CN, O, S, NHR9, OH, OR9, CHO, $(CH_2)_nOH$, $(CH_2)_nSH$, $(CH_2)_n$O-alkoxy, $(CH_2)_nSR9$, $(CH_2)_nOR9$ (where n=1, 2, 3, 4, and R9 is a functional group less than or equal to 100000 daltons), $(CH_2)_nCO_2R9$ (where R9 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR9$, $(CH_2)_nCON(R9)_2CO_2R9$, CONHR9, CONR9R9, SR9 (where R9 is a functional group less than or equal to 100000 daltons), $SO_3H$, $SO_3R9$, $SO_2NHR9$, $SO_2N(R9)_2$, $SO_2N(R9)_3{}^+X^-$ (where R9 is a functional group less than or equal to 100000 daltons and X is a charge balancing ion), protein or biomolecule or functional group less than or equal to 100000 daltons.

A, B, C, D are; C, N, $O^+$, O, S, Te, P, $N^+(R9)X^-$ (where R9 is a functional group less than or equal to 100000 daltons and X is a charge balancing ion), or combinations thereof. M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons; X is O, NR9 (where R9 is H, alkyl (1–10 carbons), aryl, substituted aryl, alkenyl, substituted alkenyl, alkynyl, substituted alkynyl, an amino acid, an amino acid ester or a functional group less than or equal to 100000 daltons).

M can also be Pd or Ga.

Yet another family of compounds has the structure:

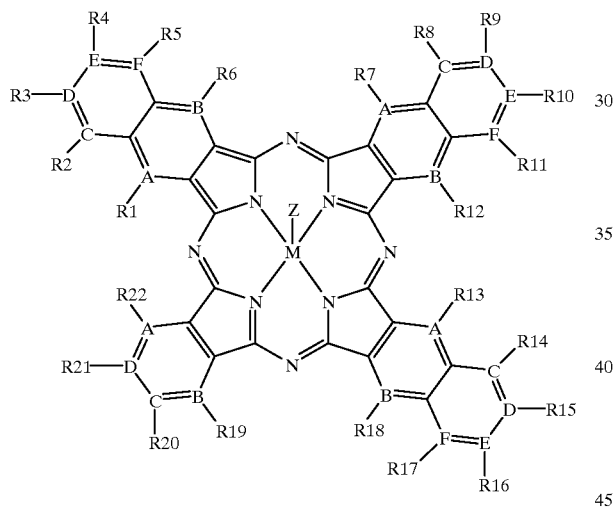

wherein each of R1–R22 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R23$, CONHR23, CH=CHCHO, $CH_2Y$, (where Y=H, halogen, OH, OR23 or is a functional group less than or equal to 100000 daltons), $CH_2CO_2R23$, $CH_2CONHR23$, $CH=CHCH_2OH$, $CH=CHCH_2OR23$, $CH(OH)CH_3$, $CH(OR23)CH_3$, H, halide, alkyl, cyclic alkyl (3–6 carbons), aryl, substituted aryl, alkenyl, substituted alkenyl, alkynyl, substituted alkynyl, amide, ester, NR23R23, CN, O, S, NHR23, OH, OR23, CHO, $(CH_2)_nOH$, $(CH_2)_nSH$, $(CH_2)_nO$-alkoxy, $(CH_2)_nSR23$, $(CH_2)_nOR23$ (where n=1, 2, 3, 4, and R23 is a functional group less than or equal to 100000 daltons), $(CH_2)_nCO_2R23$ (where R23 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR23$, $(CH_2)_nCON(R23)_2$, $CO_2R23$, CONHR23, CONR23R23, SR23 (where R23 is a functional group less than or equal to 100000 daltons), $SO_3H$, $SO_3R23$, $SO_2NHR23$, $SO_2N(R23)_2$, $SO_2N(R23)_3{}^+X^-$ (where R23 is a functional group less than or equal to 100000 daltons and X is a charge balancing ion), protein or biomolecule or functional group less than or equal to 100000 daltons; A, B, C, D, E and F are C, N, $O^+$, O, S, Te, P, $N^+(R23)X^-$ (where R23 is a functional group less than or equal to 2000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga.

Another family of compounds has the structure:

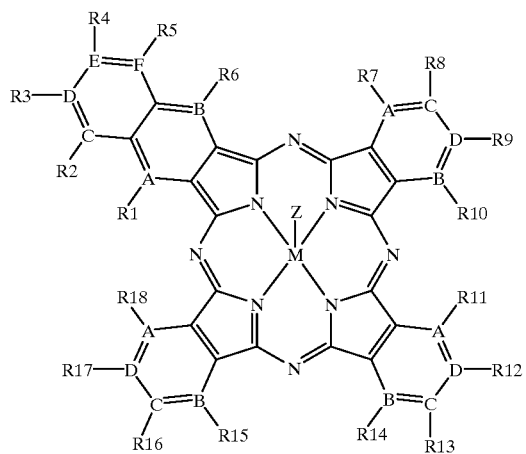

wherein each of R1–R18 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R19$, CONHR19, CH=CHCHO, $CH_2Y$, (where Y=H, halogen, OH, OR19 or is a functional group less than or equal to 100000 daltons), $CH_2CO_2R19$, $CH_2CONHR19$, $CH=CHCH_2OH$, $CH=CHCH_2OR19$, $CH(OH)CH_3$, $CH(OR19)CH_3$, H, halide, alkyl, cyclic alkyl (3–6 carbons), aryl, substituted aryl, alkenyl, substituted alkenyl, alkynyl, substituted alkynyl, amide, ester, NR19R19, CN, O, S, NHR19, OH, OR19, CHO, $(CH_2)_nOH$, $(CH_2)_nSH$, $(CH_2)_nO$-alkoxy, $(CH_2)_nSR19$, or $(CH_2)_nOR19$ (where n=1, 2, 3, 4, and R19 is a functional group less than or equal to 100000 daltons), $(CH_2)_nCO_2R19$ (where R19 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR19$, $(CH_2)_nCON(R19)_2CO_2R19$, CONHR19, CONR19R19, SR19 (where R19 is a functional group less than or equal to 2000 daltons), $SO_3H$, $SO_3R19$, $SO_2NHR19$, $SO_2N(R19)_2$, $SO_2N(R19)_3{}^+X^-$ (where R19 is a functional group less than or equal to 100000 daltons and X is a charge balancing ion), protein or biomolecule or functional group less than or equal to 100000 daltons; A, B, C, D, E, F are CH, N, $O^+$, O, S, Te, P, $N^+(R19)X^-$ (where R19 is a functional group less than or equal to 100000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga.

Another family of compounds has the structure:

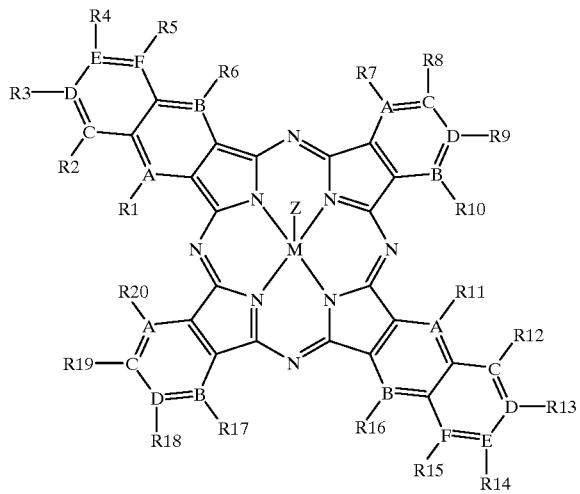

wherein each of R1–R20 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R21$, CONHR21, $CH=CHCHO$, $CH_2Y$, (where Y=H, halogen, OH, OR21 or is a functional group less than or equal to 100000 daltons). $CH_2CO_2R21$, $CH_2CONHR21$, $CH=CHCH_2OH$, $CH=CHCH_2OR21$, $CH(OH)CH_3$, $CH(OR21)CH_3$, H, halide, alkyl, cyclic alkyl (3–6 carbons), aryl, substituted aryl, alkenyl, substituted alkenyl, alkynyl, substituted alkynyl, amide, ester, NR21R21, CN, O, S, NHR21, OH, OR21, CHO, $(CH_2)_nOH$, $(CH_2)_nSH$, $(CH_2)_n$O-alkoxy, $(CH_2)_nSR21$, $(CH_2)_nOR21$ (where n=1, 2, 3, 4, and R21 is a functional group less than or equal to 100000 daltons), $(CH_2)_nCO_2R21$ (where R21 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR21, $(CH_2)_n$CON(R21)$_2$, $CO_2R21$, CONHR21, CONR21R21, SR21 (where R21 is a functional group less than or equal to 100000 daltons), $SO_3H$, $SO_3R21$, $SO_2NHR21$, $SO_2N(R21)_2$, $SO_2N(R21)_3^+X^-$ (where R21 is a functional group less than or equal to 100000 daltons and X is a charge balancing ion), protein or biomolecule or functional group less than or equal to 100000 daltons; A, B, C, D, E, F are: C, N, $O^+$, O, S, Te, P, $N^+(R21)X^-$ (where R21 is a functional group less than or equal to 100000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga.

Still another family of compounds has the following structure:

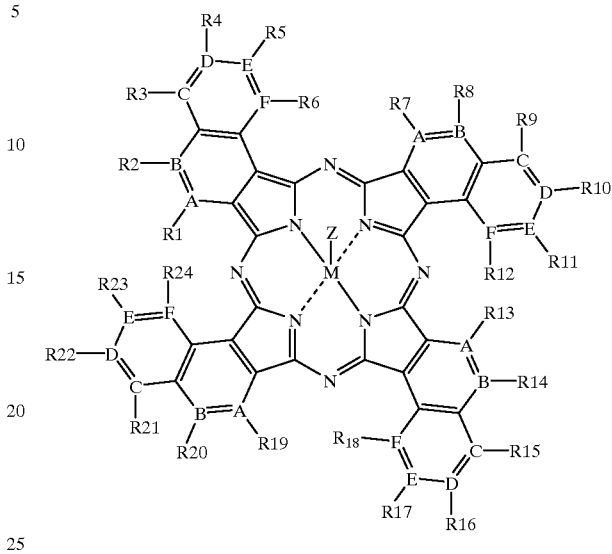

where each of R1–R24 is $CH_2CH_3$, $CH=CH_2$, $CH=CHCH_2N(CH_3)_2$, $CH=CHCH_2N^+(CH_3)_3$ $X^-$ (where X is a charge balancing ion), $C(X)_2C(X)_3$ (where X is a halogen), CHO, $COCH_3$, $CO_2H$, $CO_2R25$, CONHR25, $CH=CHCHO$, $CH_2Y$, (where Y=H, halogen, OH, OR25 or is a functional group less than or equal to 100000 daltons), $CH_2CO_2R25$, $CH_2CONHR25$, $CH=CHCH_2OH$, $CH=CHCHO_2OR25$, $CH(OH)CH_3$, $CH(OR25)CH_3$, H, halide, alkyl, cyclic alkyl (3–6 carbons), aryl, substituted aryl, alkenyl, substituted alkenyl, alkynyl, substituted alkynyl, amide, ester, NR25R25, CN, O, S, NHR25, OH, OR25, CHO, $(CH_2)_nOH$, $(CH_2)_nSH$, $(CH_2)_n$O-alkoxy, $(CH_2)_nSR25$, $(CH_2)_nOR25$ (where n=1, 2, 3, 4, and R25 is a functional group less than or equal to 100000 daltons), $(CH_2)_nCO_2R25$ (where R25 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR25, $(CH_2)_n$CON(R25)$_2$, $CO_2R25$, CONHR25, CONR25R25, SR25 (where R25 is a functional group less than or equal to 100000 daltons), $SO_3H$, $SO_3R25$, $SO_2NHR25$, $SO_2N(R25)_2$, $SO_2N(R25)_3^+X^-$ (where R25 is a functional group less than or equal to 100000 daltons and X is a charge balancing ion), protein or biomolecule or functional group less than or equal to 100000 daltons; A, B, C, D, E, F are C, N, , $O^+$, O, S, Te, P, $N^+(R25)X^-$ (where R25 is a functional group less than or equal to 100000 daltons and X is a charge balancing ion), or combinations thereof; M is $In^{113}$, $In^{115}$ or a mixture of $In^{113}$ and $In^{115}$; Z is a halide acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga

Still another family of compounds has the structure:

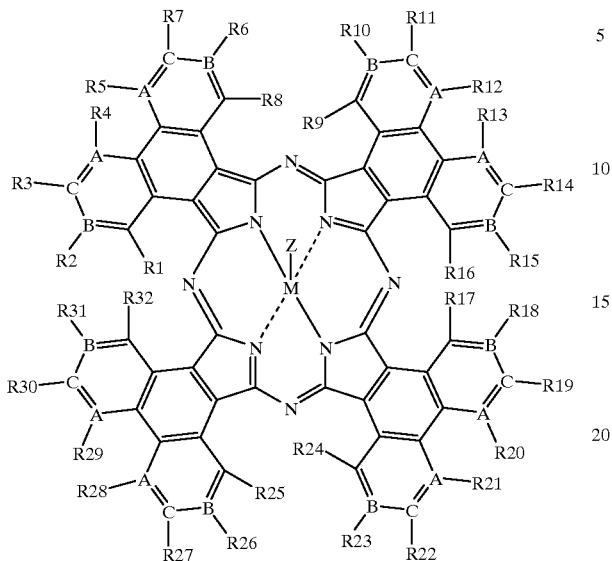

where each of R1–R32 is $CH_2CH_3$, $CH=CH_2$, $CH=CHCH_2N(CH_3)_2$, $CH=CHCH_2N^+(CH_3)_3$ $X^-$ (where X is a charge balancing ion), $C(X)_2C(X)_3$ (where X is a halogen), CHO, $COCH_3$, $CO_2H$, $CO_2R33$, CONHR33, $CH=CHCHO$, $CH_2Y$, (where Y=H, halogen, OH, OR33 or is a functional group less than or equal to 100000 daltons). $CH_2CO_2R33$, $CH_2CONHR33$, $CH=CHCH_2OH$, $CH=CHCH_2OR33$, $CH(OH)CH_3$, $CH(OR33)CH_3$, H, halide, alkyl, cyclic alkyl (3–6 carbons), aryl, substituted aryl, alkenyl, substituted alkenyl, alkynyl, substituted alkynyl, amide, ester, NR33R33, CN, O, S, NHR33, OH, OR33, CHO, $(CH_2)_nOH$, $(CH_2)_nSH$, $(CH_2)_n$O-alkoxy, $(CH_2)_nSR33$, $(CH_2)_nOR33$ (where n=1, 2, 3, 4, and R33 is a functional group less than or equal to 100000 daltons), $(CH_2)_nCO_2R33$ (where R33 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR33, $(CH_2)_n$CON(R33)$_2$, $CO_2R33$, CONHR33, CONR33R33, SR33 (where R33 is a functional group less than or equal to 100000 daltons), $SO_3H$, $SO_3R33$, $SO_2NHR33$, $SO_2N(R33)_2$, $SO_2N(R33)_3^+X^-$ (where R33 is a functional group less than or equal to 100000 daltons and X is a charge balancing ion), protein or biomolecule or functional group less than or equal to 100000 daltons; A, B, C are; C, N, $O^+$, O, S, Te, P, $N^+(R33)X^-$ (where R33 is a functional group less than or equal to 100000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga.

Still another family of compounds has the structure:

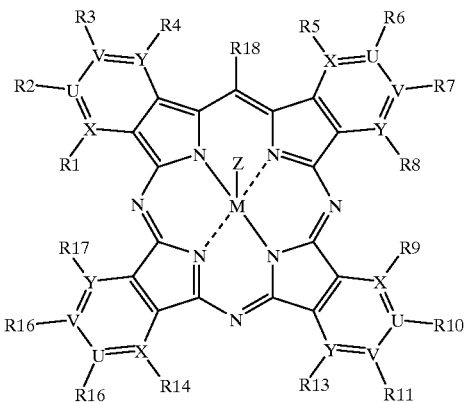

where each of R1–R18 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R19$, CONHR19, $CH=CHCHO$, $CH_2Y$, (where Y=H, halogen, OH, OR19 or is a functional group less than or equal to 100000 daltons), $CH_2CO_2R19$, $CH_2CONHR19$, $CH=CHCH_2OH$, $CH=CHCH_2OR19$, $CH(OH)CH_3$, $CH(OR9)CH_3$, H, halide, alkyl, cyclic alkyl (3–6 carbons), aryl, substituted aryl, alkenyl, substituted alkenyl, alkynyl, substituted alkynyl, amide, ester, NR19R19, CN, O, S, NHR19, OH, OR19, CHO, $(CH_2)_nOH$, $(CH_2)_nSH$, $(CH_2)_n$O-alkoxy, $(CH_2)_nSR19$, $(CH_2)_nOR19$ (where n=1, 2, 3, 4, and R19 is a functional group less than or equal to 100000 daltons), $(CH_2)_nCO_2R19$ (where R19 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR19, $(CH_2)_n$CON(R19)$_2$, $CO_2R19$, CONHR19, CONR10R19, SR19 (where $SO_2NHR19$, $SO_2N(R19)_2$, $SO_2N(R19)_3^+X^-$ (where R19 is a functional group less than or equal to 100000 daltons and X is a charge balancing ion), protein or biomolecule or functional group less than or equal to 100000 daltons. U, V, X, Y are C, N, $O^+$, O, S, Te, P, $N^+(R19)X^+$ (where R19 is a functional group less than or equal to 100000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga

Another family of compounds has the structure:

[chemical structure diagram with R1–R9, A, M]

where each of R1–R9 is $CH_2CH_3$, $CH=CH_2$, $CH=CHCH_2N(CH_3)_2$, $CH=CHCH_2N^+(CH_3)_3$ $X^-$ (where X is a charge balancing ion), $C(X)_2C(X)_3$ (where X is a halogen), CHO, $COCH_3$, $CO_2H$, $CO_2R10$, CONHR10, CH=CHCHO, $CH_2Y$, (where Y=H, halogen, OH, OR10 or is a functional group less than or equal to 100000 daltons), $CH_2CO_2R10$, $CH_2CONHR10$, $CH=CHCH_2OH$, $CH=CHCH_2OR10$, $CH(OH)CH_3$, $CH(OR10)CH_3$, H, halide, alkyl, cyclic alkyl (3–6 carbons), aryl, substituted aryl, alkenyl, substituted alkenyl, alkynyl, substituted alkynyl, amide, ester, NR10R10, CN, OH, OR10, CHO, $(CH_2)_nOH$, $(CH_2)_nSH$, $(CH_2)_nO$-alkoxy, $(CH_2)_nSR10$, $(CH_2)_nOR10$ (where n=1, 2, 3, 4, and R10 is a functional group less than or equal to 100000 daltons), $(CH_2)_nCO_2R10$ (where R10 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR10$, $(CH_2)_nCON(R10)_2$, $CO_2R10$, CONHR10, CONR10R10, SR10 (where R10 is a functional group less than or equal to 100000 daltons), $SO_3H$, $SO_3R10SO_2NHR10$, $SO_2N(R10)_2$, $SO_2N(R10)_3{}^+X^-$ (where R10 is a functional group less than or equal to 100000 daltons and X is a charge balancing ion), protein or biomolecule or functional group less than or equal to 100000 daltons; M is $In^{113}$, $In^{115}$ or a mixture of $In^{113}$, and $In^{115}$.

M can also be Ga.

Still another family of compounds has the structure:

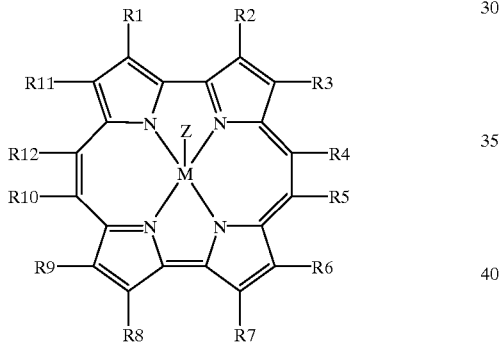

where each of R1–R12 is $CH_2CH_3$, $CH=CH_2$, $CH=CH_2$, $CH=CHCH_2N(CH_3)_2$, $CH=CHCH_2N^{30}(CH_3)_3\ X^-$ (where X is a charge balancing ion), $C(X)_2C(X)_3$ (where X is a halogen), CHO, $COCH_3$, $CO_2H$, $CO_2R13$, CONHR13, CH=CHCHO, $CH_2Y$, (where Y=H, halogen, OH, OR13 or is a functional group less than or equal to 100000 daltons), $CH_2CO_2R13$, $CH_2CONHR13$, $CH=CHCH_2OH$, $CH=CHCH_2OR13$, $CH(OH)CH_3$, $CH(OR13)CH_3$, H, halide, alkyl, cyclic alkyl (3–6 carbons), aryl, substituted aryl, alkenyl, substituted alkenyl, alkynyl, substituted alkynyl, amide, ester, NR13R13, CN, OH. OR13, CHO, $(CH_2)_nOH$, $(CH_2)_nSH$, $(CH_2)_nO$-alkoxy, $(CH_2)_nSR13$, $(CH_2)_nOR13$ (where n=1, 2, 3, 4, and R13 is a functional group less than or equal to 100000 daltons), $(CH_2)_nCO_2R13$ (where R13 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR13$, $(CH_2)_nCON(R13)_2$, $CO_2R13$, CONHR13, CONR13R13, SR13 (where R13 is a functional group less than or equal to 100000 daltons), $SO_3H$, $SO_3R13$, $SO_2NHR13$, $SO_2N(R13)_2$, $SO_2N(R13)_3{}^+X^-$ (where R13 is a functional group less than or equal to 100000 daltons and X is a charge balancing ion), protein or biomolecule or functional group less than or equal to 100000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd or Ga.

Yet another family of compounds has the structure:

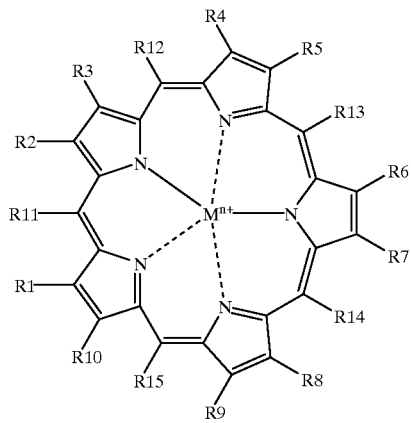

Where each of R1–R15 is $CH_2CH_3$, $CH=CH_2$, $CH=CHCH_2N(CH_3)_2$, $CH=CHCH_2N^+\ (CH_3)_3X^-$ (where X is a charge balancing ion), $C(X)_2C(X)_3$ (where X is a halogen), CHO, $COCH_3$, $CO_2H$, $CO_2R16$, CONHR16, CH=CHCHO, $CH_2Y$, (where Y=H, halogen, OH, OR16 or is a functional group less than or equal to 100000 daltons), $CH_2CO_2R16$, $CH_2CONHR16$, $CH=CHCH_2OH$, $CH=CHCH_2OR16$, $CH(OH)CH_3$, $CH(OR16)CH_3$, H, halide, alkyl, cyclic alkyl (3–6 carbons), aryl, substituted aryl, alkenyl, substituted alkenyl, alkynyl, substituted alkynyl, amide, ester, NR16R16, CN, O, S, NHR16, OH, OR16, CHO, $(CH_2)_nOH$, $(CH_2)_nSH$, $(CH_2)_nO$-alkoxy, $(CH_2)_nSR16$, $(CH_2)_nOR16$ (where n=1, 2, 3, 4, and R16 is a functional group less than or equal to 100000 daltons), $(CH_2)_nCO_2OR16$ (where R16 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHOR16$, $(CH_2)_nCON(R16)_2$, $CO_2R16$, CONHR16, CONR16R16, SR16 (where R16 is a functional group less than or equal to 100000 daltons), $SO_3H$, $SO_3R16$, $SO_2NHR16$, $SO_2N(R16)_2$, $SO_2N(R16)_3+X^-$ (where R16 is a functional group less than or equal to 100000 daltons and X is a charge balancing ion), protein or biomolecule or functional group less than or equal to 100000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be M is Ag, Ce, Co, Cr, Cu, Dy, Er, Fe, Ga, Hf, Ho, La, Lu, Mo, Mg, Nd, Pb, Pr or Rh, preferably Pd, Pt, Ga, Al, Ru, Sn or Zn.

Yet another family of compounds has the following structure:

83

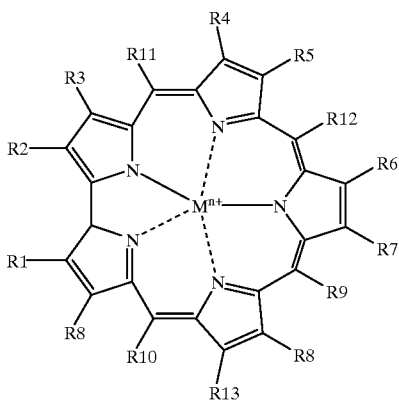

where each of R1–R14 is $CH_2CH_3$, $CH=CH_2$, $CH=CHCH_2N(CH_3)_2$, $CH=CHCH_2N^+(CH_3)_3$ $X^-$ (where X is a charge balancing ion), $C(X)_2C(X)_3$ (where X is a halogen), CHO, $COCH_3$, $CO_2H$, $CO_2R15$, CONHR15, $CH=CHCHO$, $CH_2Y$, (where Y=H, halogen, OH, OR15 or is a functional group less than or equal to 100000 daltons), $CH_2CO_2R15$, $CH_2CONHR15$, $CH=CHCH_2OH$, $CH=CHCH_2OR15$, $CH(OH)CH_3$, $CH(OR15)CH_3$, H, halide, alkyl, cyclic alkyl (3–6 carbons), aryl, substituted aryl, alkenyl, substituted alkenyl, alkynyl, substituted alkynyl, amide, ester, NR15R15, CN, O, S, NHR15, OH, OR15, CHO, $(CH_2)_nOH$, $(CH_2)_nSH$, $(CH_2)_n$O-alkoxy, $(CH_2)_nSR15$, $(CH_2)_nOR15$ (where n=1, 2, 3, 4, and R15 is a functional group less than or equal to 100000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR15, $(CH_2)_n$CON(R15)$_2$, $CO_2R15$, CONHR15, CONR15R15, SR15 (where R15 is a functional group less than or equal to 100000 daltons), $SO_3H$, $SO_3R15$, $SO_2NHR15$, $SO_2N(R15)_2$, $SO_2N(R15)_3^+X^-$ (where R15 is a functional groups less than or equal to 100000 daltons and X is a charge balancing ion), protein or biomolecule or functional group less than or equal to 100000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr or Rh, preferably Pd, Pt, Ga, Al, Ru, Sn or Zn.

Still another family of compounds has the following stucture:

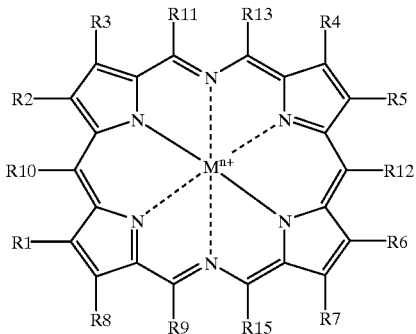

84 where each of R1–R15 is $CH_2CH_3$, $CH=CH_2$, $CH=CHCH_2N(CH_3)_2$, $CH=CHCH_2N^+(CH_3)_3$ $X^-$ (where X is a charge balancing ion), $C(X)_2C(X)_3$ (where X is a halogen), CHO, $COCH_3$, $CO_2H$, $CO_2R16$, CONHR16, $CH=CHCHO$, $CH_2Y$, (where Y=H, halogen, OH, OR16 or is a functional group less than or equal to 100000 daltons), $CH_2CO_2R16$, $CH_2CONHR16$, $CH=CHCH_2OH$, $CH=CHCH_2OR16$, $CH(OH)CH_3$, $CH(OR16)CH_3$, H, halide, alkyl, cyclic alkyl (3–6 carbons), aryl, substituted aryl, alkenyl, substituted alkenyl, alkynyl, substituted alkynyl, amide, ester, NR16R16, CN, O, S, NHR16, OH, OR16, CHO, $(CH_2)_nOH$, $(CH_2)_nSH$, $(CH_2)_n$O-alkoxy, $(CH_2)_nSR16$, $(CH_2)_nOR16$ (where n=1, 2, 3, 4, and R16 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR16, $(CH_2)_n$CON(R16)$_2$, $CO_2R16$, CONHR16, CONR16R16, SR16 (where R16 is a functional group less than or equal to 100000 daltons), $SO_3H$, $SO_3R16$, $SO_2NHR16$, $SO_2N(R16)_2$, $SO_2N(R16)_3^+X^-$ (where R16 is a functional group less than or equal to 100000 daltons and X is a charge balancing ion), protein or biomolecule or functional group less than or equal to 100000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, or Rh, preferably Pd, Pt, Ga, Al, Ru, Sn or Zn.

Yet other families of compounds have the following structure:

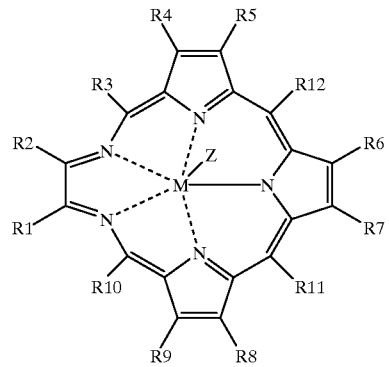

Where each of R1–R12 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R13$, CONHR13, $CH=CHCHO$, $CH_2Y$, (where Y=H, halogen, OH, OR13 or is a functional group less than or equal to 100000 daltons), $CH_2CO_2R13$, $CH_2CONHR13$ $CH=CHCH_2OH$, $CH=CHCH_2OR13$. $CH(OH)CH_3$, $CH(OR13)CH_3$, H, halide, alkyl, cyclic alkyl (3–6 carbons), aryl, substituted aryl, alkenyl, substituted alkenyl, alkynyl, substituted alkynyl, amide, ester, NR13R13, CN, O, S, NHR13, OH, OR13, CHO, $(CH_2)_nOH$, $(CH_2)_nSH$, $(CH_2)_n$O-alkoxy, $(CH_2)_nSR13$, $(CH_2)_nOR13$ (where n=1, 2, 3, 4, and R13 is a functional group less than or equal to 100000 daltons), $(CH_2)_nCO_2R13$ (where R13 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n CONHR13$, $(CH_2)_n CON(R13)_2$, $CO_2R13$, CONHR13, CONR13R13, SR13 (where R13 is a functional group less than or equal to 100000 daltons), $SO_3H$, $SO_3R13$, $SO_2NHR13$, $SO_2N(R13)_2$, $SO_2N(R13)_3{}^{+X-}$ (where R13 is a functional group less than or equal to 100000 daltons and X is a charge balancing ion), protein or biomolecule or functional group less than or equal to 100000 daltons; M is $In^{113}$, $In^{115}$ or a mnixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd, Pt, Ga or Al.

Another family of compounds has the following structure:

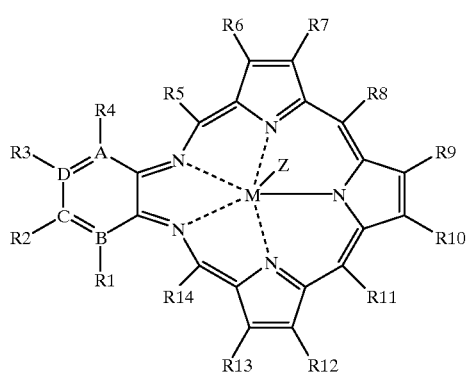

Where each of R1–R14 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R15$, CONHR15, $CH=CHCHO$, $CH_2Y$, (where Y=H, halogen, OH, OR15 or is a functional group less than or equal to 10000 daltons), $CH_2CO_2R15$, $CH_2CONHR15$, $CH=CHCH_2OH$, $CH=CHCH_2OR15$, $CH(OH)CH_3$, $CH(OR15)CH_3$, H, halide, alkyl, cyclic alkyl (3–6 carbons), aryl, substituted aryl, alkenyl, substituted alkenyl, alkynyl, substituted alkynyl, amide, ester, NR15R15, CN, O, S, NHR15, OH, OR15, CHO, $(CH_2)_n OH$, $(CH_2)_n SH$, $(CH_2)_n O$-alkoxy, $(CH_2)_n SR15$, $(CH_2)_n OR15$ (where n=1, 2, 3, 4, and R15 is a functional group less than or equal to 100000 daltons), $(CH_2)_n CO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n CONHR15$, $(CH_2)_n CON(R15)_2$, $CO_2R15$, CONHR15, CONR15R15, SR15 (where R15 is a functional group less than or equal to 100000 daltons), $SO_3H$, $SO_3OR15$, $SO_2NHR15$, $SO_2N(R15)_2$, $SO_2N(R15)_3{}^{+X-}$ (where R15 is a functional group less than or equal to 100000 daltons and X is a charge balancing ion), protein or biomolecule or functional group less than or equal to 100000 daltons; A, B, C, D are; C, N, $O^+$, O, S, Te, P, $N^+(R15)X^-$ (where R15 is a functional group less than or equal to 100000 daltons and X is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd, Pt, Ga or Al.

Yet another family of compounds has the following structure:

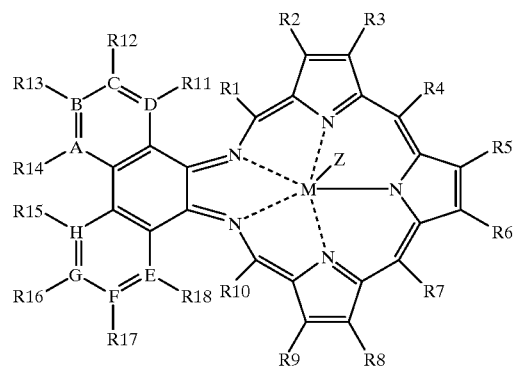

Where each of R1–R18 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R19$, CONHR19, $CH=CHCHO$, $CH_2Y$, (where Y=H, halogen, OH, OR19 or is a functional group less than or equal to 100000 daltons), $CH_2CO_2R19$, $CH_2CONHR19$, $CH=CHCH_2OH$, $CH=CHCH_2OR19$, $CH(OH)CH_3$, $CH(OR19)CH_3$, H, halide, alkyl, cyclic alkyl (3–6 carbons), aryl, substituted aryl, alkenyl, substituted alkenyl, alkynyl, substituted alkynyl, amide, ester, NR19R19, CN, O, S, NHR19, OH, OR19, CHO, $(CH_2)_n OH$, $(CH_2)_n SH$, $(CH_2)_n O$-alkoxy, $(CH_2)_n SR19$, $(CH_2)_n OR19$ (where n=1, 2, 3, 4, and R19 is a functional group less than or equal to 100000 daltons), $(CH_2)_n CO_2R19$ (where R19 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n CONHR19$, $(CH_2)_n CON(R19)_2$, $CO_2R19$, CONHR19, CONR19R19, SR19 (where R19 is a functional group less than or equal to 100000 daltons), $SO_3H$, $SO_3R19$, $SO_2NHR19$, $SO_2N(R19)_2$, $SO_2N(R19)_3{}^{+X-}$ (where R19 is a functional group less than or equal to 100000 daltons and X is a charge balancing ion), protein or biomolecule or functional group less than or equal to 100000 daltons; A, B, C, D, E , F, G, H are: C, N, $O^+$, O, S, Te, P, $N^+(R19)X^-$ (where R19 is a functional group less than or equal to 100000 daltons and X is a charge balancing ion) or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

M can also be Pd, Pt, Ga or Al.

Still another family of compounds has the following structure:

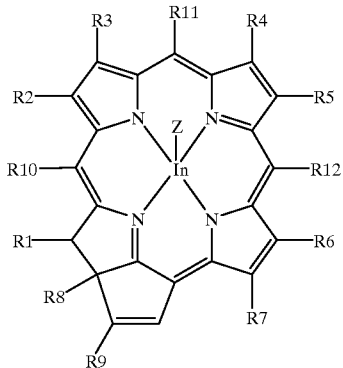

Where each of R1–R12 is $CH_2CH_3$, $CH=CH_2$, $CH=CHCH_2N(CH_3)_2X$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R13$, CONHR13, $CH=CHCHO$, $CH_2Y$, (where Y=H, halogen, OH, OR13 or is a functional group less than or equal to 100000 daltons), $CH_2CO_2R13$, $CH_2CONHR13$, $CH=CHCH_2OH$, $CH=CHCH_2OR13$, $CH(OH)CH_3$, $CH(OR13)CH_3$, H, halide, alkyl, cyclic alkyl (3–6 carbons), aryl, substituted aryl, alkenyl, substituted alkenyl, alkynyl, substituted alkynyl, amide, ester, NR13R13, CN, O, S, NHR13, OH, OR13, CHO, $(CH_2)_nOH$, $(CH_2)_nSH$, $(CH_2)_n$O-alkoxy, $(CH_2)_nSR13$, $(CH_2)_nOR13$ (where n=1, 2, 3, 4, and R13 is a functional group less than or equal to 100000 daltons), $(CH_2)_nCO_2R13$ (where R13 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR13, $(CH_2)_n$CON(R13)$_2$, $CO_2R13$, CONHR13, CONR13R13, SR13 (where R13 is a functional group less than or equal to 100000 daltons), $SO_3H$, $SO_3R13$, $SO_2NHR13$, $SO_2N(R13)_2$, $SO_2N(R13)_3^+X^-$ (where R13 is a functional group less than or equal to 100000 daltons and X is a charge balancing ion). protein or biomolecule or functional group less than or equal to 100000 daltons; Z is halide, acetate, OH, alkyl. aryl, substituted aryl, alkenyl, substituted alkenyl, alkynyl, substituted alkynyl, protein or biomolecule or functional group less than or equal to 100000 daltons.

Another family of compounds has the following structure:

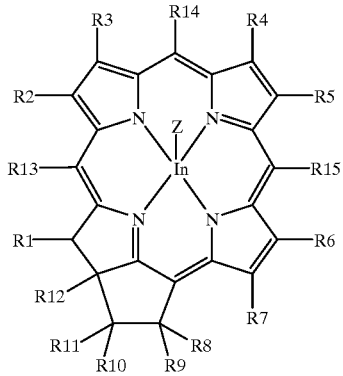

where each of R1–R15 is $CH_2CH_3$, $CH=CH_2$, $CH=CHCH_2N(CH_3)_2$, $CH=CHCH_2N^+(CH_3)_3$ $X^-$ (where X is a charge balancing ion). $C(X)_2C(X)_3$ (where X is a halogen), CHO, $COCH_3$, $CO_2H$, $CO_2R16$, CONHR16, $CH=CHCHO$, $CH_2Y$, (where Y=H, halogen, OH, OR16 or is a functional group less than or equal to 100000 daltons), $CH_2CO_2R16$, $CH_2CONHR16$, $CH=CHCH_2OH$, $CH=CHCH_2OR16$, $CH(OH)CH_3$, $CH(OR16)CH_3$, H, halide, alkyl, cyclic alkyl (3–6 carbons), aryl, substituted aryl, alkenyl, substituted alkenyl, alkynyl, substituted alkynyl, amide, ester, NR16R16, CN, O, S, NHR16, OH, OR16, CHO, $(CH_2)_nOH$, $(CH_2)_nSH$, $(CH_2)_n$O-alkoxy, $(CH_2)_nSR16$, $(CH_2)_nOR16$, (where n=1, 2, 3, 4, and R16 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR16, $(CH_2)_n$CON(R16)$_2$, $CO_2R16$, CONHR16, CONR16R16, SR16 (where R16 is a functional group less than or equal to 100000 daltons), $SO_3H$, $SO_3R16$, $SO_2NHR16$, $SO_2N(R16)_2$, $SO_2N(R16)_3^+X^-$ (where R16 is a functional group less than or equal to 100000 daltons and X is a charge balancing ion), protein or biomolecule or functional group less than or equal to 100000 daltons; Z is halide, acetate, OH, alkyl, aryl, substituted aryl, alkenyl, substituted alkenyl, alkynyl, substituted alkynyl, protein or biomolecule or functional group less than or equal to 100000 daltons.

Still another family of compounds has the following structure:

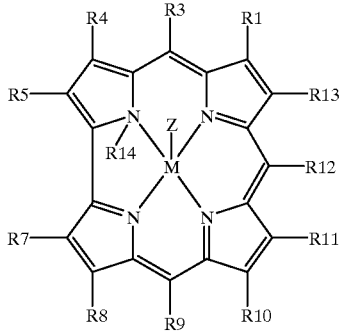

where each of R1–R14 can be $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R15$, CONHR15, $CH=CHCHO$, $CH_2Y$, (where Y=H, halogen, OH, OR15 or is a functional group less than or equal to 100000 daltons), $CH_2CO_2R15$, $CH_2CONHR15$, $CH=CHCH_2OH$, $CH=CHCH_2OR15$, $CH(OH)CH_3$, $CH(OR15)CH_3$, H, halide, alkyl, cyclic alkyl (3–6 carbons), aryl, substituted aryl, alkenyl, substituted alkenyl, alkynyl, substituted alkynyl, amide, ester, NR15R15, CN, O, S, NHR15, OH, OR15, CHO, $(CH_2)_nOH$, $(CH_2)_nSH$, $(CH_2)_n$O-alkoxy, $(CH_2)_nSR15$, $(CH_2)_nOR15$ (where n=1, 2, 3, 4, and R15 is a functional group less than or equal to 100000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_n$CONHR15, $(CH_2)_n$CON(R15)$_2$, $CO_2R15$, CONHR15, CONR15R15, SR15 (where R15 is a functional group less than or equal to 100000 daltons), $SO_3H$, $SO_3R15$, $SO_2NHR16$, $SO_2N(R15)_2$, $SO_2N(R15)_3{}^+X^-$ (where R15 is a functional group less than or equal to 100000 daltons and X is a charge balancing ion), protein or biomolecule or functional group less than or equal to 100000 daltons; M is $In^{113}$, $In^{115}$ or a mixture of $In^{113}$ and In115; Z is a halide, acetate, OH, alkyl. aryl, substituted aryl, alkenyl, substituted alkenyl, alkynyl, substituted alkynyl, protein or biomolecule or functional group less than or equal to 100000 daltons.

M can also be Ag, Ce, Co, Cr, Cu, Dy, Er, Fe, Ga, Hf, Ho, La, Lu, Mo, Mg, Nd, Pb, Pr, Rh, Sb, Sc, Sm, Sn, Tb, Th, Ti, Tl, Tm, U, V, Y, Yb or Zr, preferably Pd, Pt, Ga, Al, Ru, Sn or Zn.

Still another family of compounds has the formula:

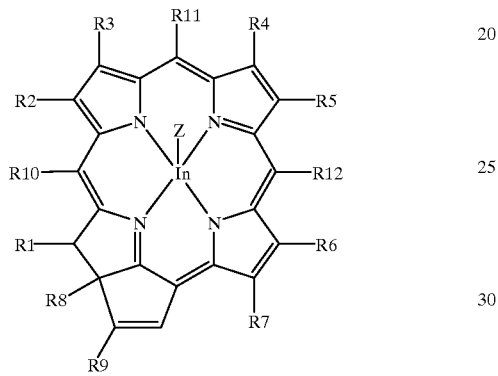

Where In is $In^{113}$, $In^{115}$, or a mixture of $In^{113}$ and $In^{115}$, each of R1–R12 is $CH_2CH_3$, $CH=CH_2$, $CH=CHCH_2N(CH_3)_2$, $CH=CHCH_2N^+(CH_3)_3X^-$ (where X is a charge balancing ion), $C(X)_2C(X)_3$ (where X is a halogen), CHO, $COCH_3$, $CO_2H$, $CO_2R13$, CONHR13, $CH=CHCHO$, $CH_2Y$. (where Y=H, halogen, OH, OR13 or is a functional group less than or equal to 100000 daltons), $CH_2CO_2R13$, $CH_2CONHR13$, $CH=CHCH_2OH$, $CH=CHCH_2OR13$, $CH(OH)CH_3$, $CH(OR13)CH_3$, H, halide, alkyl, cyclic alkyl (3–6 carbons), aryl, substituted aryl, alkenyl, substituted alkenyl, alkynyl, substituted alkynyl, amide, ester, NR13R13, CN, O, S, NHR13, OH, OR13, CHO, $(CH_2)_nOH$, $(CH_2)_nSH$, $(CH_2)_nO$-alkoxy, $(CH_2)_nSR13$, $(CH_2)_nOR13$ (where n=1, 2, 3, 4, and R13 is a functional group less than or equal to 100000 daltons), $(CH_2)_nCO_2R13$ (where R13 is H, a physiologically acceptable salt, alkyl (1–6 carbons), aryl, substituted aryl, alkenyl, substituted alkenyl, alkynyl, substituted alkynyl, and n=1, 2, 3, 4), $(CH_2)_nCONHR13$, $(CH_2)_nCON(R13)_2$, $CO_2R13$, CONHR13, CONR13R13, SR13 (where R13 is a functional groups less than or equal to 100000 daltons), $SO_3H$, $SO_3R13$, $SO_2NHR13$, $SO_2N(R13)_2$, $SO_2N(R13)_3{}^+X^-$ (where R13 is a functional groups less than or equal to 100000 daltons and X is a charge balancing ion), protein or biomolecule or functional group less than or equal to 100000 daltons; Z is halide, acetate, OH, alkyl, aryl, substituted aryl, alkenyl, substituted alkenyl, alkynyl, substituted alkynyl, protein or biomolecule or functional groups less than or equal to 100000 daltons.

Two other families of compounds have the structures of Compound I and II, below:

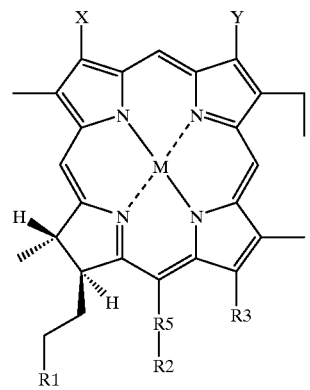

Compound I

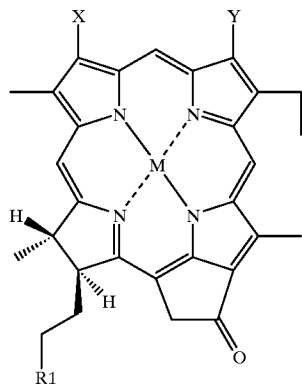

Compound II wherein M is $In^{113}$, $In^{115}$ or a mixture of $In^{113}$ and $In^{115}$ R1, R2 and R3 can be the same or different, and each is $CO_2H$, $CO_2R4$, CONR4, $CH_3Y'$, CONR4R4, $NH_2$, $N(R4)_2$, or $N(R4)_3{}^+Z^-$, where Y' is halogen, OH, OR4, or a functional group having a molecular weight equal to or less than 100,000 daltons, R4 is a functional group having a molecular weight equal to or less than 100,000 daltons, and Z is a physiologically acceptable charge balancing ion with the proviso that R4 is not a mono-or di-carboxylic acid of an amino acid, R5 is a methylene group or an ethylene group, X is H, vinyl, ethyl, acetyl or formyl, and Y is methyl or formyl.

M can also be Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh. Sb, Sc, Sm, Tb, Th, Ti, Tl, Tm, U, V, Y, Yb or Zr, and preferably is In, Pd, or Pt.

In still another aspect, the invention is a free base or a metal complex having the structure of one of Compounds III and IV, below:

Compound III

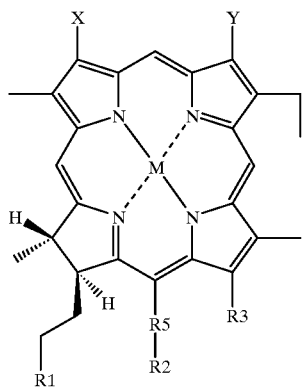

Compound IV

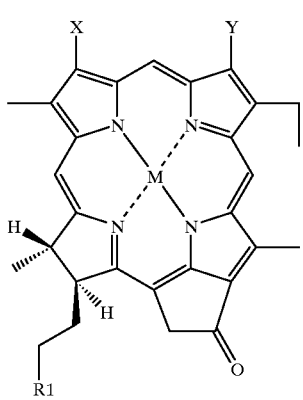

Compound V

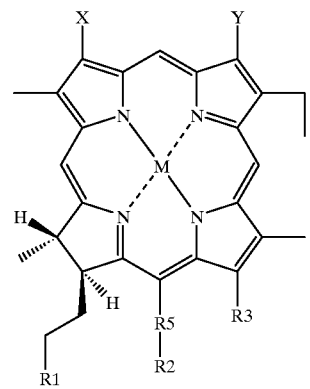

Compound VI

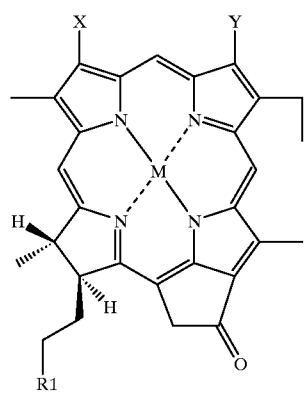

wherein M is 2H or a metal cation,

R1, R2 and R3 can be the same or different, and each is $CO_2H$, $CO_2R4$, CONR4, $CH_3Y'$, CONR4R4, $NH_2$, $N(R4)_2$, $N(R4)_3{}^+Z^-$, or CONHR6OR7 where R6 is a bivalent moiety composed of a number, n, of alkylene groups and (n minus 1) oxygens, each oxygen linking two alkylene groups through an ether linkage, CONHR6OR7 where R6 is a bivalent moiety composed of a number, n, of alkylene groups and (n minus 1) oxygens, each oxygen linking two alkylene groups through an ether linkage, and R7 is alkyl, and Z is a physiologically acceptable charge balancing ion, with the proviso that there is at least one R6 group in the structure, X is H, vinyl, ethyl, acetyl or formyl, and Y is methyl or formyl.

In the foregoing definition, and elsewhere herein, the term "alkylene" means a bivalent radical derived from an alkane with the free valences on different carbon carbon atoms. i.e., —$C_nH_{2n}$—.

Preferably, M is Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm. Sn, Tb, Th, Ti, Tl, Tm, U, V, Y, Yb, Zn or Zr, most desirably Zn, Sn, $In^{113}$, $In^{115}$, a mixture of $In^{113}$ and $In^{115}$, Pd, or Pt.

In still another aspect, the invention is a metal complex having the structure of one of Compound V and VI below:

wherein M is 2H, $In^{113}$, $In^{115}$ or a mixture of $In^{113}$ and $In^{115}$.

R1, R2 and R3 can be the same or different, and each is

X is H, vinyl, ethyl, acetyl or formyl, and

Y is methyl or formyl.

M can also be Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Th, Th, Ti, Tl, Tm, U, V, Y, Yb or Zr, most desirably Pd, Pt, $In^{113}$, $In^{115}$ or a mixture of $In^{113}$ and $In^{115}$.

In the foregoing discussion of the invention and in the following claims, the term functional group having a molecular weight equal to or less than 100,000 daltons has been used. This term refers to such groups as monoclonal antibodies, proteins, saccharides, oligomeric nucleosides, peptides and the like. The terms alkyl, alkenyl, alkynyl, substituted alkenyl, substituted alkynyl and aryl, when used herein and in the appended claims to refer to substituents, preferably mean groups having 1 to 10, 2 to 10, 2 to 10, 2 to 10, 2 to 10 and 6 to 10 carbons, respectively.

It will be apparent that various changes and modifications can be made from the specific disclosure of the invention set forth herein without departing from the spirit and scope thereof as defined in the following claims.

What is claimed is:

1. A phototherapeutic compound composed of an atom of $In^{113}$ or of $In^{115}$ complexed with the inner nitrogens of a pyrrolic core or a phototherapeutic composition consisting essentially of a mixture of $In^{113}$ and of $In^{115}$ atoms complexed with the inner nitrogens of a pyrrolic core where, in both instances, the core is composed of at least two pyrroles whose pyrrole linking atoms may be carbon or nitrogen or combinations thereof, with the proviso that indiummonoacetylethylene glycol mono-10b-pheophorbate, indium-di-2,4-(1-ethanalcoholoxyethl)-deuteroporohyrinindium; indium deuteroporphyrin; indium hematoporphyrin; 2-[1-(diethylenetriamine-tetraacetic acidacetyloxyethane)oxyethyl]-4-[1-(2-hydroxyethyl) oxyethyl]In deuteroporphyrin; 2,4-Bis[1-(diethylenetriamine-tetraacetic acidacetyloxyethane) oxyethyl]In deuteroporphyrin; 2-[1-(In-diethylenetriamine-tetracaetic acidacetyloxyethane)oxyethyl]-4-[1-(2-hydroxyethyl)oxyethyl]In-deuteroporphyrin; 2,4-Bis[(1-(In-diethylenetriamine-tetracaetic-acetyloxyethane)oxyethyl] In-deuteroporphyrin; In-Hematoporphinyl diglycine; In-Hematoporphinyl diglutamic acid; In-Diacetylhematoporphinyl diglycine; In-Diacetylhematoporphinyl diglutamic acid; fully unsaturated porphyrins having the structure:

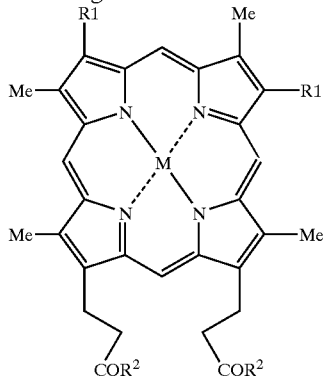

where R1 is CH(OR)Me, R is alkyl, R2 is a residue derived by removing H from an amino acid or from diethylenetriaminepentaacetic acid, and M is In; and porphyrin derivatives having the structure

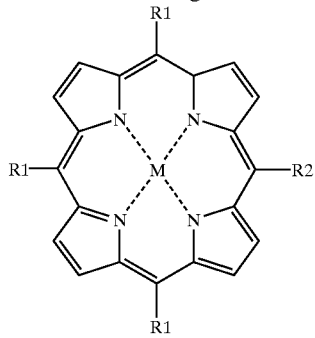

where R1 is pyridyl, R2 is a substituted phenyl group and M is indium, are excluded.

2. A phototherapeutic compound or composition as claimed in claim 1 wherein the core is a tetrapyrolic core.

3. A phototherapeutic compound or composition as claimed in claim 2 wherein the core is a dihydro or tetrahydro tetrapyrrolic core.

4. A phototherapeutic compound or composition as claimed in claim 3 which has a tetrapyrrolic core whose linking atoms are carbon.

5. A phototherapeutic compound or composition as claimed in claim 4 having the structure of one of Compound V and Compound VI, below:

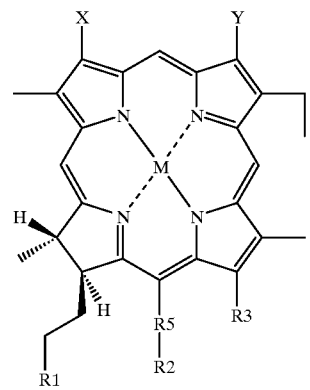

Compound V

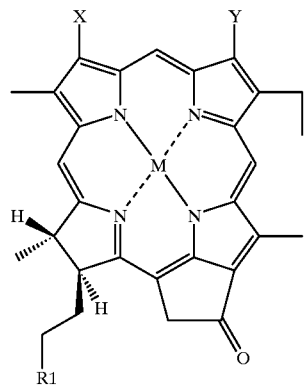

Compound VI wherein M is $[2H,]In^{113}$, $In^{115}$ or a mixture of $In^{113}$ and $In^{115}$ and, associated with the $In^{113}$, $In^{115}$ or mixture of $In^{113}$ and $In^{115}$, a physiologically acceptable charge balancing ion, R1 and R3 can be the same or different, and each is $CO_2CH_3$, $CO_2H$, $CO_2R4$, or an amide, where R4 is an alkyl or a phenyl group, R2 is $CO_2CH_3$, $CO_2H$, $CO_2R4$, an amide, $CH_2CO_2CH_3$, $CH_2CO_2H$, or $CH_2CO_2R4$, where R4 is an alkyl or a phenyl group, R5 is methylene or ethylene, X is H, vinyl, ethyl, acetyl or formyl, and Y is methyl or formyl.

6. A phototherapeutic compound or composition as claimed in claim 4 which has the structure:

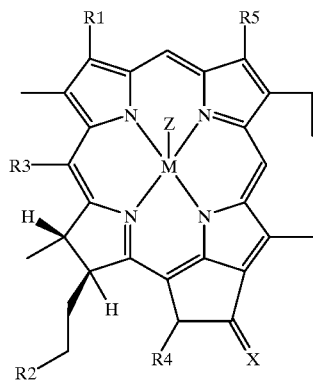

where each of R1–R5 is $CH_2CH_3$, $CH=CH_2$, $CH=CHCH_2N(CH_3)_2$, $CH=CHCH_2N^+(CH_3)_3X1^-$, C(Y1)$_2$C(Y1)$_3$, CHO, COCH$_3$, CO$_2$H, CO$_2$R6, CONHR7, CH=CHCHO, CH$_2$Y, CH=CHCH$_2$OH, CH=CHCH$_2$OR6, CH(OH)CH$_3$, CH(OR6)CH$_3$, H, halide, alkyl, cyclic alkyl (3–6 carbons), aryl substituted aryl alkenyl substituted alkenyl alkynyl, substituted alkynyl, amide, ester, NR6R6, CN, OH, OR6, (CH$_2$)$_n$OH, (CH$_2$)$_n$SH, (CH$_2$)$_n$O-alkoxy, (CH$_2$)$_n$SR6, (CH$_2$)$_n$OR6, (CH$_2$)$_n$CO$_2$R6, (CH$_2$)$_n$CONHR6, (CH$_2$)$_n$CON(R6)$_2$, CO$_2$R6, CONHR6, CONR6R6, SR6, SO$_3$H, SO$_3$R6, SO$_2$NHR6, SO$_2$N(R6)$_2$, M is In$^{113}$, In$^{115}$ or a mixture of In$^{113}$ and In$^{115}$;

n is 1, 2, 3 or 4;

Z is a halide, acetate, OH, alkyl, aryl substituted aryl alkenyl, substituted alkenyl, alkynyl substituted alkynyl, protein or biomolecule or functional group less than or equal to 100000 daltons;

Y1 is halogen;

Y is H, halogen, OH, OR6 or is a functional group less than or equal to 100000 daltons;

Y1 is halogen;

R6 is a functional group less than or equal to 100000 daltons;

R7 is H, a physiologically acceptable salt, alkyl (1–6 carbons), aryl, substituted aryl, alkenyl substituted alkenyl alkynyl or substituted alkynyl;

X1 is a charge balancing ion; and

X is O, 2H, (H, OH), S, (H, OR6) or a ketone protecting group.

7. A phototherapeutic compound or composition as claimed in claim 6 wherein:

R1 is CH=CH$_2$, CHO, Et, COCH$_3$

R2 is CO$_2$CH$_3$, CO$_2$H, or an amide

R3 and R4 are H

R5 is CH$_3$

X is O

M is In$^{113}$, In$^{115}$ or a mixture of In$^{113}$ and In$^{115}$

Z is a halide, acetate or OH.

8. A phototherapeutic compound or composition as claimed in claim 2 which has the structure:

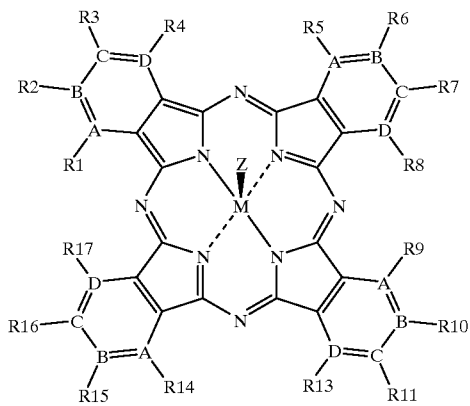

where each of R1–R17 is H, halide, alkyl cyclic alkyl (3–6 carbons), aryl, substituted aryl alkenyl, substituted alkenyl, alkynyl, substituted alkynyl, amide, ester, C(X)$_2$C(X)$_3$ (where X is a halogen), NR18R18, CN, OH, OR18, CHO, COCH$_3$, (CH$_2$)$_n$OH, (CH$_2$)$_n$SH, CH(OR18)CH$_3$, (CH$_2$)$_n$O-alkoxy, (CH$_2$)$_n$SR18, (CH$_2$)$_n$OR18(where n=1, 2, 3, 4, and R18 is a functional group less than or equal to 100000 daltons), (CH$_2$)$_n$CO$_2$R19 (where R19 is H, a physiologically acceptable salt, alkyl (1–6 carbons), aryl, substituted aryl alkenyl, substituted alkenyl, alkynyl or substituted alkynyl, and n=1, 2, 3, 4), (CH$_2$)$_n$CONHR18, (CH$_2$)$_n$CON(R18)$_2$, CO$_2$R18, CONHR18, CONR18R18, SR18 (where n=1, 2, 3, 4), SO$_3$X1, SO$_3$R18, SO$_2$NHR18, SO$_2$N(R18)$_2$; A, B, C and D are C, N, O$^+$, O, S, Te, P N$^+$(R18)X1$^-$ (where X1 is a charge balancing ion), or combinations thereof; M is In$^{113}$, In$^{115}$ or a mixture of In$^{113}$ and In$^{115}$, Z is a halide, acetate, OH, alkyl, aryl, substituted aryl, alkenyl, substituted alkenyl, alkynyl, substituted alkynyl, a protein or biomolecule or functional group less than or equal to 100000 daltons.

9. A phototherapeutic compound or composition as claimed in claim 2 which has the structure:

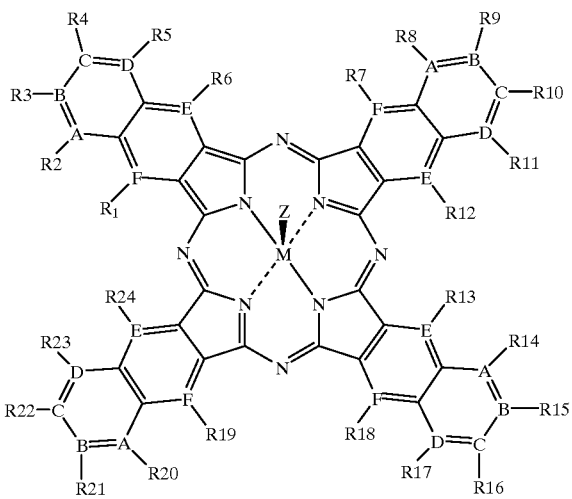

were each of R1–R24 is H, halide, alkyl, cyclic alkyl (3–6 carbons), aryl, substituted aryl, alkenyl, substituted alkenyl, alkynyl, substituted alkynyl, amide, ester, C(X)$_2$C(X)$_3$ (where X is a halogen), NR25R25, CN, OH, OR25, CHO, COCH$_3$, (CH$_2$)$_n$OH, (CH$_2$)$_n$SH, CH(OR25)CH$_3$, (CH$_2$)$_n$O-alkoxy, (CH$_2$)$_n$SR25, (CH$_2$)$_n$OR25 (where n=1, 2, 3, 4, and R25 is a functional group less than or equal to 100000 daltons), (CH$_2$)$_n$CO$_2$R26 (where R26 is H, a physiologically acceptable salt, alkyl (1–6 carbons), aryl, substituted all, alkenyl, substituted alkenyl, alkynyl or substituted alkynyl, and n=1, 2, 3, 4), (CH$_2$)$_n$CONHR25, (CH$_2$)$_n$CON(R25)$_2$, CO$_2$R25, CONHR25, CONR25R25, SR25, SO$_3$H, SO$_3$R25, SO$_2$NHR25, SO$_2$N(R25)$_2$; M is In$^{113}$, In$^{115}$ or a mixture of In$^{113}$ and In$^{115}$; A, B, C, D, E, F are C, N, O$^+$, S, Te, P, N$^+$(R25)X1$^{31}$ (where X1 is a charge balancing ion), or combinations thereof; Z is a halide, acetate, OH, alkyl, aryl, substituted aryl, alkenyl, substituted alkenyl, alkynyl, substituted alkynyl, or a protein or biomolecule or functional group less than or equal to 100000 daltons.

10. A phototherapeutic compound or composition as claimed in claim 4 which has the structure:

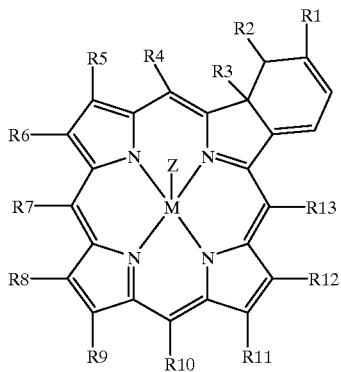

where each R1–R13 is H, halide, alkyl, vinyl, cyclic alknyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3X1^-$ (where X1 is a charge balancing ion), $C(X)_2C(X)_3$ (where X is a halogen), NR14R14, CN, OH, OR14, CHO, $COCH_3$, $(CH_2)_nOH$, $(CH_2)_nSH$, $(CH_2)_nO$-alkoxy, $CH(OH)CH_3$, $CH(OR14)CH_3$ $(CH_2)_nSR14$, $(CH_2)_nOR14$ (where n=1, 2, 3, 4, and R14 is a functional group less than or equal to 100000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR14$, $(CH_2)_nCON(R14)_2$, $CO_2R14$, CONHR14, CONR14R14, SR14, $SO_3X1$, $SO_3R14$, $SO_2R14$, $SO_2NHR14$, $SO_2N(R14)_2$; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, a protein or biomolecule or functional group less than or equal to 100000 daltons.

11. A phototherapeutic compound or composition as claimed in claim 4 which has the structure:

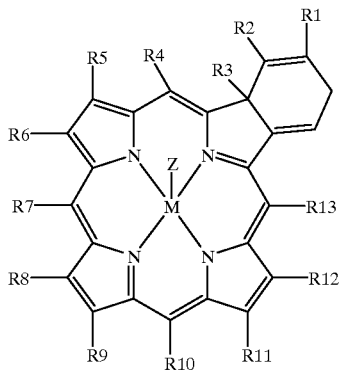

where each of R1–R13 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3X^-$ (where X is a charge balancing ion), $C(Y)_2C(Y)_3$ (where Y is a halogen), NR14R14, CN, OH, OR14, CHO, $(CH_2)_nOH$, $(CH_2)_nSH$, $(CH_2)_nO$-alkoxy, $CH(OH)CH_3$, $CH(OR14)CH_3(CH_2)_nSR14$, $(CH_2)_nOR14$ (where n=1, 2, 3, 4, and R14 is a functional group less than or equal to 100000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR14$, $(CH_2)_nCON(R14)_2$, $CO_2R14$, CONHR14, CONR14R14, SR14, $SO_3H$, $SO_3R14$, $SO_2NHR14$, $SO_2N(R14)_2$; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, or substituted alkynyl, protein or biomolecule or functional group less than or equal to 100000 daltons.

12. A phototherapeutic compound or composition as claimed in claim 4 which has the structure:

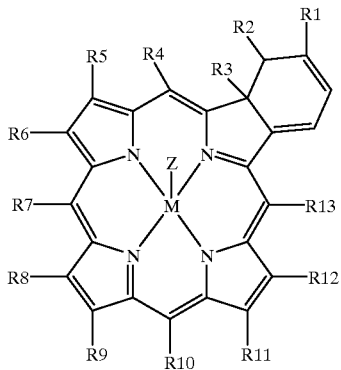

where each of R1 and R2 is $CO_2R14$ (where R14 is alkyl or aryl), $CO_2H$ (or a salt thereof), $SO_2Ph$, CN or combinations thereof;

Each of R3, R6, R8, R12 is Me

R5 is $CH=CH_2$, or $CH(OR14)CH_3$ (where R14 is alkyl or aryl)

Each of R4, R7, R13, R10 is H

R9 and R11 are $CH_2CH_2CO_2R15$ (where R15 is alkyl or H or a salt of the carboxylic acid)

M is $In^{113}$, $In^{115}$ or a mixture of $In^{113}$ and $In^{115}$.

Z is a halide, acetate, or OH.

13. A phototherapeutic compound or composition as claimed in claim 4 which has the structure:

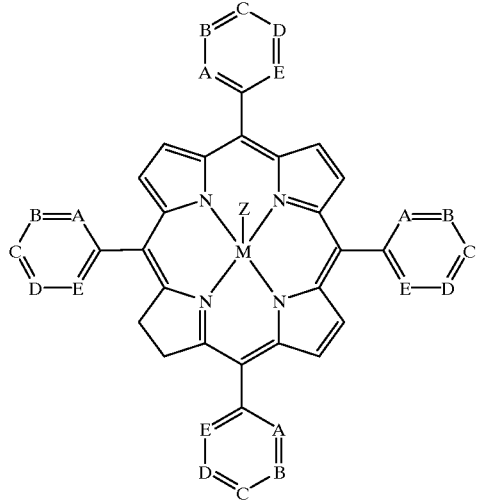

where each of A, B, C, D and E is C, N, $N^+R$ (where R is alkyl charged or uncharged) or combinations thereof;

M is In$^{113}$, In$^{115}$ or a mixture of In$^{113}$ and In$^{115}$ and
Z is a halide, acetate, OH.

14. A phototherapeutic compound or composition as claimed in claim 4 which has the structure:

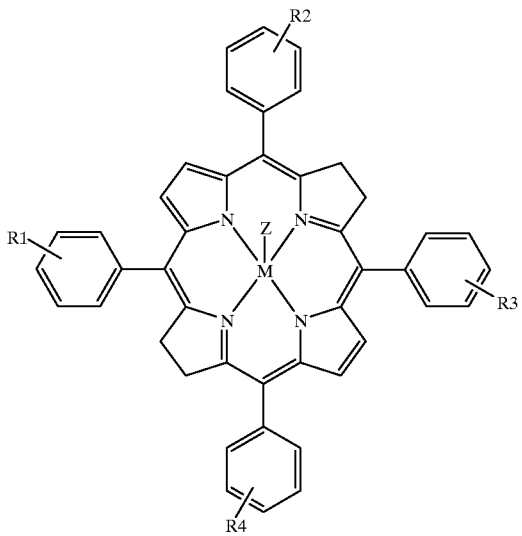

where each of R1 through R4 is SO$_3$H (or a salt thereof), SO$_2$NHR5, CO$_2$H (or a salt thereof), CONHR5, OH, OR5 (wherein R5 is an alcohol or ether containing group), amide, N(CH$_3$)$_2$, N(Et)$_2$, M is In$^{113}$, In$^{115}$ or a mixture of In$^{113}$ and In$^{115}$ Z is a halide, acetate, OH.

15. A phototherapeutic compound or composition as claimed in claim 4 which has the structure:

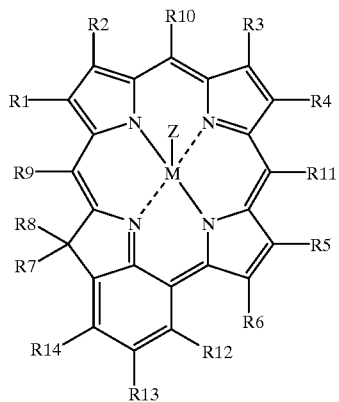

where each of R1–R14 is H, halide, methyl, ethyl, alkyl, cyclic alkyl (3–6 carbons), aryl, substituted aryl, alkenyl, substituted alkenyl, alkynyl, substituted alkynyl, amide, ester, C(X)$_2$C(X)$_3$ (where X is a halogen), NR15R15, CN, OH, OR15, CHO, COCH$_3$, CH(OR15)CH$_3$, (CH$_2$)$_n$OH, (CH$_2$)$_n$SH, (CH$_2$)$_n$O-alkoxy, (CH$_2$)$_n$SR15, (CH$_2$)$_n$OR15 (where n=1, 2, 3, 4, and R15 is a functional group less than or equal to 100000 daltons), (CH$_2$)$_n$CO$_2$R16 (where R16 is H, a physiologically acceptable salt, alkyl (1–6 carbons), aryl, substituted aryl, alkenyl, substituted alkenyl, alkynyl and n=1, 2, 3, 4), (CH$_2$)$_n$CONHR15, (CH$_2$)$_n$CON(R15)$_2$, CO$_2$R15, CONHR15, CONR15R15, SR15 (where n=1, 2, 3, 4), SO$_3$H, SO$_3$R16, SO$_2$NHR15, SO$_2$N(R15)$_2$; M is In$^{113}$, In$^{115}$ or a mixture of In$^{113}$ and In$^{115}$ Z is a halide, acetate, OH, alkyl, aryl, substituted aryl, alkenyl, substituted alkenyl, alkynyl, substituted alkynyl, or a functional group less than or equal to 100000 daltons, a protein or a biomolecule.

16. A phototherapeutic compound or composition as claimed in claim 4 which has the structure:

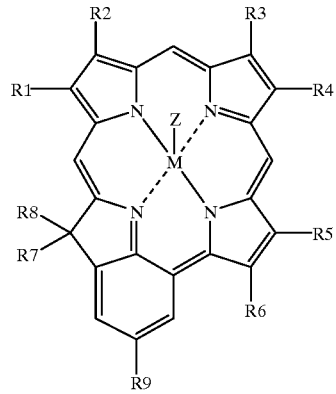

where each of R1–R8 is ethyl or methyl

R9 is CH$_3$, SO$_2$NH(CH$_2$CH$_2$O)$_n$CH$_3$ (n=1 to 1000), SO$_2$N((CH$_2$CH$_2$O)$_n$CH$_3$)$_2$ (n–1 to 1000); SO$_2$NH(CH$_2$)$_n$OH (n=1 to 1000), CH$_3$, SO$_2$N((CH$_2$CH$_2$)$_n$OH)$_2$ (n=1 to 1000); SO$_2$NC((N(CH$_3$)$_2$)$_2$; SO$_2$NH(CH$_2$)$_n$N(CH$_3$)$_2$ (n=1 to 1000); SO$_2$NH(CH$_2$)$_n$SH (n=1 to 1000); SO$_2$NHC(CH$_2$CH$_2$OH)$_3$; SO$_2$NHCH$_2$CO$_2$H (or salts thereof); SO$_2$NH(CH$_2$)$_n$CH(NH$_2$)CO$_2$H (or salts thereof) (n=1 to 5); SO$_2$NHCH$_2$CO$_2$R10 (R10 is alkyl, aryl); SO$_2$NH(CH$_2$)$_n$CH(NH$_2$)CO$_2$R10 (R10 is alkyl, aryl) (n=1 to 5)

M is In$^{113}$, In$^{115}$ or a mixture of In$^{113}$ and In$^{115}$ Z is a halide, acetate, OH.

17. A phototherapeutic compound or composition as claimed in claim 4 which has the structure:

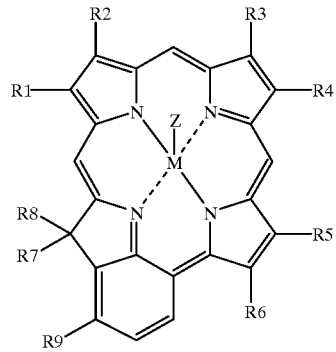

where each of R1–R8 is ethyl or methyl;

R9 is CH$_2$CONH(CH$_2$CH$_2$O)$_n$CH$_3$ (n=1 to 1000), CH$_2$CON((CH$_2$CH$_2$O)$_n$CH$_3$)$_2$ (n=1 to 1000); CH$_2$CONH(CH$_2$)$_n$OH (n=1 to 1000), CH$_2$CON((CH$_2$CH$_2$)$_n$OH)$_2$ (n=1 to 1000; CH$_2$CONC((N(CH$_3$)$_2$)$_2$; CH$_2$CONH(CH$_2$)$_n$N(CH$_3$)$_2$ (n=1 to 1000); CH$_2$CONH(CH$_2$)$_n$SH (n=1 to 1000); CH$_2$CONHC(CH$_2$CH$_2$OH)$_3$; CH$_2$CONHCH$_2$CO$_2$H (or salts thereof); CH$_2$CONH(CH$_2$)$_n$CH(NH$_2$)CO$_2$H (n=1 to 5); CH$_2$CONHCH$_2$CO$_2$R10 (R10 is alkyl, aryl); CH$_2$CONH(CH$_2$)$_n$CH(NH$_2$)CO$_2$R10 (R10 is alkyl, aryl) (n=1to 5)

M is $In^{113}$, $In^{115}$ or a mixture of $In^{113}$ and $In^{115}$;

Z is a halide, acetate, OH.

18. A phototherapeutic compound or composition as claimed in claim 4 which has the structure:

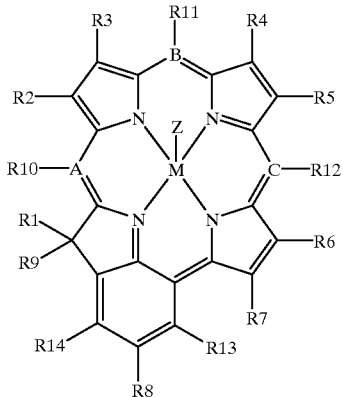

where each of R1–R14 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3X^-$ (where X is a charge balancing ion), $C(X1)_2C(X1)_3$ (where X1 is a halogen), NR15R15, CN, OH, OR15, CHO, $(CH_2)_nOH$, $(CH_2)_nSH$, $(CH_2)_nO$-alkoxy, $CH(OH)CH_3$, $CH(OR15)CH_3$ $(CH_2)_nSR15$, $(CH_2)_nOR15$ (where n=1, 2, 3, 4, and R15 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl and n=1, 2, 3, 4), $(CH_2)_nCONHR15$, $(CH_2)_nCON(R15)_2$, $CO_2R15$, CONHR15, CONR15R15, SR15, $SO_3H$, $SO_3R15$, $SO_2NHR15$, $SO_2N(R15)_2$; A, B, C are C, N, $O^+$, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

19. A phototherapeutic compound or composition as claimed in claim 4 which has the structure:

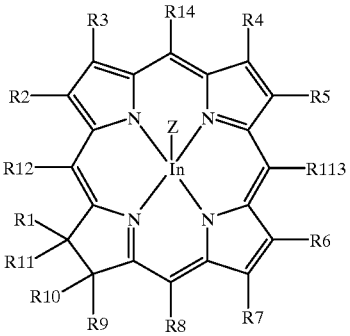

where each of R1 through R14 is H, halide, alkyl, cyclic alkyl (1–6 carbons), aryl, substituted aryl, alkenyl, substituted alkenyl, alkynyl, substituted alkynyl, amide, ester, $C(X1)_2C(X1)_3$ (where X1 is a halogen), NR15R15, CN, OH, OR15, CHO, $COCH_3$, $(CH_2)_nOH$, $(CH_2)_nSH$, $(CH_2)_nO$-alkoxy, $(CH_2)_nSR15$, $(CH_2)_nOR15$ (where n=1, 2, 3, 4, and R15 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR15$, $(CH_2)_nCON(R15)_2$, $CO_2R15$, CONHR15, $CON(R15)_2$, SR15 $SO_3H$, $SO_3R15$, $SO_2NHR15$, $SO_2N(R15)_2$, M is $In^{113}$; $In^{115}$ or a mixture of $In^{113}$ and $In^{115}$; Z is a halide, acetate, OH, alkyl, aryl, substituted aryl, alkenyl, substituted alkenyl, alkynyl or substituted alkynyl, or a functional group less than or equal to 100000 daltons, protein or biomolecule.

20. A phototherapeutic compound or composition as claimed in claim 4 which has the structure:

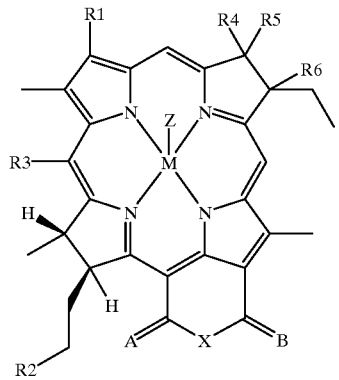

wherein;

R1 is $CH=CH_2$, Et, CHO, or $COCH_3$

R4 is Me

R3 is H each of R5 and R6 is OH

R2 is $CO_2CH_3$, $CO_2H$, $CO_2R7$ (R7 is alkyl or phenyl), or an amide

Each of A and B is O or NR8 (R8 is alkyl);

X is O or NR9 R9 is alkyl, an amino acid, an alcohol containing group, or an ether containing group)

M is $In^{113}$, $In^{115}$ or a mixture of $In^{113}$ and $In^{115}$

Z is a halide, acetate, or OH.

21. A phototherapeutic compound or composition as claimed in claim 4 which has the structure:

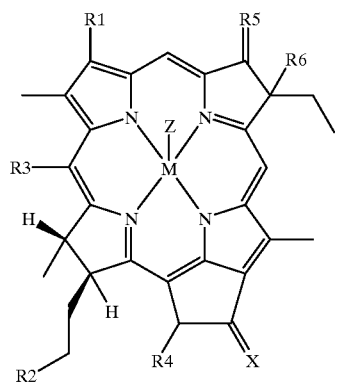

where each of R1–R6 is $CH_2CH_3$, $CH=CH_2$, $CH=CHCH_2N(CH_3)_2$, $CH=CHCH_2N^+(CH_3)_3X1^-$, $C(X2)_2C(X2)_3$, CHO, $COCH_3$, $CO_2H$, $CO_2R7$, CONHR7, CH=CHCHO, $CH_2Y$, $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, $(CH_2)_nOH$, $(CH_2)_nSH$, $(CH_2)_nO$-alkoxy, $(CH_2)_nSR7$, $(CH_2)_nOR7$, $(CH_2)_nCO_2R7'$, $(CH_2)_nCONHR7$, $CO_2R7$, CONHR7, CONR7R7, SR7, $SO_3H$, $SO_3R7$, $SO_2NHR7$, $SO_2N(R7)_2$, a protein or biomolecule or a functional group less than or equal to 100000 daltons; X is O, $H_2$, (H, OH), S, or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons wherein X1 is a charge balancing ion R7 is a functional group less than or equal to 100000 daltons Y=H, halogen, OH, OR7 or is a functional group less than or equal to 100000 daltons X2 is a halogen n=1, 2, 3, 4, and R7' is H, a physiologically acceptable salt, alkyl (1–6 carbons), aryl, substituted aryl, alkenyl, substituted alkenyl, alkynyl or substituted alkynyl.

22. A phototherapeutic compound or composition as claimed in claim 4 which has the structure:

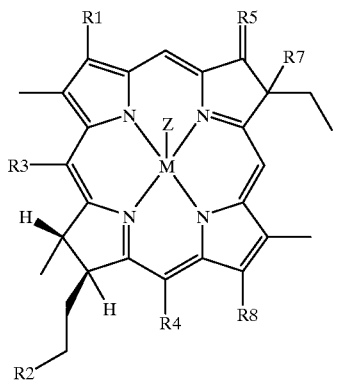

where each of R1–R8 is $CH_2CH_3$, $CH=CH_2$, $CH=CHCH_2N(CH_3)_2$, $CH=CHCH_2N^+(CH_3)_3X^-$, $C(X1)_2C(X1)_3$, CHO, $COCH_3$, $CO_2H$, $CO_2R9$, CONHR9, CH=CHCHO, $CH_2Y$, $CH_2CO_2R9$, $CH_2CONHR9$, $CH=CHCH_2OH$, $CH=CHCH_2OR9$, $CH(OH)CH_3$, $CH(OR9)CH_3$, H, halide, alkyl, cyclic alkyl (3–6 carbons), aryl, substituted aryl, alkenyl, substituted alkenyl, alkynyl, substituted alkynyl, amide, ester, NR9R9, CN, O, S, NHR9, OH, OR9, CHO, $(CH_2)_nOH$, $(CH_2)_nSH$, $(CH_2)_nO$-alkoxy, $(CH_2)_nSR9$, $(CH_2)_nOR9$, $(CH_2)_nCO_2R9'$, $(CH_2)_nCONHR9$, $(CH_2)_nCON(R9)_2$, $CO_2R9$, CONHR9, CONR9R9, SR9, $SO_3H$, $SO_3R9$, $SO_2NHR9$, $SO_2N(R9)_2$, protein or biomolecule or functional group less than or equal to 100000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, a protein or biomolecule or functional group less than or equal to 100000 daltons, wherein X is a charge balancing ion R9 is a functional group less than or equal to 100000 daltons Y=H, halogen, OH, OR9 or is a functional group less than or equal to 100000 daltons X1 is a halogen n=1, 2, 3, 4, and R9' is H, a physiologically acceptable salt, alkyl (1–6 carbons), aryl, substituted aryl, alkenyl, substituted alkenyl, alkynyl or substituted alkynyl.

23. A phototherapeutic compound or composition as claimed in claim 4 which has the structure:

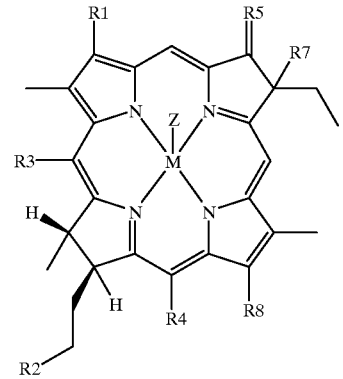

wherein;

R1 is $CH=CH_2$, Et, CHO, or $COCH_3$

R5 is O or NR9 (where R9 is alkyl)

R7 is Me

R3 is H

R4 and R8 are H, $CO_2CH_3$, $CO_2H$ (or a salt thereof), $CO_2R10$ (R10 is an alkyl or a phenyl group), an amide, $CH_2CO_2CH_3$, $CH_2CO_2H$ (or a salt thereof), R2 is $CO_2CH_3$, $CO_2H$, $CO_2R10$ (R10 is an alkyl or a phenyl group), or an amide; M is $In^{113}$, $In^{115}$ or a mixture of $In^{113}$ and $In^{115}$ Z is a halide, acetate, or OH.

24. A phototherapeutic compound or composition as claimed in claim 4 which has the structure:

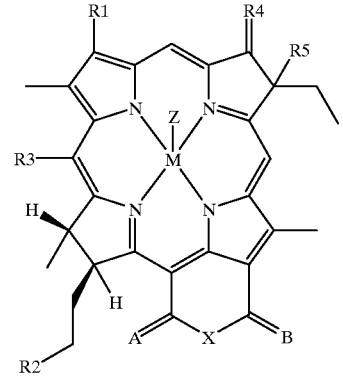

where each of R1–R5 is $CH_2CH_3$, $CH=CH_2$, $CH=CHCH_2N(CH_3)_2$, $CH=CHCH_2N^+(CH_3)_3$ $X1^-$, $C(X2)_2C(X2)_3$, CHO, $COCH_3$, $CO_2H$, $CO_2R6$, CONHR6, CH=CHCHO, $CH_2Y$, $CH_2CO_2R6$, $CH_2CONHR6$, $CH=CHCH_2OH$, $CH=CHCH_2OR6$, $CH(OH)CH_3$, $CH(OR6)CH_3$, H, halide, alkyl, cyclic alkyl (3–6 carbons), aryl, substituted aryl, alkenyl, substituted alkenyl, alkynyl, substituted alkynyl, amide, ester, NR6R6, CN, O, S, NHR6, OH, OR6, CHO, $(CH_2)_nOH$, $(CH_2)_nSH$, $(CH_2)_n$O-alkoxy, $(CH_2)_nSR6$, $(CH_2)_nOR6$, $(CH_2)_nCO_2R7$, $(CH_2)_nCONHR6$, $CO_2R6$, $CONHR6$, $CONR6R6$, $SR6$, $SO_3H$, $SO_3R6$, $SO_2NHR6$, $SO_2N(R6)_2$, a protein or biomolecule or a functional group less than or equal to 100000 daltons; X is O, NR8; A and B are O, NH, NR6 or combinations thereof; Z is a halide, acetate, OH, alkyl, aryl, substituted aryl, alkenyl, substituted alkenyl, alkynyl, substituted alkynyl, protein or biomolecule or functional group less than or equal to 100000 daltons wherein X1 is a charge balancing ion R6 is a functional group less than or equal to 100000 daltons Y=H, halogen, OH, OR6 or is a functional group less than or equal to 100000 daltons X2 is a halogen n=1, 2, 3, 4, R7 is H, a physiologically acceptable salt, alkyl (1–6 carbons), aryl, substituted aryl, alkenyl, substituted alkenyl, alkynyl or substituted alkynyl, and, R8 is H, alkyl (1–10 carbons), aryl, substituted aryl, alkenyl, substituted alkenyl, alkynyl, substituted alkynyl, an amino acid, an amino acid ester or a functional group equal to or less than 100000 daltons.

25. A phototherapeutic compound or composition as claimed in claim 4 which has the structure:

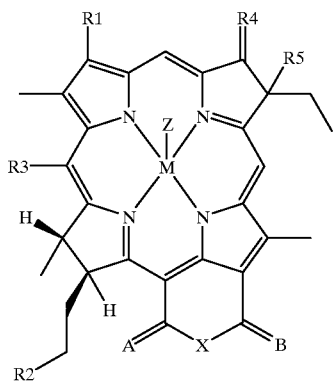

wherein:

R1 is $CH=CH_2$, Et, CHO, or $COCH_3$

R4 is O or NR6 (where R6 is alkyl)

R5 is Me

R3 is H

R2 is $CO_2CH_3$, $CO_2H$, $CO_2R7$ (R7 is an alkyl or a phenyl group), or an amide X is O, NR8 (R8 is alkyl, an amino acid, an alcohol containing group, or an ether containing group)

M is $In^{113}$, $In^{115}$ or a mixture of $In^{113}$ and $In^{115}$

Z is a halide, acetate, OH, and

A and B are O or NR9 where R9 is alkyl.

26. A phototherapeutic compound or composition as claimed in claim 4 which has the structure:

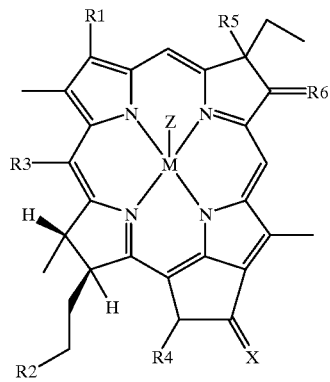

where each of R1–R6 is $CH_2CH_3$, $CH=CH_2$, $CH=CHCH_2N(CH_3)_2$, $CH=CHCH_2N^+(CH_3)_3X1^-$, $C(X2)_2C(X2)_3$, CHO, $COCH_3$, $CO_2H$, $CO_2R7$, $CONHR7$, $CH=CHCHO$, $CH_2Y$, $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, $(CH_2)_nOH$, $(CH_2)_nSH$, $(CH_2)_n$O-alkoxy, $(CH_2)_nSR7$, $(CH_2)_nOR7$, $(CH_2)_nCO_2R8$, $(CH_2)_nCONHR7$, $CO_2R7$, $CONHR7$, $CONR7R7$, $SR7$, $SO_3H$, $SO_3R7$, $SO_2NHR7$, $SO_2N(R7)_2$, a protein or biomolecule or a functional group less than or equal to 100000 daltons; X is O, $H_2$, (H, OH), S, or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons;

wherein X1 is a charge balancing ion;

X2 is halogen;

N=1, 2, 3, 4

Y=H, halogen, OH, OR7 or is a functional group less than or equal to 100000 daltons)

R7 is a functional group less than or equal to 100000 daltons

R8 is H, a physiologically acceptable salt, alkyl (1–6 carbons), aryl, substituted aryl, alkenyl, substituted alkenyl, alkynyl, or substituted alkynyl.

27. A phototherapeutic compound or composition as claimed in claim 4 having the following structure:

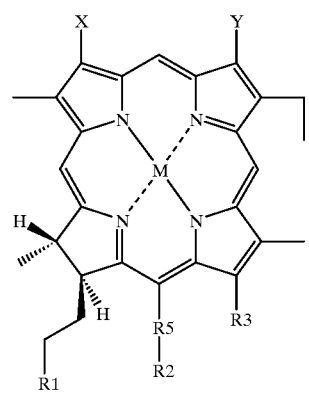

wherein, in the compound, M is $In^{113}$ or $In^{115}$ and, in the composition, M is a mixture of $In^{113}$ and $In^{115}$, and, associated therewith, a physiologically acceptable charge balancing ion, R1, R2 and R3 can be the same or different, and each is $CO_2H$, $CO_2R4$, CONHR4, $CH_2Y'$, CONR4R4, $NH_2$, $N(R4)_2$, or $N(R4)_3{}^+Z^-$, where Y' is halogen, OH, OR4, or a functional group having a molecular weight equal to or less than 100,000 daltons, R4 is a functional group having a molecular weight equal to or less than 100,000 daltons, R5 is a methylene group or an ethylene group, X is H, vinyl, ethyl, acetyl or formyl, and Y is methyl or formyl.

28. A phototherapeutic compound or composition as claimed in claim 4 having the following structure:

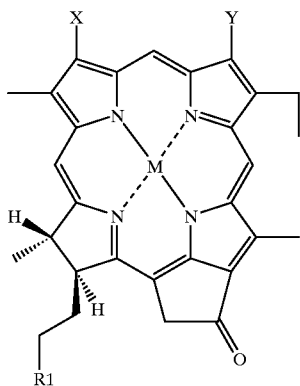

wherein, in the compound, M is $In^{113}$ or $In^{115}$ and, in the composition, M is a mixture of $In^{113}$ and $In^{115}$ and, in either case, associated therewith, a physiologically acceptable charge balancing ion, R1 is $CO_2H$, $CO_2R2$, CONHR2, $CH_2Y'$, CONR2R2, $NH_2$, $N(R2)_2$, or $N(R2)_3{}^+Z^-$, where Y' is halogen, OH, OR2, or a functional group having a molecular weight equal to or less than 100,000 daltons, and R2 is a functional group having a molecular weight equal to or less than 100,000 daltons, Z is a physiologically acceptable charge balancing ion, X is H, vinyl, ethyl, acetyl or formyl, and Y is methyl or formyl.

29. A phototherapeutic compound or composition as claimed in claim 28 wherein X is vinyl, Y is methyl, and R1 is $CO_2CH_3$.

30. A phototherapeutic compound as claimed in claim 28 wherein X is vinyl, Y is methyl, and R1 is $CO_2OH$.

31. A phototherapeutic compound as claimed in claim 28 wherein X is vinyl, Y is methyl, and R1 is CONHR4 where R4 is a functional group having a molecular weight equal to or less than 100,000 daltons.

32. A phototherapeutic compound as claimed in claim 28 wherein X is vinyl, Y is methyl, and R1 is CONHR4 or $CON(R4)_2$, where R4 is alkyl.

33. A method which comprises administering intravenously, intramuscularly, subcutaneously intraperitineally or topically to a human or animal patient a given amount of a phototherapeutic compound composed of an atom of $In^{113}$ or of $In^{115}$ complexed with the inner nitrogens of a pyrrolic core or a given amount of a phototherapeutic composition consisting essentially of a mixture of $In^{113}$ and of $In^{115}$ atoms complexed with the inner nitrogens of a pyrrolic core where, in both instances, the core is composed of at least two pyrroles whose pyrrole linking atoms are carbon, nitrogen or carbon and nitrogen, and, after a period of time, (a) examining the patient under illumination which causes amounts of the phototherapeutic compound associated with the tissue to be detected to fluoresce, or (b) irradiating target tissue in the patient with light of a wavelength which causes the phototherapeutic compound or composition associated therewith to undergo a desired reaction, the given amount of the phototherapeutic compound being sufficient to enable fluorescence or the desired reaction, but less than the amount of a compound composed of an atom of Sn complexed with the inner nitrogens of the same pyrrolic core which would be required to enable fluorescence or the desired reaction.

34. A method for treating a human or animal patient, which method comprises administering to the patient, intravenously, intramuscularly, subcutaneously, intraperitineally or topically, an effective amount of a phototherapeutic compound composed of an atom of $In^{133}$ or of $In^{115}$ complexed with the inner nitrogens of a pyrrolic core or of a phototherapeutic composition consisting essentially of a mixture of $In^{113}$ and of $In^{115}$ atoms complexed with the inner nitrogens of a pyrrolic core where, in both instances, the core is composed of at least two pyrroles whose pyrrole linking atoms may be carbon or nitrogen or combinations thereof, and, after sufficient time, irradiating target tissue with light of a wavelength which causes a reaction which destroys the target tissue, with the proviso that the amount of the phototherapeutic compound or composition administered is less than the minimum amount of a phototherapeutic compound composed of an atom of Sn complexed with the inner nitrogens of the same pyrrolic core which would be required for irradiation, after sufficient time, of the target tissue with light of a suitable wavelength to cause a reaction which would destroy the target tissue.

35. A method for detecting tissue in a human or animal patient, which method comprises administering to the patient, intravenously, intramuscularly, intraperitineally, subsutaneously or topically, an effective amount of a phototherapeutic compound composed of an atom of $In^{113}$ or of $In^{115}$ complexed with the inner nitrogens of a pyrrolic core or of a phototherapeutic composition consisting essentially of a mixture of $In^{113}$ and of $In^{115}$ atoms complexed with the inner nitrogens of a pyrrolic core where, in both instances, the core is composed of at least two pyrroles whose pyrrole linking atoms may be carbon or nitrogen or combinations thereof, and, after sufficient time, examining the patient under illumination which causes residual amounts of the phototherapeutic compound or composition to fluoresce, with the proviso that the amount of the phototherapeutic compound or composition administered is less than the minimum amount of a phototherapeutic compound composed of an atom of Sn complexed with the inner nitrogens of the same pyrrolic core which would be required for the illumination to cause residual amounts of the phototherapeutic compound to fluoresce.

36. A method as claimed in claim 33 wherein the core of the phototherapeutic compound or composition is a tetrapyrrolic core.

37. A method as claimed in claim 36 wherein the core of the phototherapeutic compound or composition is a dihydro or tetrahydro tetrapyrrolic core.

38. A method as claimed in claim 37 wherein the phototherapeutic compound or composition has a tetrapyrrolic core whose linking atoms are carbon.

39. A method as claimed in claim 34 wherein the core of the phototherapeutic compound or composition is a tetrapyrrolic core.

40. A method as claimed in claim 39 wherein the core of the phototherapeutic compound or composition is a dihydro or tetrapyrrolic core.

41. A method as claimed in claim 40 wherein the phototherapeutic compound or composition has a tetrapyrrolic core whose linking atoms are carbon.

42. A method as claimed in claim 34 wherein the phototherapeutic compound or composition has the structure of one of Compound I and Compound II, below:

Compound I

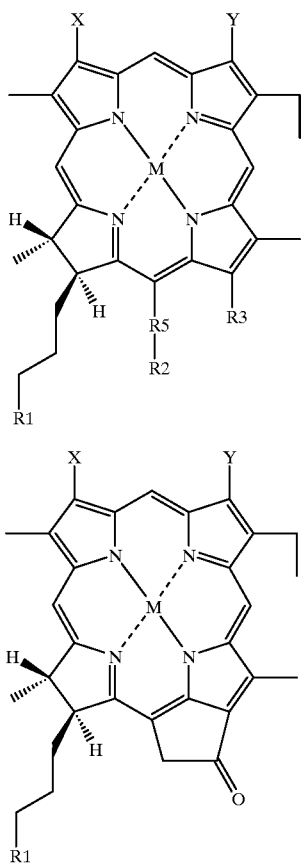

Compound II

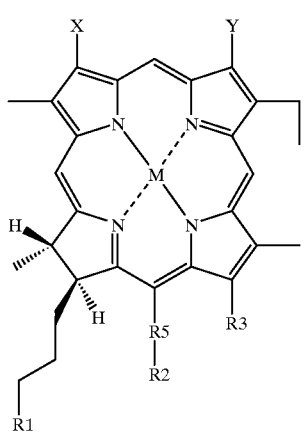

wherein M is $In^{113}$, $In^{115}$ or a mixture of $In^{113}$ and $In^{115}$ and, associated therewith, a physiologically acceptable charge balancing ion, R1, R2 and R3 can be the same or different, and each is $CO_2H$, $CO_2R4$, $CONHR4$, $CH_2Y'$, $CONR4R4$, $NH_2$, $N(R4)_2$, $N(R4)_3{}^+Z^-$, where Y is halogen, OH, OR4, or a functional group having a molecular weight equal to or less than 100,000 daltons, R4 is a functional group having a molecular weight equal to or less than 100,000 daltons, R5 is a methylene group or an ethylene group, X is H, viny, ethyl, acetyl or formyl, Y is methyl or formyl, and Z is a physiologically acceptable charge balancing ion.

43. A method as claimed in claim 37 wherein the photo-therapeutic compound or composition has the structure of one of Compound V and Compound VI, below:

Compound V

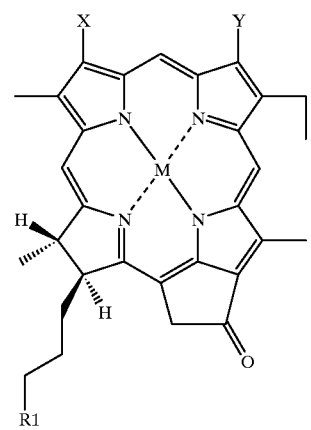

Compound VI

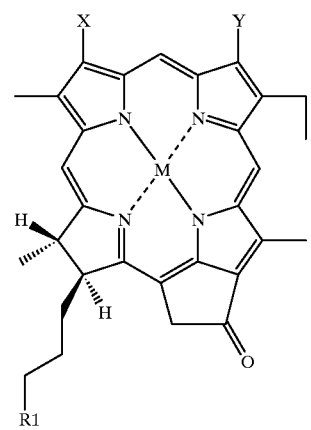

wherein M is $In^{113}$, $In^{115}$ or a mixture of $In^{113}$ and $In^{115}$ and, associated with the $In^{113}$, $In^{115}$ or mixture of $In^{113}$ and $In^{115}$, a physiologically acceptable charge balancing ion, R1 and R3 can be the same or different, and each is $CO_2CH_3$, $CO_2H$, $CO_2R4$, or an amide, where R4 is an alkyl or a phenyl group, R2 is $CO_2CH_3$, $CO_2H$, $CO_2R4$, an amide, $CH_2CO_2CH_3$, $CH_2CO_2H$, or $CH_2CO_2R4$, where R4 is an alkyl or a phenyl group, R5 is methylene or ethylene, X is H, vinyl, ethyl, acetyl or formyl, and Y is methyl or formyl.

44. A method as claimed in claim 38 wherein the photo-therapeutic compound or composition has the structure:

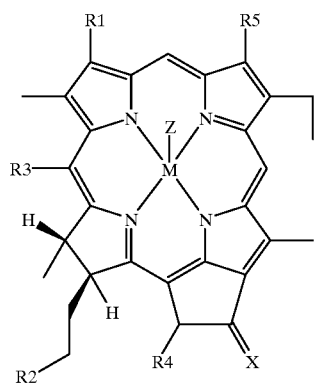

where each of R1–R5 is $CH_2CH_3$, $CH=CH_2$, $CH=CHCH_2N(CH_3)_2$, $CH=CHCH_2N^+(CH_3)_3X1^-$, $C(Y1)_2C(Y1)_3$, CHO, $COCH_3$, $CO_2H$, $CO_2R6$, CONHR7, $CH=CHCHO$, $CH_2Y$, $CH=CHCH_2OH$, $CH=CHCH_2OR6$, $CH(OH)CH_3$, $CH(OR6)CH_3$, H, halide, alkyl, cyclic alkyl (3–6 carbons), aryl, substituted aryl, alkenyl, substituted alkenyl, alkynyl, substituted alkynyl, amide, ester, NR6R6, CN, OH, OR6, $(CH_2)_nOH$, $(CH_2)_nSH$, $(CH_2)_nO$-alkoxy, $(CH_2)_nSR6$, $(CH_2)_nOR6$, $(CH_2)_nCO_2R6$, $(CH_2)_nCONHR6$, $(CH_2)_nCON(R6)_2$, $CO_2R6$, CONHR6, CONR6R6, SR6, $SO_3H$, $SO_3R6$, $SO_2NHR6$, $SO_2N(R6)_2$;

M is $In^{113}$, $In^{115}$ or a mixture of $In^{113}$ and $In^{115}$;

Z is a halide, acetate, OH, alkyl, aryl, substituted aryl, alkenyl, substituted alkenyl, alkynyl, substituted alkynyl, protein or biomolecule or functional group less than or equal to 100000 daltons;

Y1 is halogen;

Y is H, halogen, OH, OR6 or is a functional group less than or equal to 100000 daltons;

R6 is a functional group less than or equal to 100000 daltons;

R7 is H, a physiologically acceptable salt, alkyl (1–6 carbons), aryl, substituted aryl, alkenyl, substituted alkenyl, alkynyl, or substituted alkynyl;

X1 is a charge balancing ion; and

X is O, 2H, (H, OH), S, (H, OR6) or a ketone protecting group.

45. A method as claimed in claim 44 wherein, in the phototherapeutic compound or composition:

R1 is CH=CH$_2$, CHO, Et, COCH$_3$

R2 is CO$_2$CH$_3$, CO$_2$H, or an amide

R3 and R4 are H

R5 is CH$_3$

X is O

M is In$^{113}$, In$^{115}$ or a mixture of In$^{113}$ and In$^{115}$

Z is a halide, acetate or OH.

46. A method as claimed in claim 36 wherein the phototherapeutic compound or composition has the structure:

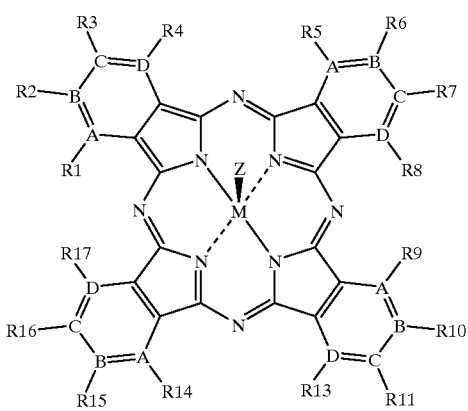

where each of R1–R17 is H, halide, alkyl, cyclic alkyl (3–6 carbons), aryl, substituted aryl, alkenyl, substituted alkenyl, alkynyl, substituted alkynyl, amide, ester, C(X)$_2$C(X)$_3$ (where X is a halogen), NR18R18, CN, OH, OR18, CHO, COCH$_3$, (CH$_2$)$_n$OH, (CH$_2$)$_n$SH, CH(OR18)CH$_3$, (CH$_2$)$_n$O-alkoxy, (CH$_2$)$_n$SR18, (CH$_2$)$_n$OR18 (where n=1, 2, 3, 4, and R18 is a functional group less than or equal to 100000 daltons), (CH$_2$)$_n$CO$_2$R19 (where R19 is H, a physiologically acceptable salt, alkyl (1–6 carbons), aryl, substituted aryl, alkenyl, substituted alkenyl, alkynyl or substituted alkynyl, and n=1, 2, 3, 4), (CH$_2$)$_n$CONHR18, (CH$_2$)$_n$CON(R18)$_2$, CO$_2$R18, CONHR18, CONR18R18, SR18 (where n=1, 2, 3, 4), SO$_3$X, SO$_3$R18, SO$_2$NHR18, SO$_2$N(R18)$_2$; A, B, C and D are C, N, O$^+$, O, S, Te, P, N$^+$(R18)X1$^-$ (where X1 is a charge balancing ion), or combinations thereof; M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, substituted alkynyl, a protein or biomolecule or functional group less than or equal to 100000 daltons.

47. A method as claimed in claim 36 wherein the phototherapeutic compound or composition has the structure:

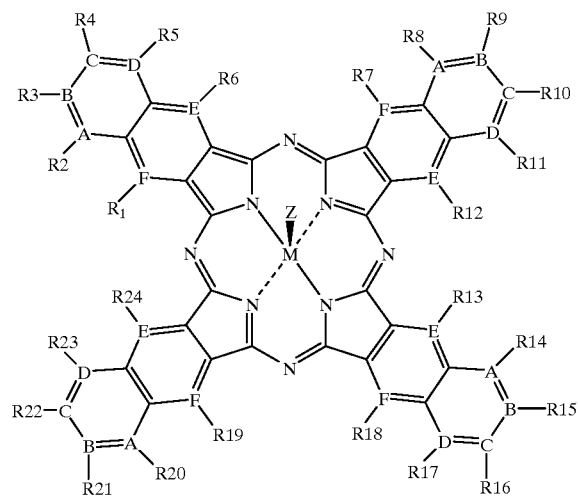

where each of R1–R24 is H, halide, alkyl, cyclic alkyl (3–6 carbons), aryl, substituted aryl, alkenyl, substituted alkenyl, alkynyl, substituted alkynyl, amide, ester, C(X)$_2$C(X)$_3$ (where X is a halogen), NR25R25, CN, OH, OR25, CHO, COCH$_3$, (CH$_2$)$_n$OH, (CH$_2$)$_n$SH, CH(OR25)CH$_3$, (CH$_2$)$_n$O-alkoxy, (CH$_2$)$_n$SR25, (CH$_2$)$_n$OR25 (where n=1, 2, 3, 4, and R25 is a functional group less than or equal to 100000 daltons), (CH$_2$)$_n$CO$_2$R26 (where R26 is H, a physiologically acceptable salt, alkyl (1–6 carbons), aryl, substituted aryl, alkenyl, substituted alkenyl, alkynyl or substituted alkynyl, and n=1, 2, 3, 4) (CH$_2$)$_n$CONHR25, (CH$_2$)$_n$CON(R25)$_2$, CO$_2$R25, CONHR25, CONR25R25, SR25, SO$_3$H, SO$_3$R25, SO$_2$NHR25, SO$_2$N(R25)$_2$; M is In$^{113}$, In$^{115}$ or a mixture of In$^{113}$ and In$^{115}$; A, B, C, D, E, F are; C, N, O$^+$, O, S, Te, P, N$^+$(R25)X1$^-$ (where X1 is a charge balancing ion), or combinations thereof; Z is a halide, acetate, OH, alkyl, aryl, substituted aryl, alkenyl, substituted alkenyl, alkynyl, substituted alkynyl, or a protein or biomolecule or functional group less than or equal to 100000 daltons.

48. A method as claimed in claim 37 wherein the phototherapeutic compound or composition has the structure:

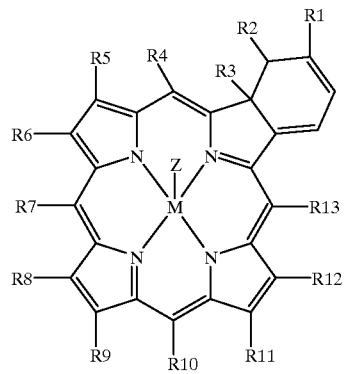

where each R1–R13 is H, halide, alkyl, vinyl, cyclic alkyl (3–6 carbons), aryl, substituted aryl, alkenyl, substituted alkenyl, alkynyl, substituted alkynyl, amide, ester, CH=CHCH$_2$N(CH$_3$)$_2$, CH=CHCH$_2$N$^+$(CH$_3$)$_3$X1$^-$ (where X1 is a charge balancing ion), C(X)₂C(X)₃ (where X is a halogen), NR14R14, CN, OH, OR14, CHO, COCH₃, (CH₂)ₙOH, (CH₂)ₙSH, (CH₂)ₙO-alkoxy, CH(OH)CH₃, CH(OR14)CH₃ (CH₂)ₙSR14, (CH₂)ₙOR14 (where n=1, 2, 3, 4, and R14 is a functional group less than or equal to 100000 daltons), (CH₂)ₙCO₂R15 (where R15 is H, a physiologically acceptable salt, alkyl (1–6 carbons), aryl, substituted aryl, alkenyl, substituted alkenyl, alkynyl, or substituted alkynyl, and n=1, 2, 3, 4), (CH₂)ₙCONHR14, (CH₂)ₙCON(R14)₂, CO₂R14, CONHR14, CONR14R14, SR14, SO₃X, SO₃R14, SO₂R14, SO₂NHR14, SO₂N(R14)₂; M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, substituted alkynyl, a protein or biomolecule or functional group less than or equal to 100000 daltons.

49. A method as claimed in claim 38 wherein the phototherapeutic compound or composition has the structure:

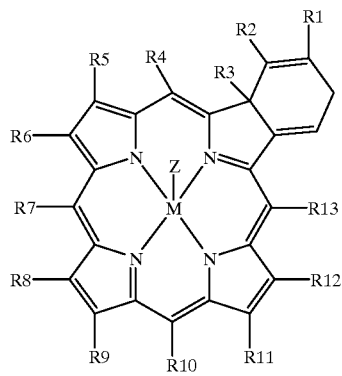

where each of R1–R13 is H, halide, alkyl, cyclic alkyl (3–6 carbons), aryl, substituted aryl, alkenyl, substituted alkenyl, alkynyl, substituted alkynyl, amide, ester, CH=CHCH₂N(CH₃)₂, CH=CHCH₂N⁺ (CH₃)₃X⁻ (where X is a charge balancing ion), C(Y)₂C(Y)₃ (where Y is a halogen), NR14R14, CN, OH, OR14, CHO, (CH₂)ₙOH, (CH₂)ₙSH, (CH₂)ₙO-alkoxy, CH(OH)CH₃, CH(OR14)CH₃ (CH₂)ₙSR14, (CH₂)ₙOR14 (where n=1, 2, 3, 4, and R14 is a functional group less than or equal to 100000 daltons), (CH₂)ₙCO₂R15 (where R15 is H, a physiologically acceptable salt, alkyl (1–6 carbons), aryl, substituted aryl, alkenyl, substituted alkenyl, alkynyl, or substituted alkynyl, and n=1, 2, 3, 4), (CH₂)ₙCONHR14, (CH₂)ₙCON(R14)₂, CO₂R14, CONHR14, CONR14R14, SR14, SO₃X1, SO₃R14, SO₂NHR14, SO₂N(R14)₂; M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, or substituted alkynyl, protein or biomolecule or functional group less than or equal to 100000 daltons.

50. A method as claimed in claim 38 wherein the phototherapeutic compound or composition has the structure:

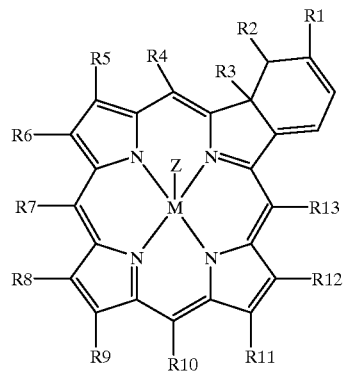

where each of R1 and R2 is CO₂R14 (where R14 is alkyl or aryl), CO₂H (or a salt thereof), SO₂Ph, CN or combinations thereof;

Each of R3, R6, R8, R12 is Me

R5 is CH=CH₂, or CH(OR14)CH₃ (where R14 is alkyl or aryl)

Each of R4, R7, R13, R10 is H

R9 and R11 are CH₂CH₂CO₂R15 (where R15 is alkyl or H or a salt of the carboxylic acid)

M is In$^{113}$, In$^{115}$ or a mixture of In$^{113}$ and In$^{115}$.

Z is a halide, acetate, or OH.

51. A method as claimed in claim 38 wherein the phototherapeutic compound or composition has the structure:

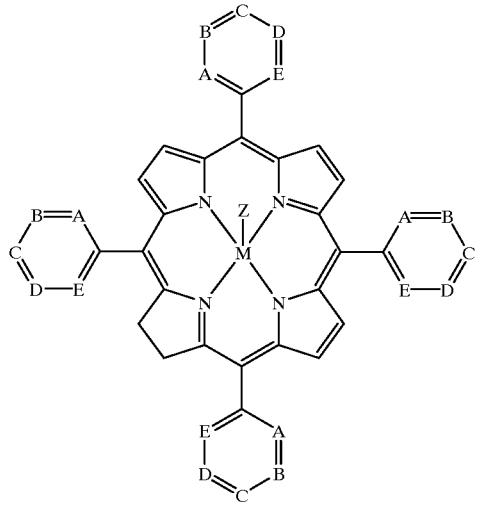

where each of A, B, C, D and E is C, N, N⁺R (where R is alkyl charged or uncharged) or combinations thereof;

M is In$^{113}$, In$^{115}$ or a mixture of In$^{113}$ and In$^{115}$ and

Z is a halide, acetate, OH.

52. A method as claimed in claim 38 wherein the phototherapeutic compound or composition has the structure:

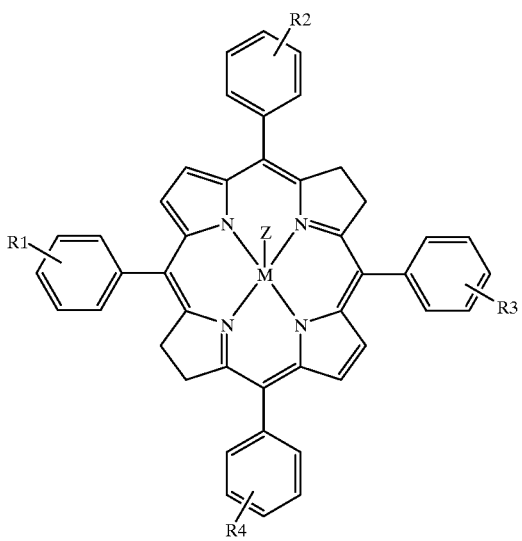

where each of R1 through R4 is $SO_3H$ (or a salt thereof), $SO_2NHR5$, $CO_2H$ (or a salt thereof), CONHR5, OH, OR5 (wherein R5 is an alcohol or ether containing group), amide, $N(CH_3)_2$, $N(Et)_2$ M is $In^{113}$, $In^{115}$ or a mixture of $In^{113}$ and $In^{115}$ Z is a halide, acetate, OH.

53. A method as claimed in claim 37 wherein the phototherapeutic compound or composition has the structure:

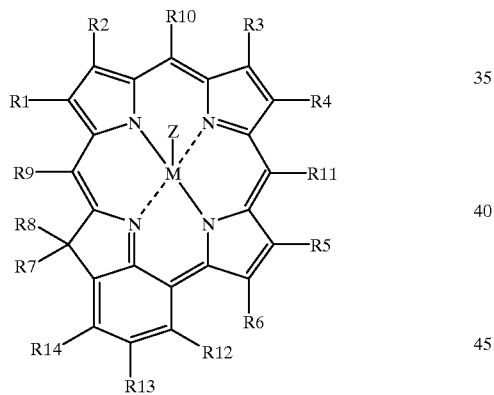

where each of R1–R14 is H, halide, methyl, ethyl, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR15R15, CN, OH, OR15, CHO, $COCH_3$, $CH(OR15)CH_3$, $(CH_2)_nOH$, $(CH_2)_nSH$, $(CH_2)_nO$-alkoxy, $(CH_2)_nSR15$, $(CH_2)_nOR15$ (where n=1, 2, 3, 4, and R15 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl and n=1, 2, 3, 4), $(CH_2)_nCONHR15$, $(CH_2)_nCON(R15)_2$, $CO_2R15$, CONHR15, CONR15R15, SR15 (where n=1, 2, 3, 4), $SO_3H$, $SO_3R16$, $SO_2NHR15$, $SO_2N(R15)_2$; M is $In^{113}$, $In^{115}$ or a mixture of $In^{113}$ and $In^{115}$ Z is a halide, acetate, OH, alkyl, aryl, substituted aryl, alkenyl, substituted alkenyl, alkynyl, substituted alkynyl, or a functional group less than or equal to 100000 daltons, a protein or a biomolecule.

54. A method as claimed in claim 38 wherein the phototherapeutic compound or composition has the structure:

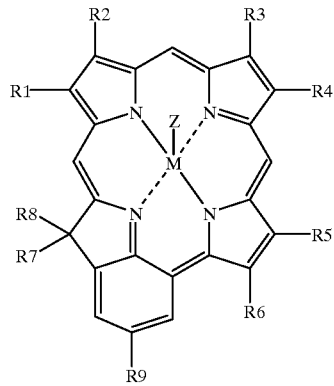

where each of R1–R8 is ethyl or methyl

R9 is $CH_3$, $SO_2NH(CH_2CH_2O)_n CH_3$ (n=1 to 1000), $SO_2N((CH_2CH_2O)_nCH_3)_2$ (n=1 to 1000); $SO_2NH(CH_2)_nOH$ (n=1 to 1000), $CH_3$, $SO_2N((CH_2,CH_2)_nOH)_2$ (n=1 to 1000); $SO_2NC((N(CH_3)_2)_2$; $SO_2NH(CH_2)_nN(CH_3)_2$ (n=1 to 1000); $SO_2NH(CH_2)_nSH$ (n=1 to 1000); $SO_2NHC(CH_2CH_2OH)_3$; $SO_2NHCH_2CO_2H$ (or salts thereof); $SO_2NH(CH_2)_nCH(NH_2)CO_2H$ (or salts thereof) (n=1 to 5); $SO_2NHCH_2CO_2R10$ (R10 is alkyl, aryl); $SO_2NH(CH_2)_nCH(NH_2)CO_2R10$ (R10 is alkyl, aryl) (n=1 to 5)

M is $In^{113}$, $In^{115}$ or a mixture of $In^{113}$ and $In^{115}$ Z is a halide, acetate, OH.

55. A method as claimed in claim 38 wherein the phototherapeutic compound or composition has the structure:

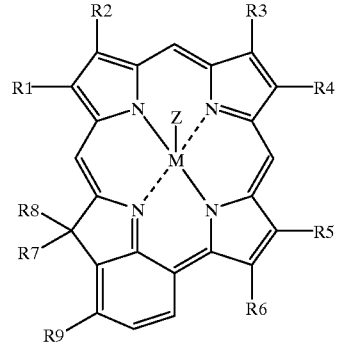

where each of R1–R8 is ethyl or methyl.

R9 is $CH_2CONH(CH_2CH_2O)_nCH_3$ (n=1 to 1000), $CH_2CON((CH_2CH_2O)_nCH_3)_2$ ($_n$=1 to 1000); $CH_2CONH(CH_2)_nOH$ (n=1 to 1000), $CH_2CON((CH_2CH_2)_nOH)_2$ (n=1 to 1000); $CH_2CONC((N(CH_3)_2)_2$; $CH_2CONH(CH_2)_nN(CH_3)_2$ (n=1 to 1000); $CH_2CONH(CH_2)_nSH$ (n=1 to 1000); $CH_2CONHC(CH_2CH_2OH)_3$; $CH_2CONHCH_2CO_2H$; (or salts thereof); $CH_2CONH(CH_2)_nCH(NH_2)CO_2H$ (n=1 to 5); $CH_2CONHCH_2CO_2R10$ (R10 is alkyl, aryl); $CH_2CONH(CH_2)_nCH(NH_2)CO_2R10$ (R10 is alkyl, aryl) (n=1 to 5)

M is $In^{113}$, $In^{115}$ or a mixture of $In^{113}$ and $^{115}$.

Z is a halide, acetate, OH.

56. A method as claimed in claim 38 wherein the phototherapeutic compound or composition has the structure:

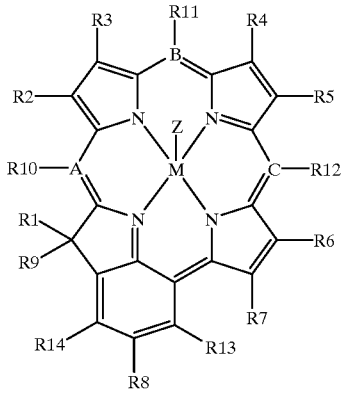

where each of R1–R14 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3X^-$ (where X is a charge balancing ion), $C(X1)_2C(X1)_3$ (where X1 is a halogen), NR15R15, CN, OH, OR15, CHO, $(CH_2)_nOH$, $(CH_2)_nSH$, $(CH_2)_nO$-alkoxy, $CH(OH)CH_3$, $CH(OR15)CH_3$ $(CH_2)_nSR15$, $(CH_2)_nOR15$ (where n=1, 2, 3, 4, and R15 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl, and n=1, 2, 3, 4), $(CH_2)_nCONHR15$, $(CH_2)_nCON(R15)_2$, $CO_2R15$, CONHR15, CONR15R15, SR15, $SO_3H$, $SO_3R15$, $SO_2NHR15$, $SO_2N(R15)_2$; A, B, C are C, N, $O^+$, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons.

57. A method as claimed in claim 38 wherein the phototherapeutic compound or composition has the structure:

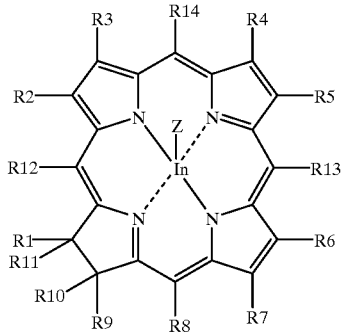

where each of R1 through R14 is H, halide, alkyl, cyclic alkyl (1–6 carbons), aryl, substituted aryl, alkenyl, substituted alkenyl, alkynyl, substituted alkynyl, amide, ester, $C(X1)_2C(X1)_3$ (where X1 is a halogen), NR15R15, CN, OH, OR15, CHO, $COCH_3$, $(CH_2)_nOH$, $(CH_2)_nSH$, $(CH_2)_nO$-alkoxy, $(CH_2)_nSR15$, $(CH_2)_nOR15$ (where n=1, 2, 3, 4, and R15 is a functional group less than or equal to 100000 daltons), $(CH_2)_nCO_2R16$ (where R16 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR15$, $(CH_2)_nCON(R15)_2$, $CO_2R15$, CONHR15, $CON(R15)_2$, SR15, $SO_3H$, $SO_3R15$ $SO_2NHR15$, $SO_2N(R15)_2$; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl or substituted alkynyl, or a functional group less than or equal to 100000 daltons, protein or biomolecule.

58. A method as claimed in claim 38 wherein the phototherapeutic compound or composition has the structure:

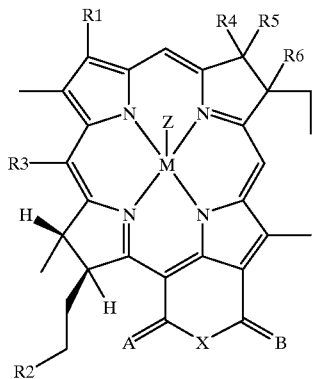

wherein;
R1 is $CH=CH_2$, Et, CHO, or $COCH_3$
R4 is Me
R3 is H
each of R5 and R6 is OH
R2 is $CO_2CH_3$, $CO_2H$, $CO_2R7$ (R7 is all or phenyl), or an amide
Each of A and B is O or NR8 (R8 is alkyl)
X is O or NR9 (R9 is alkyl, an amino acid, an alcohol containing group, or an ether containing group)
M is $In^{113}$, $In^{115}$ or a mixture of $In^{113}$ and $In^{115}$
Z is a halide, acetate, or OH.

59. A method as claimed in claim 38 wherein the phototherapeutic compound or composition has the structure:

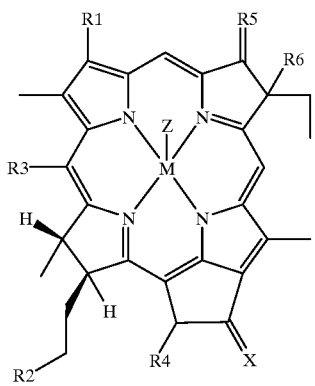

where each of R1–R6 is $CH_2CH_3$, $CH=CH_2$, $CH=CHCH_2N(CH_3)_2$, $CH=CHCH_2N^+(CH_3)_3X1^-$, $C(X2)_2C(X2)_3$, CHO, $COCH_3$, $CO_2H$, $CO_2R7$, CONHR7, $CH=CHCHO$, $CH_2Y$, $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, $(CH_2)_nOH$, $(CH_2)_nSH$, $(CH_2)_nO$-alkoxy, $(CH_2)_nSR7$, $(CH_2)_nOR7$, $(CH_2)_nCO_2R7'$, $(CH_2)_nCONHR7$, $CO_2R7$, CONHR7, CONR7R7, SR7, $SO_3H$, $SO_3R7$, $SO_2NHR7$, $SO_2N(R7)_2$, a protein or biomolecule or a functional group less than or equal to 100000 daltons; X is O, $H_2$, (H, OH), S, or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkenyl, substituted alkynyl, protein or biomolecule or functional group less than or equal to 100000 daltons
wherein X1 is a charge balancing ion
R7 is a fuictional group less than or equal to 100000 daltons
Y=H, halogen, OH, OR7 or is a functional group less than or equal to 100000 daltons
X2 is a halogen
n=1, 2, 3, 4, and
R7' is H, a physiologically acceptable salt, alkyl (1–6 carbons), aryl, substituted aryl, alkenyl, substituted alkenyl, alkynyl or substituted alkynyl.

60. A method as claimed in claim 38 wherein the phototherapeutic compound or composition has the structure:

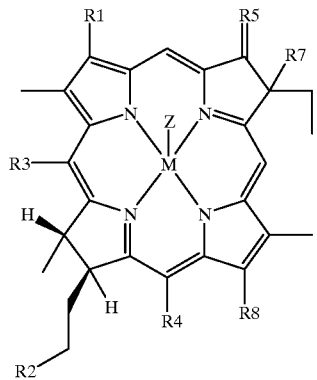

where each of R1–R8 is $CH_2CH_3$, $CH=CH_2$, $CH=CHCH_2N(CH_3)_2$, $CH=CHCH_2N^+(CH_3)_3X^-$, $C(X1)_2C(X1)_3$, CHO, $COCH_3$, $CO_2H$, $CO_2R9$, CONHR9, $CH=CHCHO$, $CH_2Y$, $CH_2CO_2R9$, $CH_2CONHR9$, $CH=CHCH_2OH$, $CH=CHCH_2OR9$, $CH(OH)CH_3$, $CH(OR9)CH_3$, H, halide, alkyl, cyclic alkyl (3–6 carbons), aryl, substituted aryl, alkenyl, substituted alkenyl, alkynyl, substituted alkynyl, amide, ester, NR9R9, CN, O, S, NHR9, OH, OR9, CHO, $(CH_2)_nOH$, $(CH_2)_nSH$, $(CH_2)_nO$-alkoxy, $(CH_2)_nSR9$, $(CH_2)_nOR9$, $(CH_2)_nCO_2R9'$, $(CH_2)_nCONHR9$, $(CH_2)_nCON(R9)_2$, $CO_2R9$, CONHR9, CONR9R9, SR9, $SO_3H$, $SO_3R9$, $SO_2NHR9$, $SO_2N(R9)_2$, protein or biomolecule or functional group less than or equal to 100000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, a protein or biomolecule or functional group less than or equal to 100000 daltons,
wherein X is a charge balancing ion
R9 is a functional group less than or equal to 100000 daltons
Y=H, halogen, OH, OR9 or is a functional group less than or equal to 100000 daltons
X1 is a halogen
n=1, 2, 3,4, and
R9' is H, a physiologically acceptable salt, alkyl (1–6 carbons), aryl, substituted aryl, alkenyl, substituted alkenyl, alkynyl or substituted alkynyl.

61. A method as claimed in claim 38 wherein the phototherapeutic compound or composition has the structure:

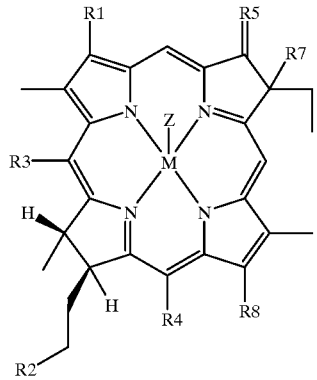

wherein;
R1 is $CH=CH_2$, Et, CHO, or $COCH_3$
R4 is O or NR9 (where R9 is alkyl)
R5 is Me
R3 is H
R4 and R8 are H, $CO_2CH_3$, $CO_2H$ (or a salt thereof), $CO_2R10$ (R10 is an alkyl or phenyl group), an amide, $CH_2CO_2CH_3$, $CH_2CO_2H$ (or a salt thereof),
R2 is $CO_2CH_3$, $CO_2H$, $CO_2R10$ (R10 is an alkyl or a phenyl group), or an amide,
M is $In^{113}$, $In^{115}$ or a mixture of $In^{113}$ and $In^{115}$, and
Z is a halide, acetate, or OH.

62. A method as claimed in claim 38 wherein the phototherapeutic compound or composition has the structure:

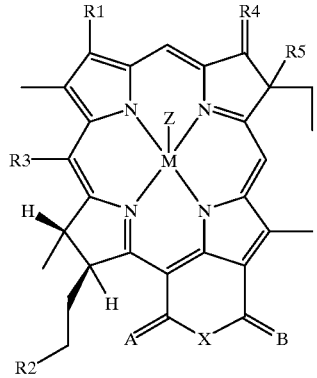

where each of R1–R5 is $CH_2CH_3$, $CH=CH_2$, $CH=CHCH_2N(CH_3)_2$, $CH=CHCH_2N^+(CH_3)_3$ $X1^-$, $C(X2)_2C(X2)_3$, CHO, $COCH_3$, $CO_2H$, $CO_2R6$, CONHR6, $CH=CHCHO$, $CH_2Y$, $CH_2CO_2R6$, $CH_2CONHR6$, $CH=CHCH_2OH$, $CH(OH)CH_3$, $CH(OR6)CH_3$, H, halide, alkyl, cyclic alkyl (3–6 carbons), aryl, substituted aryl, alkenyl, substituted alkenyl, alkynyl, substituted alkynyl, amide, ester, NR6R6, CN, O, S, NHR6, OH, OR6, CHO, $(CH_2)_nOH$, $(CH_2)_nSH$, $(CH_2)_nO$-alkoxy, $(CH_2)_nSR6$, $(CH_2)_nOR6$, $(CH_2)_nCO_2R7$, $(CH_2)_nCONHR6$, $CO_2R6$, CONHR6, CONR6R6, SR6, $SO_3H$, $SO_3R6$, $SO_2NHR6$, $SO_2N(R6)_2$, a protein or biomolecule or a functional group less than or equal to 100000 daltons; X is O, NR8; Z is a halide, acetate, OH, alkyl, aryl, substituted aryl, alkenyl, substituted alkenyl, alkynyl, substituted alkynyl, protein or biomolecule or functional group less than or equal to 100000 daltons
wherein X1 is a charge balancing ion
R6 is a functional group less than or equal to 100000 daltons Y=H, halogen, OH, OR6 or is a functional group less than or equal to 100000 daltons X2 is a halogen n=1, 2, 3, 4, and R7 is H, a physiologically acceptable salt, alkyl (1–6 carbons), aryl, substituted aryl, alkenyl, substituted alkenyl, alkynyl or substituted alkynyl R8 is H, alkyl (1–10 carbons), aryl, substituted aryl, alkenyl, substituted alkenyl, alkynyl, substituted alkynyl, an amino acid, an amino acid ester or a functional group equal to or less than 100000 daltons.

63. A method as claimed in claim 38 wherein the phototherapeutic compound or composition has the structure:

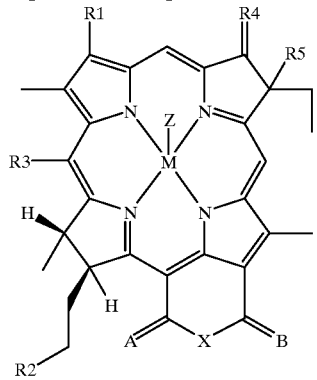

wherein:

R1 is CH=CH$_2$, Et, CHO, or COCH$_3$

R4 is O or NR6 (where R6 is alkyl)

R5 is Me

R3 is H

R2 is CO$_2$CH$_3$, CO$_2$H, CO$_2$R7 (R7 is an alkyl or a phenyl group), or an amide X is O, NR8 (R8 is alkyl, an amino acid, an alcohol containing group, or an ether containing group)

M is In$^{113}$, In$^{115}$ or a mixture of In$^{113}$ and In$^{115}$

Z is a halide, acetate, OH, and

A and B are O or NR9 where R9 is alkyl.

64. A method as claimed in claim 38 wherein the phototherapeutic compound or composition has the structure:

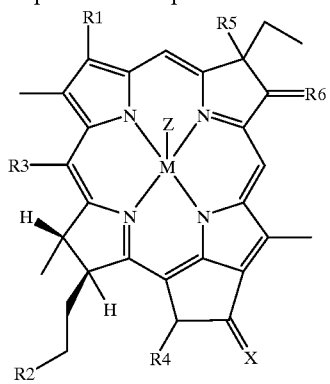

where each of R1–R6 is CH$_2$CH$_3$, CH=CH$_2$, CH=CHCH$_2$N(CH$_3$)$_2$, CH=CHCH$_2$N$^+$(CH$_3$)$_3$X1$^-$ C(X2)$_2$C(X2)$_3$, CHO, COCH$_3$, CO$_2$H, CO$_2$R7, CONHR7, CH=CHCHO, CH$_2$Y, CH$_2$CO$_2$R7, CH$_2$CONHR7, CH=CHCH$_2$OH, CH=CHCH$_2$OR7, CH(OH)CH$_3$, CH(OR7)CH$_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, (CH$_2$)$_n$OH, (CH$_2$)$_n$SH, (CH$_2$)$_n$O-alkoxy, (CH$_2$)$_n$SR7, (CH$_2$)$_n$OR7, (CH$_2$)$_n$CO$_2$R8, (CH$_2$)$_n$CONHR7, CO$_2$R7, CONHR7, CONR7R7, SR7, SO$_3$H, SO$_3$R7, SO$_2$NHR7, SO$_2$N(R7)$_2$, a protein or biomolecule or a functional group less than or equal to 100000 daltons; X is O, H$_2$, (H, OH), S, or a ketone protecting group; M is In$^{113}$, In$^{115}$ or a mixture of In$^{113}$ and In$^{115}$; Z is a halide, acetate, OH, alkyl, aryl, substituted aryl, alkenyl, substituted alkenyl, alkynyl, substituted alkynyl, protein or biomolecule or functional group less than or equal to 100000 daltons;

wherein X1 is a charge balancing ion;

X2 is halogen;

n=1, 2, 3, 4

Y=H, halogen, OH, OR7 or is a functional group less than or equal to 100000 daltons)

R7 is a functional group less than or equal to 100000 daltons

R8 is H, a physiologically acceptable salt, alkyl (1–6 carbons), aryl, substituted aryl, alkenyl, substituted alkenyl, alkynyl, or substituted alkynyl.

65. A method as claimed in claim 41 wherein the phototherapeutic compound or composition has the structure of one of Compound I and Compound II, below:

Compound I

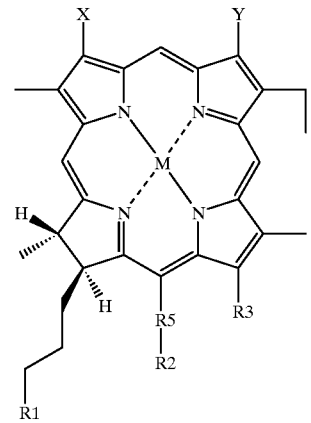

Compound II

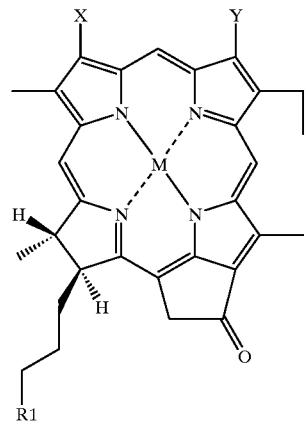

wherein M is In$^{113}$, In$^{115}$ or a mixture of In$^{113}$ and In$^{115}$ and, associated therewith, a physiologically acceptable charge balancing ion, R1 and R3 can be the same or different, and each is CO$_2$H, CO$_2$R4, CONHR4, CH$_2$Y', CONR4R4, NH$_2$, N(R4)$_2$, or N(R4)$_3$$^+$Z$^-$, where Y' is hlogen, OH, OR4, or a functional group having a molecular weight equal to or less than 100,000 daltons, R4 is a functional group having a molecular weight equal to or less than 100,000 daltons, R5 is a methylene group or an ethylene group, X is H, vinyl, ethyl, acetyl or formyl, Z is a physiologically acceptable charge balancing ion, and Y is methyl or formyl.

66. A method as claimed in claim 41 wherein the phototherapeutic compound or composition has the structure of one of Compound V and Compound VI, below:

Compound V

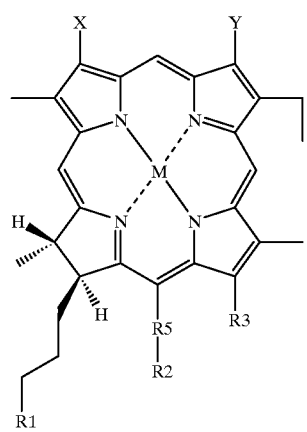

Compound VI

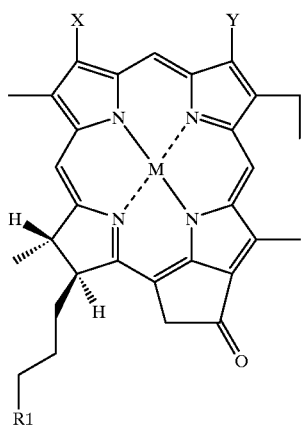

wherein M is $In^{113}$, $In^{115}$ or a mixture of $In^{113}$ and $In^{115}$ and, associated with the $In^{113}$, $In^{115}$ or mixture of $In^{113}$ and $In^{115}$, a physiologically acceptable charge balancing ion, R1 and R3 can be the same or different, and each is $CO_2CH_3$, $CO_2H$, $CO_2R4$, or an amide, where R4 is an alkyl or a phenyl group, R2 is $CO_2CH_3$, $CO_2H$, $CO_2R4$, an amide, $CH_2CO_2CH_3$, $CH_2CO_2H$, or $CH_2CO_2R4$, where R4 is an alkyl or a phenyl group, R5 is methylene or ethylene, X is H, vinyl, ethyl, acetyl or formyl, and Y is methyl or formyl.

67. A method as claim in claim 41 wherein the phototherapeutic compound or composition has the structure:

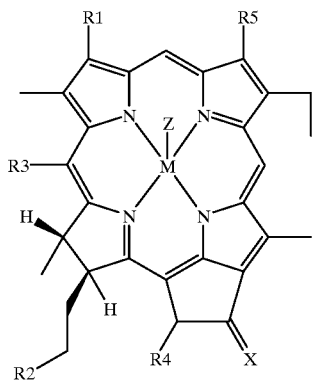

where each of R1–R5 is $CH_2CH_3$, $CH=CH_2$, $CH=CHCH_2N(CH_3)_2$, $CH=CHCH_2N^+(CH_3)_3X1^-$, $C(Y1_2C(Y1)_3$, $CHO, COCH_3$, $CO_2H$, $CO_2R6$, $CONHR7$, $CH=CHCHO$, $CH_2Y$, $CH=CHCH_2OH$, $CH=CHCH_2OR6$, $CH(OH)CH_3$, $CH(OR6)CH_3$, H, halide, alkyl, cyclic alkyl (3–6 carbons), aryl, substituted aryl, alkenyl, substituted alkenyl, alkynyl, substituted alkynyl, amide, ester, NR6R6, CN, OH, OR6, $(CH_2)_nOH$, $(CH_2)_nSH$, $(CH_2)_nO$-alkoxy, $(CH_2)_nSR6$, $(CH_2)_nOR6$, $(CH_2)_nCO_2R6$, $(CH_2)_nCONHR6$, $(CH_2)_nCON(R7)_2$, $CO_2R6$, $CONHR6$, $CONR6R6$, $SR6$, $SO_3H$, $SO_3R6$, $SO_2NHR6$, $SO_2N(R6)_2$;

M is $In^{113}$, $IN^{115}$ or a mixture of $In^{113}$ and $In^{115}$;

Z is a halide, acetate, OH, alkyl, aryl, substituted aryl, alkenyl, substituted alkenyl, alkynyl, substituted alkynyl, protein or biomolecule or functional group less than or equal to 100,000 daltons;

Y is H, halogen, OH, OR6 or is a functional group less than or equal to 100,000 daltons;

R6 is a functional group less than or equal to 100,000 daltons;

R7 is H, a physiologically acceptable salt, alkyl (1–6 carbons), aryl, substituted aryl, alkenyl, substituted alkenyl, alkynyl, or substituted alkynyl;

Y1 is a halogen;

X1 is a charge balancing ion; and

X is O, 2H, (H, OH), S, (H, OR6) or a ketone protecting group.

68. A method as claimed in claim 67 wherein, in the phototherapeutic compound or composition:

R1 is $CH=CH_2$, CHO, Et, $COCH_3$

R2 is $CO_2CH_3$, $CO_2H$, or an amide

R3 and R4 are H

R5 is $CH_3$

X is O

M is $In^{113}$, $In^{115}$ or a mixture of $In^{113}$ and $In^{115}$

Z is a halide, acetate or OH.

69. A method as claimed in claim 39 wherein the phototherapeutic compound or composition has the structure:

125

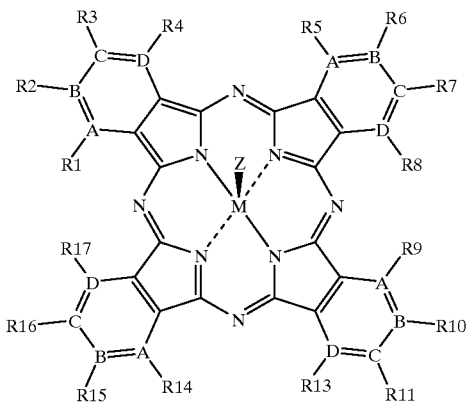

where each of R1–R17 is H, halide, alkyl, cyclic alkyl (3–6 carbons), aryl, substituted aryl, alkenyl, substituted alkenyl, substituted alkynyl, amide, ester, $C(X)_2C(X)_3$ (where X is a halogen), NR18R18, CN, OH, OR18, CHO, $COCH_3$, $(CH_2)_nOH$, $(CH_2)_nSH$, $CH(OR18)CH_3$, $(CH_2)_nO$-alkoxy, $(CH_2)_nSR18$, $(CH_2NOR18$(where n=1, 2, 3, 4, and R18 is a functional group less than or equal to 100,000 daltons), $(CH_2)_nCO_2R19$ (where R19 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR18$, $(CH_2)CON(R18_2$, $CO_2R18$, CONHR18, CONR18R18, Sr18 (where n=1, 2, 3, 4), $SO_3X1$, $SO_3R18$, $SO_2NHR18$, $SO_2N(R18)_2$; A, B, C and D are C, N, $O^+$, O, S, Te, P, $N^+(R18)X1^-$ (where X1 is a charge balancing ion), or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, a protein or biomolecule or functional group less than or equal to 100,000 daltons.

70. A method as claimed in claim 39 wherein the photo-therapeutic compound or composition has the structure:

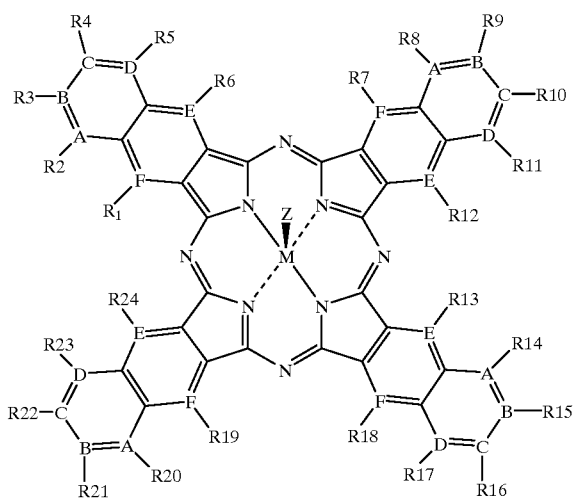

where each of R1–R24 is H, halide, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR25R25, CN, OH, OR25, CHO, $COCH_3$, $(CH_2)_nOH$, $(CH_2)_nSH$, $CH(OR25)CH_3$, $(CH_2)_nO$-alkoxy, $(CH_2nSR25$, $(CH_2)_nOR25$ (where n=1, 2, 3, 4, and R25 is a functional group less than or equal to 100,000 daltons), $(CH_2)_nCO_2R26$ (where R26 is H, a physiologically acceptable salt, alkyl (1–6 carbons), aryl, substituted aryl, alkenyl, substituted alkenyl, alkynyl or substituted alkynyl, and n=1, 2, 3, 4), $(CH_2)_nCONHR25$, $(CH_2)_nCON(R25)_2$, $CO_2R25$, CONHR25, CONR25R25, SR25, $SO_3H$, $SO_3R26$, $SO_2NHR25$, $SO_2N(R25)_2$; M is $In^{113}$, $In^{115}$ or a mixture of $In^{113}$ and $In^{115}$;

A, B, C, D, E, F are C, N, $O^+$, O, S, Te, P, $N^{+(R}25)X1^-$ (where X1 is a charge balancing ion), or combinations thereof; Z is a halide, acetate, OH, alkyl aryl, substituted aryl, alkenyl, substituted alkenyl, alkynyl, substituted alkynyl, or a protein or biomolecule or functional group less than or equal to 100,000 daltons.

71. A method as claimed in claim 41 wherein the photo-therapeutic compound or composition has the structure:

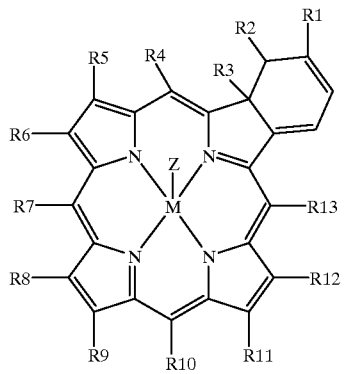

where each R1–R13 is H, halide, alkyl, vinyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3$ $X1^-$ (where X1 is a charge balancing ion), $C(X)_2C(X)_3$ (where X is a halogen), NR14R14, Cn, OH, OR14, CHO, $COCH_3$, $(CH_2)_nOH$, $(CH_2)_nSH$, $(CH_2)_nO$-alkoxy, $CH(OH)CH_3$, $CH(OR14)CH_3$ $(CH_2)_nSR14$, $(CH_2)_nOR14$ (where n=1, 2, 3, 4, and R14 is a functional group less than or equal to 100,000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR14$, $(CH_2)_nCON(R14)_2$, $CO_2R14$, CONHR14, CONR14R14, SR14, $SO_3X1$, $SO_3R14$, $SO_2R14$, $SO_2NHR14$, $SO_2N(R14)_2$; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, a protein or biomolecule or functional group less than or equal to 100,000 daltons.

72. A method as claimed in claim 41 wherein the photo-therapeutic compound or composition has the structure:

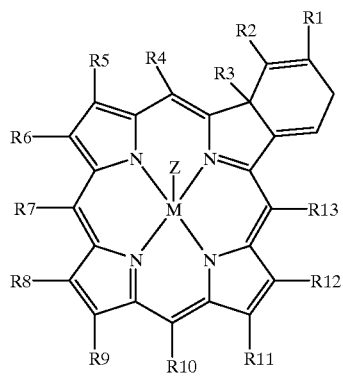

where each of R1–R13 is H, halide, alkyl, cyclic alkyl (3–6 carbons), aryl, substituted aryl, alkenyl, substituted alkenyl, alkynyl, substituted alkynyl, amide, ester, $CH=CHCH_2N(CH_3)_2$, $CH=CHCH_2N^+(CH_3)_3 \ X^-$ (where X is a charge balancing ion), $C(Y)_2C(Y)_3$ (where Y is a halogen), $NR14R14$, CN, OH, OR14, CHO, $(CH_2)_nOH$, $(CH_2)_nSH$, $(CH_2)_n$O-alkoxy, $CH(OH)CH_3$, $CH(OR14)CH_3$ $(CH_2)_nSR14$, $(CH_2)_nOR14$ (where n=1, 2, 3, 4, and R14 is a functional group less than or equal to 100,000 daltons), $(CH_2)_nCO_2R15$ (where R15 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR14$, $(CH_2)_nCON(R14)_2$, $CO_2R14$, $CONHR14$, $CONR14R14$, $SR14$, $SO_3H$, $SO_3R14$, $SO_2NHR14$, $SO_2N(R14)_2$; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, or substituted alkynyl, protein or biomolecule or functional group less than or equal to 100,000 daltons.

73. A method as claimed in claim 41 wherein the photo-therapeutic compound or composition has the structure:

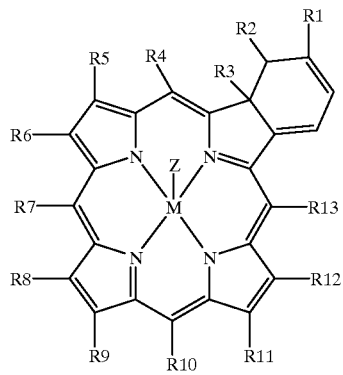

where each of R1 and R2 is $CO_2R14$ (where R14 is alkyl or aryl), $CO_2H$ (or a salt thereof, $SO_2Ph$, CN or combinations thereof;
Each of R3, R6, R8, R12 is Me.
R5 is $CH=CH_2$, or $CH(OR14)CH_3$ (where R14 is alkyl or aryl)
Each of R4, R7, R13, R10 is H
R9 and R11 are $CH_2CH_2CO_2R15$ (where R15 is alkyl or H or a salt of the carboxylic acid),
M is $In^{113}$, $In^{115}$ or a mixture of $In^{113}$ and $In^{115}$,
Z is a halide, acetate, or OH.

74. A method as claimed in claim 41 wherein the photo-therapeutic compound or composition has the structure:

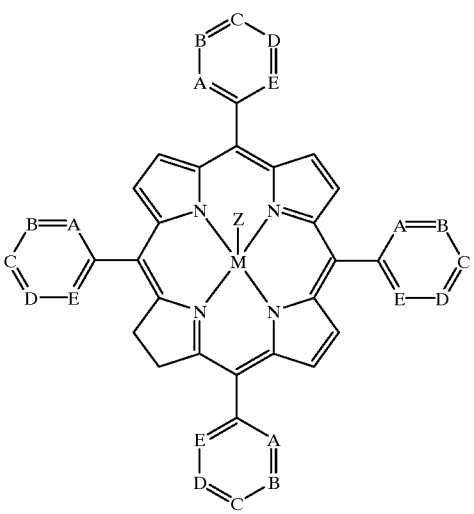

where each of A, B, C, D and E is C, N, $N^+R$ (where R is alkyl charged or uncharged) or combinations thereof;

M is $In^{113}$, $In^{115}$ or a mixture of $In^{113}$ and $In^{115}$ and

Z is a halide, acetate, OH.

75. A method as claimed in claim 41 wherein the photo-therapeutic compound or composition has the structure:

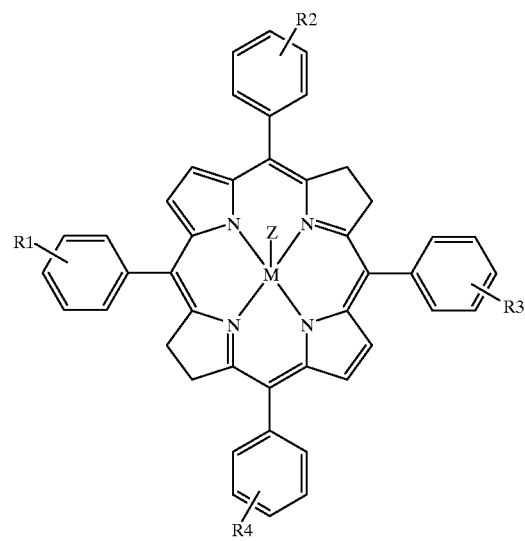

where each of R1 through R4 is $SO_3H$ (or a salt thereof), $SO_2NHR5$, $CO_2H$ (or a salt thereof), $CONHR5$, OH, OR5 (wherein R5 is an alcohol or ether containing group), amide, $N(CH_3)_2$, $N(Et)_2$ M is $In^{113}$, $In^{115}$ or a mixture of $In^{113}$ and $In^{115}$ Z is a halide, acetate, OH.

76. A method as claimed in claim 41 wherein the photo-therapeutic compound or composition has the structure:

129

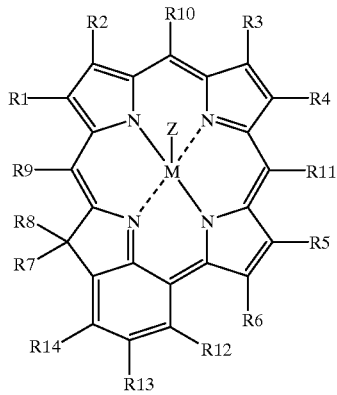

where each of R1–R14 is H, halide, methyl, ethyl, alkyl, cyclic alkyl (3–6 carbons), aryl, substituted aryl, alkenyl, substituted alkenyl, alkynyl, substituted alkynyl, amide, ester, $C(X)_2C(X)_3$ (where X is a halogen), NR15R15, CN, OH, OR15, CHO, COCH$_3$, CH(OR15)CH$_3$, $(CH_2)_nOH$, $(CH_2)_nSH$, $(CH_2)_nO$-alkoxy, $(CH_2nSR15$, $(CH_2)_nOR15$ (where n=1, 2, 3, 4, and R15 is a functional group less than or equal to 100,000 daltons), $(CH_2)_nCO_2R16$ (where R16 is H, a physiologically acceptable salt, alkyl (1–6 carbons), aryl, substituted aryl, alkenyl, substituted alkenyl, alkynyl, and n=1, 2, 3, 4), $(CH_2)_nCONHR15$, $(CH_2)_nCON(R15)_2$, $CO_2R15$, CONHR15, CONR15R15, SR15 (where n=1, 2, 3, 4), $SO_3H$, $SO_3R16$, $SO_2NHR15$, $SO_2(R15)_2$; M is $In^{113}$, $In^{115}$ or a mixture of $In^{113}$ and $In^{115}$ Z is a halide, acetate, OH, alkyl, alkyl, aryl, substituted aryl, alkenyl, substituted alkenyl, alkynyl, substituted alkynyl, or a functional group less than or equal to 100,000 daltons, a protein or a biomolecule.

77. A method as claim in claim 41 wherein the phototherapeutic compound or composition has the structure:

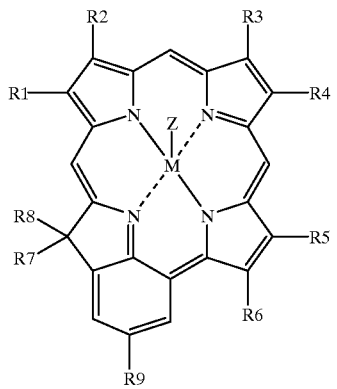

where each of R1–R8 is ethyl or methyl
R9 is CH$_3$, $SO_2NH(CH_2CH_2O)_nCH_3$ (n=1 to 1,000), $SO_2N((CH_2CH_2O)_nCH_3)_2$ (n=1 to 1,000); $SO_2NH(CH_2)_nOH$ (n=1 to 1,000), CH$_3$, $SO_2N((CH_2CH_2NOH)_2$ (n=1 to 1,000); $SO_2NC((N(CH_3)_2)_2$; $SO_2NH(CH_2)_nN(CH_3)_2$ (n=1 to 1,000); $SO_2NH(CH_2)_nSH$ (n=1 to 1,000); $SO_2NHC(CH_2CH_2OH)_3$; $SO_2NHCH_2CO_2H$ (or salts thereof; $SO_2NH(CH_2)_nCH(NH_2)CO_2H$ (or salts thereof) (n=1 to 5); $SO_2NHCH_2CO_2R10$ (R10 is alkyl, aryl); $SO_2NH(CH_2)_nCH(NH_2)CO_2R10$ (R10 is alkyl, aryl) (n=1 to 5) M is $In^{113}$, $In^{115}$ or a mixture of $In^{113}$ and $In^{115}$ Z is a halide, acetate, OH.

78. A method as claimed in claim 41 wherein the phototherapeutic compound or composition has the structure:

130

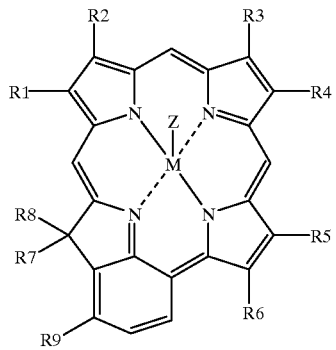

where each of R1–R8 is ethyl or methyl,
R9 is $CH_2CONH(CH_2CH_2O)_nCH_3$(n=1 to 1,000), $CH_2CON((CH_2CH_2O)_nCH_3)_2$ (n=1 to 1,000); $Ch_2CONH(CH_2)_nOH$ (n=1 to 1,000), $CH_2CON((CH_2CH_2)_nOH)_2$ (n=1 to 1,000); $CH_2CONC(N(CH_3)_2)_2$; $CH_2CONH(CH_2)_nN(CH_3)_2$ (n=1 to 1,000); (N=1 to 1,000); $CH_2CONHC(CH_2CH_2OH)_3$; $CH_2CONHCH_2CO_2H$; (or salts thereof) $CH_2CONH(CH_2)_nCH(NH_2)CO_2H$ (n=1 to 5); $CH_2CONHCH_2CO_2R10$ (R10 is alkyl, aryl); $CH_2CONH(CH_2)_nCH(NH_2CO_2R10$ (R10 is alkyl, aryl) (n=1 to 5)
M is $In^{113}$, $In^{115}$ or a mixture of $In^{113}$ and $In^{115}$;
Z is a halide, acetate, OH.

79. A method as claimed in claim 41 wherein the phototherapeutic compound or composition has the structure:

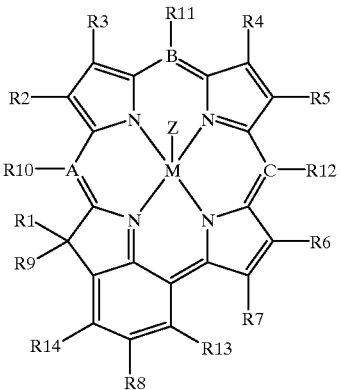

where each of R1–R14 is H, halide, alkyl, cyclic alkyl (3–6 carbons), aryl, substituted aryl, alkenyl, substituted alkenyl, alkynyl, substituted alkynyl, amide, ester, CH=CHCH$_2$H (CH$_3$)$_2$, CH=CHCH$_2$N$^+$(CH$_3$)$_3$ X$^-$ (where X is a charge balancing ion), $C(X1)_2C(X1)_3$ (where X1 is a halogen), NR15R15, Cn, OH, OR15, CHO, $(CH_2)_nOH$, $(CH_2)_nSH$, $(CH_2)_nO$-alkoxy, CH(OH)CH$_3$, CH(OR15)CH$_3$ $(CH_2)_nSR15$, $(CH_2)_nOR15$ (where n=1, 2, 3, 4, and R15 is a functional group less than or equal to 100,000 daltons), $(CH_2)_nCO_2R16$ (where R16 is H, a physiologically acceptable salt, alkyl (1–6 carbons), aryl, substituted aryl, alkenyl, substituted alkenyl, alkynyl, and n=1, 2, 3, 4), $(CH_2)_nCONHR15$, $(CH_2nCON(R15)_2$, $CO_2R15$, CONHR15, CONR15R15, SR15, $SO_3H$, $SO_3R15$, $SO_2NHR15$, $SO_2N(R15)_2$; A, B, C are C, N, O$^+$, O, S, Te, P or combinations thereof; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100,000 daltons.

80. A method as claimed in claim 41 wherein the phototherapeutic compound or composition has the structure:

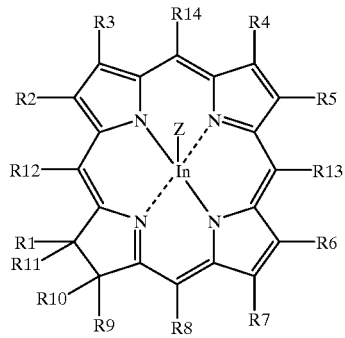

where each of R1 through R14 is H, halide, alkyl, cyclic alkyl (1–6 carbons), aryl, substituted aryl, alkenyl, substituted alkenyl, alkynyl, substituted alklynyl, amide, ester, $C(X1)_2C(X1)_3$ (where X1 is a halogen), NR15R15, CN, OH, OR15, CHO, $COCH_3$, $(CH_2)_nOH$, $(CH_2)_nSH$, $(CH_2)_nO$-alkoxy, $(CH_2)_nSR15$, $(CH_2)_nOR15$ (where n=1, 2, 3, 4, and R15 is a functional group less than or equal to 100,000 daltons), $(CH_2)_nCO_2R16$ (where R16 is H, a physiologically acceptable salt, alkyl (1–6 carbons), aryl, substituted aryl, alkenyl, substituted alkenyl, alkynyl, or substituted alkynyl, and n=1, 2, 3, 4), $(CH_2)_nCONHR15$, $(CH_2NCON(R15)_2$, $CO_2R15$, CONHR15, $CON(R15)_2$, SR15, $SO_3H$, $SO_3R15$, $SO_2NHR15$, $SO_2N(R15)_2$; M is $In^{113}$, $In^{115}$ or a mixture of $In^{113}$ and $In^{115}$, Z is a halide, acetate, OH, alkyl, aryl, substituted aryl, alkenyl, substituted alkenyl, alkynyl or substituted alkynyl, or a functional group less than or equal to 100,000 daltons, protein or biomolecule.

81. A method as claimed claim 41 wherein the phototherapeutic compound or composition has the structure:

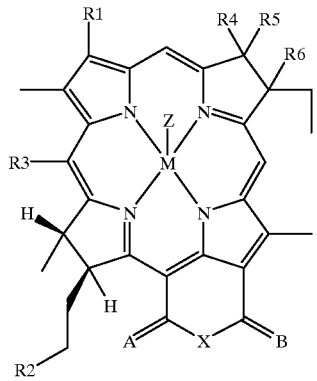

wherein;
R1 is $CH=CH_2$, Et, CHO, or $COCH_3$
R4 is Me
R3 is H
each of R5 and R6 is OH
R2 is $CO_2CH_3$, $CO_2H$, $CO_2R7$ (R7 is alkyl or phenyl), or an amide
Each of A and B is O or NR8 (R8 is alkyl)
X is O or NR9 (R9 is alkyl, an amino acid, an alcohol containing group, or an ether containing group)
M is $In^{113}$, $In^{115}$ or a mixture of $In^{113}$ and $In^{115}$
Z is a halide, acetate, or OH.

82. A method as claimed in claim 41 wherein the phototherapeutic compound or composition has the structure:

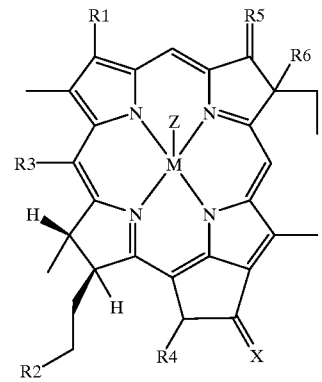

where each of R1–R6 is $CH_2CH_3$, $CH=CH_2$, $CH=CHCH_2N(CH_3)_2$, $CH=CHCH_2N^+(CH_3)_3$ $X1^-$, $C(X2)_2C(X2)_3$, CHO, $COCH_3$, $CO_2H$, $CO_2R7$, CONHR7, $CH=CHCHO$, $CH_2Y$, $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, Oh, OR7, CHO, $(CH_2)_nOH$, $(CH_2)_nSH$, $(CH_2)_nO$-alkoxy, $(CH_2)_nSR7$, $(CH_2)_nOR7$, $(CH_2)_nCO_2R7'$, $(CH_2)_nCONHR7$, $CO_2R7$, CONHR7, CONHR7, CONR7R7, SR7, $SO_3H$, $SO_3R7$, $SO_2NHR7$, $SO_2N(R7)_2$, a protein or biomolecule or a functional group less than or equal to 100,000 daltons; X is O, $H_2$, (H, OH), S, or a ketone protecting group; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100,000 daltons wherein
X1 is a charge balancing ion
R7 is a functional group less than or equal to 100,000 daltons
Y=H, halogen, OH, OR7 or is a functional group less than or equal to 100,000 daltons
X2 is a halogen
n=1, 2, 3, 4, and
R7' is H, a physiologically acceptable salt, alkyl (1–6 carbons), aryl, substituted aryl,
alkenyl, substituted alkenyl, alkynyl or substituted alkynyl.

83. A method as claimed in claim 41 wherein the phototherapeutic compound or composition has the structure:

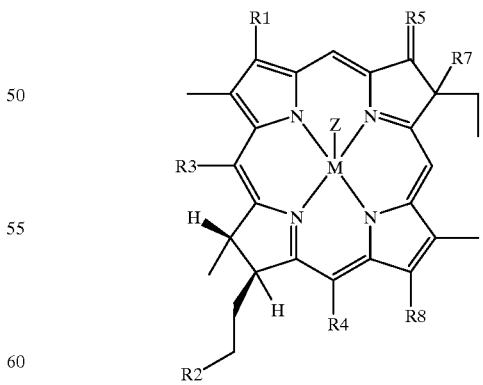

where each of R1–R8 is $CH_2CH_3$, $CH=CH_2$, $CH=CHCH_2N(CH_3)_2$, $CH=CHCH_2N^+(CH_3)_3$ $X^-$, $C(X1)_2C(X1)_3$, CHO, $COCH_3$, $CO_2H$, $CO_2R9$, CONHR9, $CH=CHCHO$, $CH_2Y$, $CH_2CO_2R9$, $CH_2CONHR9$, $CH=CHCH_2OH$, $CH=CHCH_2OR9$, $CH(OH)CH_3$, $CH(OR9)CH_3$, H, halide, alkyl, cyclic alkyl (3–6 carbons), aryl, substituted aryl, alkenyl, substituted alkenyl, alkynyl, substituted alkynyl, amide, ester, Nr9R9, CN, O, S, NHR9, OH, OR9, CHO, $(CH_2)_nOH$, $(CH_2)_nSH$, $(CH_2)_nO$-alkoxy, $(CH_2)_nSR9$, $(CH_2)_nOR9$, $(CH_2)_nCO_2R9'$, $(CH_2)_nCONHR9$, $(CH_2)_nCON(R9)_2$, $CO_2R9$, CONHR9, CONR9R9, SR9, $SO_3H$, $SO_3R9$, $SO_2NHR9$, $SO_2N(R9)_2$, $SO_2N(R9)_3^{+X-}$, protein or biomolecule or functional group less than or equal to 100,000 daltons; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, a protein or biomolecule or functional group less than or equal to 100,000 daltons, wherein X is a charge balancing ion R9 is a functional group less than or equal to 100,000 daltons Y=H, halogen, OH, OR9 or is a functional group less than or equal to 100,000 daltons X1 is a halogen N=1, 2, 3, 4, and R9' is H, a physiologically acceptable salt, alkyl (1–6 carbons), aryl, substituted aryl, alkenyl, substituted alkenyl, alkynyl or substituted alkynyl.

84. A method as claimed in claim 41 wherein the phototherapeutic compound or composition has the structure:

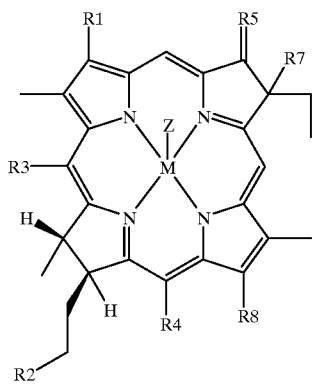

wherein;

R1 is $CH=CH_2$, Et, CHO, or $COCH_3$

R5 is O or NR9 (where R9 is alkyl)

R7 is Me

R3 is H

R4 and R8 are H, $CO_2CH_3$, $CO_2H$ (or a salt thereof), $CO_2R10$ (R10 is an alkyl or phenyl group), an amide, $CH_2CO_2CH_3$, $CH_2CO_2H$ (or a salt thereof), R2 is $CO_2CH_3$, $CO_2H$, $CO_2R10$ (R10 is an alkyl or a phenyl group), or an amide M is $In^{113}$, $In^{115}$ or a mixture of $In^{113}$ and $In^{115}$, and Z is a halide, acetate, or OH.

85. A method as claimed in claim 41 wherein the phototherapeutic compound or composition has the structure:

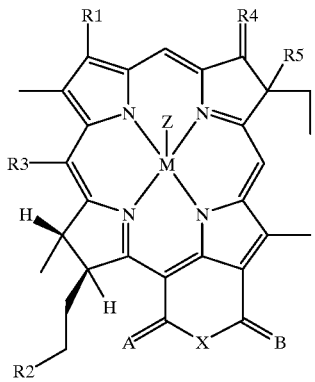

where each of R1–R5 is $CH_2CH_3$, $CH=CH_2$, $CH=CHCH_2N(CH_3)_2$, $CH=CHCH_2N^+(CH_3)_3$ $X1^-$, $C(X2)_2C(X2_3$, CHO, $COCH_3$, $CO_2H$, $CO_2R6$, CONHR6, CH=CHCHO, $Ch_2Y$, $CH_2CO_2R6$, $CH_2CONHR6$, $CH=CHCH_2OH$, $CH(OH)CH_3$, $CH(OR6)CH_3$, H, halide, alkyl cyclic alkyl (3–6 carbons), aryl, substituted aryl, alkenyl, substituted alkenyl, alkynyl, substituted alkynyl, amide, ester, NR6R6, CN, O, S, NHR6, OH, OR6, CHO, $(CH_2)_nOH$, $(CH_2)_nSH$, $(CH_2)_nO$-alkoxy, $(CH_2)_nSR6$, $(CH_2)_nOR6$, $(CH_2)_nCO_2R7$, $SO_2N(R6)_2$, a protein or biomolecule or a functional group less than or equal to 100,000 daltons; X is O, NR8; Z is a halide, acetate, OH, alkyl, aryl, substituted aryl, alkenyl, substituted alkenyl, alkynyl, substituted alkynyl, protein or biomolecule or functional group less than or equal to 100,000 daltons wherein X1 is a charge balancing ion R6 is a functional group less than or equal to 100,000 daltons Y=H, halogen, OH, OR6 or is a functional group less than or equal to 100,000 daltons X2 is a halogen N=1, 2, 3, 4, and R7 is H, a physiologically acceptable salt, alkyl (1–6 carbons), aryl, substituted aryl, alkenyl, substituted alkenyl, alkynyl or substituted alkynyl R8 is H, alkyl (1–10 carbons), aryl, substituted aryl, alkenyl, substituted alkenyl, alkynyl, substituted alkynyl, an amino acid, an amino acid ester or a functional group equal to or less than 100,000 daltons, and A and B are O or NR9 where R9 is alkyl.

86. A method as claimed in claim 41 wherein the phototherapeutic compound or composition has the structure:

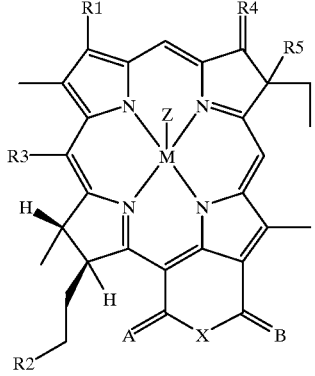

wherein:

R1 is $CH=CH_2$, Et, CHO, or $COCH_3$

R4 is O or NR6 (where R6 is alkyl)

R5 is Me

R3 is H

R2 is $CO_2CH_3$, $CO_2H$, $CO_2R7$ (R7 is an alkyl or a phenyl group), or an amide X is O, NR8 (R8 is alkyl, an amino acid, an alcohol containing group, or an ether containing group)

M is $In^{113}$, $In^{115}$ or a mixture of $In^{113}$ and $In^{115}$

Z is a halide, acetate, OH, and

A and B are O or NR9 where R9 is alkyl.

87. A method as claimed in claim 41 wherein the phototherapeutic compound or composition has the structure:

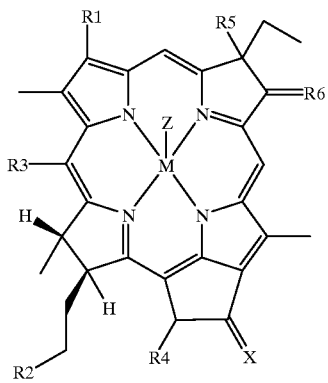

where each of R1–R6 is $CH_2CH_3$, $CH=CH_2$, $CH=CHCH_2N(CH_3)_2$, $CH=CHCH_2N^+(CH_3)_3$ $X^-$, $C(X2)_2C(X2)_3$, CHO, $COCH_3$, $CO_2H$, $CO_2R7$, CONHR7, CH=CHCHO, $CH_2Y$, $CH_2CO_2R7$, $CH_2CONHR7$, $CH=CHCH_2OH$, $CH=CHCH_2OR7$, $CH(OH)CH_3$, $CH(OR7)CH_3$, H, halide, alkyl, cyclic alkyl (3–6 carbons), aryl, substituted aryl, alkenyl, substituted alkenyl, alkynyl, substituted alkynyl, amide, ester, NR7R7, CN, O, S, NHR7, OH, OR7, CHO, $(CH_2)_nOH$, $(CH_2)_nSH$, $(CH_2)_n O$-alkoxy, $(CH_2)_nSR7$, $(CH_2)_nOR7$, $(CH_2)_nCO_2R8$, $(CH_2)_nCONHR7$, $CO_2R7$, CONHR7, CONR7R7, SR7, $SO_3H$, $SO_3R7$, $SO_2NHR7$, $SO_2N(R7)_2$, a protein or biomolecule or a functional group less than or equal to 100,000 daltons; X is O, $H_2$, (H, OH), S, or a ketone protecting grop; M is $In^{113}$, $In^{115}$ or a mixture of $In^{113}$ and $In^{115}$; Z is a halide, acetate, OH, alkyl, aryl, substituted aryl, alkenyl, substituted alkenyl, alkynyl, substituted alkynyl, protein or biomolecule or functional group less than or equal to 100,000 daltons;

* * * * *